(12) United States Patent
Iyengar et al.

(10) Patent No.: US 6,555,522 B1
(45) Date of Patent: Apr. 29, 2003

(54) PEPTIDES AND OTHER SMALL MOLECULES DERIVED FROM REGIONS OF INTERACTING PROTEINS AND USES THEREOF

(75) Inventors: Srinivas Ravi V. Iyengar, Mohegan Lake; Gezhi Weng, New York; Yibang Chen, Woodside; Harel Weinstein, New York, all of NY (US); Elizabeth Buck, Hadlyme, CT (US)

(73) Assignee: Mount Sinai School of Medicine of the City of New York, New York, NY (US)

( * ) Notice: Subject to any disclaimer, the term of this patent is extended or adjusted under 35 U.S.C. 154(b) by 0 days.

(21) Appl. No.: 09/245,039

(22) Filed: Feb. 5, 1999

Related U.S. Application Data

(60) Provisional application No. 60/073,765, filed on Feb. 5, 1998.

(51) Int. Cl.$^7$ .................. A61K 38/00; A61K 38/04; A61K 38/08; A61K 38/10; A61K 38/16

(52) U.S. Cl. .............. 514/13; 514/2; 514/14; 514/17; 514/21; 530/300; 530/326; 530/327; 530/329

(58) Field of Search .................. 530/300, 350, 530/324, 325, 326, 327, 328, 329, 345, 387; 514/2, 12, 13, 14, 15, 16, 17, 21; 435/69, 1, 7.1

(56) References Cited

U.S. PATENT DOCUMENTS 5,519,003 A * 5/1996 Mochly-Rosen et al.
5,750,353 A    5/1998 Kopin et al.

FOREIGN PATENT DOCUMENTS

WO    WO 98/00538    1/1998

OTHER PUBLICATIONS

Ballesteros & Weinstein, 1995, "Integrated methods for the construction of three–dimensional models and computational probing of structure–function relations in G protein–coupled receptors", Methods in Neuro. 25:366–428.
Bourne, 1997, "How receptors talk to trimeric G proteins", Curr. Opin. Cell Biol. :134–142.
Bourne, 1997, "The arginine finger strikes again", Nature 389:673–674.
Bourne, 1997, "Pieces of the true grail: a G protein finds its target", Science 278:1898–1899.
Buck, 1999, "Resolution of a signal transfer region from a general binding domain in Gβ for stimulation of phospholipase C–β2", Science 283: 1332–1335.
Chen et al., 1995, "A region of adenylyl cyclase 2 critical for regulation by G protein βY subunits", Science 268: 1166–1169.
Chen et al., 1997, "A surface on the G protein β–subunit involved in interactions with adenylyl cyclases", PNAS USA 94: 2711–2714.
DeVivo & Iyengar, 1994, "G protein pathways: signal processing be effectors", Molec. Cell. Endocrinol. 100: 65–70.
Dietzel & Kurjan, J., 1987, "The yeast SCG1 gene: A Gα–like protein implicated in the a– and α–factor response pathway", Cell 50: 1000–1010.
Dingus et al., 1994, "Synthesis and use of biotinylated βY complexes prepared from bovine brain G proteins", Methods Enzymol. 237: 457–471.
Dyson, 1991, "Immobilization of nucleic acids and hybridization analysis", In: Essential Molecular Biology: A Practical Approach, vol. 2 (T.A. Brown, ed.) pp. 111–156, Oxford Univ Press, Oxford.
Ford et al., 1998, Molecular basis for interactions of G protein βY subunits with effectors, Science 280: 1271–1274.
Fung et al., 1981, "Flow of information in the light–triggered cyclic nucleotide cascade of vision", Proc. Natl. Acad. Sci. USA 78: 152–156.
Gilman, 1987, "G proteins: transducers of receptor–generated signals", Annu. Rev. Biochem. 56: 615–649.
Grishin et al., 1994, "Biochemical and genetic analysis of dominant–negative mutations affecting a yeast G protein Y subunit", Mol. Cell. Biol. 14:4571–4578.

(List continued on next page.)

*Primary Examiner*—Karen Cochrane Carlson
*Assistant Examiner*—Billy D Chism
(74) *Attorney, Agent, or Firm*—Pennie & Edmonds LLP

(57) ABSTRACT

The present invention relates generally to the field of peptides and other small molecules (i.e. peptide mimetics) as pharmaceutical and/or therapeutic agents, and to methods for identification and design of peptides and peptide mimetics having desired functional activities. Specifically, peptides and other small molecules derived from regions of interacting intracellular signaling proteins are provided. More specifically, peptides and other small molecules derived from regions of the Gβ subunit of heterotrimeric GTP binding proteins are provided. Such molecules include specific agonists and antagonists of Gβ downstream effectors, including adenylyl cyclase and phospholipase C. Such molecules are targeted to predicted regions of interaction between intracellular signaling proteins and tested for activity in functional assays using methods of the invention. One major advantage of the invention is the incorporation of three-dimensional structural information in models used for predicting interaction surfaces between intracellular proteins. Another major advantage is the ability to distinguish, within a predicted interaction surface, a signal transfer region from a general binding domain. Resolution of such signal transfer regions from general binding domains is useful for prediction and validation of pharmacologic and therapeutic agonists and antagonists.

23 Claims, 19 Drawing Sheets

Figure 1A:
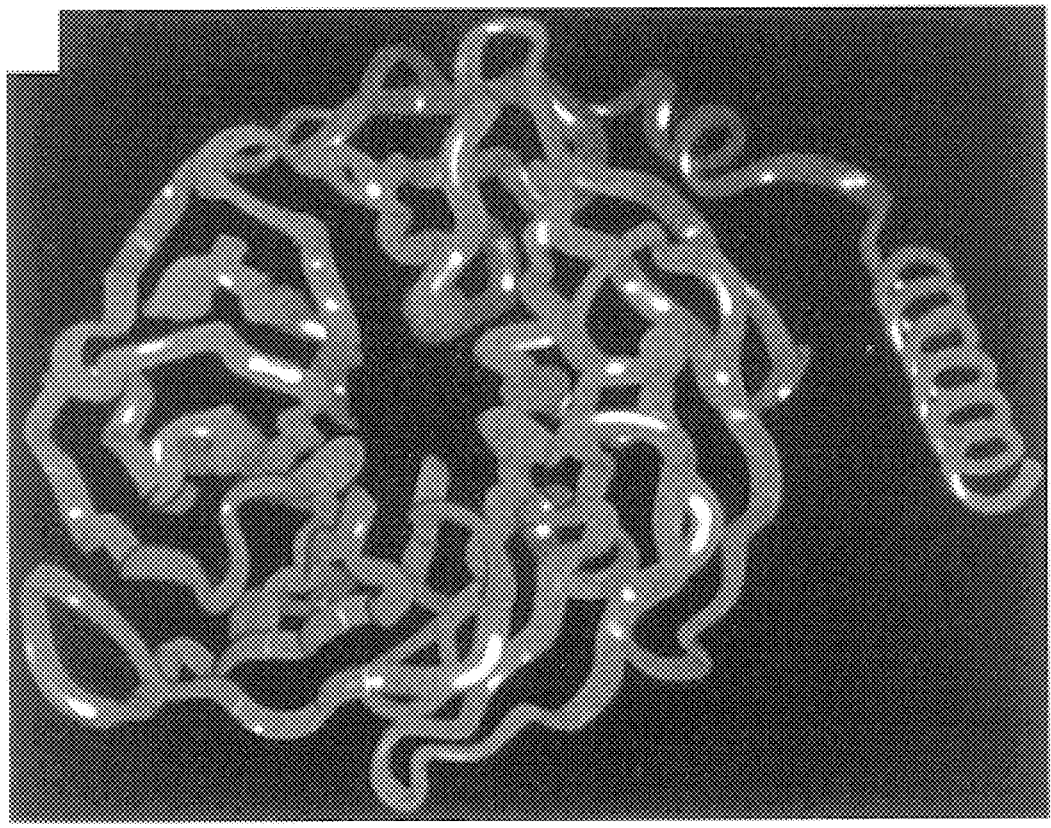

(4 of 19 Drawing Sheet(s) Filed in Color)-

OTHER PUBLICATIONS

Guarnieri & Weinstein, 1996, "Conformational memories and the exploration of biologically relevant peptide conformations: an illustration for the gonadotropin–releasing hormone", J. Am. Chem. Soc. 118:5580–5589.

Hamm, 1998, "The many faces of G protein signaling", J. Biol. Chem. 273:669–672.

Harry et al., 1997, "Differential regulation of adenylyl cyclases by G alphas", J. Biol. Chem. 272:19017–19021.

Iniguez–Lluhi et al., 1992, "G protein βY subunits synthesized in Sf9 cells", J. Biol. Chem. 267:23409–23417.

Iyengar, 1993, "Multiple families of Gs–regulated adenylyl cyclases", Adv. Sec. Mess. Phosphoprot. Res. 28:27–36.

Iyengar, 1993, "Molecular and functional diversity of mammalian $G_S$–stimulated adenylyl cyclases", FASEB J. 7:768.

Jacobowitz & Iyengar, 1994, "Phorbol ester–induced stimulation and phosphorylation of adenylyl cyclase 2", Proc. Natl. Acad. Sci. USA 91:10630–10634.

Jacobowitz et al., 1993, "Stimulation of specific types of $G_s$–stimulated adenylyl cyclases by phorbol ester treatment", J. Biol. Chem. 268:3829–3832.

Lambright et al., 1996, "The 2.0Å crystal structure of a heterotrimeric G protein", Nature 379:311–319.

Li et al., 1998, "Sites for G alpha binding on the G protein beta subunit overlap with sites for regulation of phospholipase C beta and adenylyl cyclase", J. Biol. Chem. 273:16265–16272.

Logothetis et al., 1987, "The βY subunits of GTP–binding proteins activate the muscarinic $K^+$channel in heart", Nature (London) 273:321–326.

Panchenko et al., 1998, "Sites important for PLCbeta2 activation by the G protein betagamma subunit map to the sides of the beta propeller structure", J. Biol. Chem. 273:28298–28304.

Pawson, 1995, "Protein modules and signalling networks", Nature 373:573–580.

Northup et al., 1983, "The subunits of the stimulatory regulatory component of adenylate cyclase", J. Biol. Chem. 258:11369–11376.

Pieroni et al., 1993, "Signal recognition and integration by Gs–stimulated adenylyl cyclases", Curr. Opin. Neurobiol. 3:345–351.

Portotoghese, 1989, "Bivalent ligands and the message—address concept in the design of selective opioid receptor antagonists", TIPS 10:230–235.

Portoghese et al., 1990, "Design of peptidomimetic σ opiod receptor antagonists using the message–address concept", J. Med. Chem. 33:1714–1720.

Schwyzer, 1980, "Structure and function in neuropeptides", Proc. R. Soc. Lond. 210:5–20.

Smit & Iyengar, 1998, "Mammalian adenylyl cyclases", Adv. Sec. Mess. Phosphoprot. Res. 32:1–21.

Sondek et al., 1996, "Crystal structure of a $G_A$protein βY dimer at 2.1Å resolution", Nature (London) 379:369–374.

Takasaki et al., 1997, "Structure–based design and characterization of exocyclic peptidomimetics that inhibit TNFα binding to its receptor", Nature Biotechnology 15:1266–1270.

Tang & Gilman, 1991, "Type–specific regulation of adenylyl cyclase by G protein βY subunits", Science 254:1500–1503.

Taussig & Gilman, 1995, "Mammalian membrand–bound adenylyl cyclases", J. Biol. Chem. 270:1–4.

Thanos, 1999, "Oligomeric structure of the human EphB2 receptor SAM domain", Science 283:833–836.

Tian et al., 1998, "A small, nonpeptidyl mimic of granulocyte–colony–stimulating factor", Science 281:257–259.

Wedegaertner et al., 1995, "Lipid modifications of trimeric G proteins", J. Biol. Chem. 270:503–506.

Weinstein, 1995, "*E Pur Si Muove*:Dynamic modeling of ligand–induced activation in G–protein coupled receptors", Chem. Design Automation News 10(2):38–43.

Weinstein & Zhang, 1995, "Receptor models and ligand–induced responses: new insights for structure–activity relations", *QSAR and Molecular Modeling: Concepts, Computational Tools and Biological Applications*, Prous Science Publishers, p. 497–507.

Weng et al., 1996, "Gβ subunit interacts with a peptide encoding region 956–982 of adenylyl cyclase 2", J. Biol. Chem. 271:26445–26448.

Whiteway et al., 1994, "Genetic identification of residues involved in association of α and β G–protein subunits", Mol. Cell. Biol, 14:3223–3229.

Wrighton et al., 1997, "Increased potency of an erythropoietin peptide mimetic through covalent dimerization", Nature Biotech. 15:1261–1265.

Yan & Gautam, 1996, "A domain on the G protein β subunit interacts with both adenylyl cyclase 2 and the muscarinic atrial potassium channel", J. Biol. Chem. 27:17597–17601.

Yan & Gautam, 1997, "Structural determinants for interaction with three different effectors on the G protein beta subunit", J. Biol. Chem. 272:2056–2059.

* cited by examiner

SEQUENCE LISTING

<160> NUMBER OF SEQ ID NOS: 10

<210> SEQ ID NO 1
<211> LENGTH: 340
<212> TYPE: PRT
<213> ORGANISM: Homo sapiens

<400> SEQUENCE: 1

```
Met Ser Glu Leu Asp Gln Leu Arg Gln Glu Ala Glu Gln Leu Lys Asn
 1               5                  10                  15

Gln Ile Arg Asp Ala Arg Lys Ala Cys Ala Asp Ala Thr Leu Ser Gln
            20                  25                  30

Ile Thr Asn Asn Ile Asp Pro Val Gly Arg Ile Gln Met Arg Thr Arg
        35                  40                  45

Arg Thr Leu Arg Gly His Leu Ala Lys Ile Tyr Ala Met His Trp Gly
    50                  55                  60

Thr Asp Ser Arg Leu Leu Val Ser Ala Ser Gln Asp Gly Lys Leu Ile
65                  70                  75                  80

Ile Trp Asp Ser Tyr Thr Thr Asn Lys Val His Ala Ile Pro Leu Arg
                85                  90                  95

Ser Ser Trp Val Met Thr Cys Ala Tyr Ala Pro Ser Gly Asn Tyr Val
            100                 105                 110

Ala Cys Gly Gly Leu Asp Asn Ile Cys Ser Ile Tyr Asn Leu Lys Thr
        115                 120                 125

Arg Glu Gly Asn Val Arg Val Ser Arg Glu Leu Ala Gly His Thr Gly
    130                 135                 140
```

```
Tyr Leu Ser Cys Cys Arg Phe Leu Asp Asp Asn Gln Ile Val Thr Ser
145                 150                 155                 160

Ser Gly Asp Thr Thr Cys Ala Leu Trp Asp Ile Glu Thr Gly Gln Gln
                165                 170                 175

Thr Thr Thr Phe Thr Gly His Thr Gly Asp Val Met Ser Leu Ser Leu
            180                 185                 190

Ala Pro Asp Thr Arg Leu Phe Val Ser Gly Ala Cys Asp Ala Ser Ala
        195                 200                 205

Lys Leu Trp Asp Val Arg Glu Gly Met Cys Arg Gln Thr Phe Thr Gly
210                 215                 220

His Glu Ser Asp Ile Asn Ala Ile Cys Phe Phe Pro Asn Gly Asn Ala
225                 230                 235                 240

Phe Ala Thr Gly Ser Asp Asp Ala Thr Cys Arg Leu Phe Asp Leu Arg
                245                 250                 255

Ala Asp Gln Glu Leu Met Thr Tyr Ser His Asp Asn Ile Ile Cys Gly
            260                 265                 270

Ile Thr Ser Val Ser Phe Ser Lys Ser Gly Arg Leu Leu Leu Ala Gly
        275                 280                 285

Tyr Asp Asp Phe Asn Cys Asn Val Trp Asp Ala Leu Lys Ala Asp Arg
290                 295                 300

Ala Gly Val Leu Ala Gly His Asp Asn Arg Val Ser Cys Leu Gly Val
305                 310                 315                 320

Thr Asp Asp Gly Met Ala Val Ala Thr Gly Ser Trp Asp Ser Phe Leu
                325                 330                 335

Lys Ile Trp Asn
            340

<210> SEQ ID NO 2
<211> LENGTH: 1134
<212> TYPE: PRT
<213> ORGANISM: Bos taurus

<400> SEQUENCE: 2

Met Ala Gly Ala Pro Arg Gly Arg Gly Gly Gly Gly Gly Gly Gly Gly
  1               5                  10                  15

Ala Gly Glu Ser Gly Gly Ala Glu Arg Ala Ala Gly Pro Gly Gly Arg
                20                  25                  30

Arg Gly Leu Arg Ala Cys Asp Glu Glu Phe Ala Cys Pro Glu Leu Glu
            35                  40                  45

Ala Leu Phe Arg Gly Tyr Thr Leu Arg Leu Glu Gln Ala Ala Thr Leu
        50                  55                  60

Lys Ala Leu Ala Val Leu Ser Leu Leu Ala Gly Ala Leu Ala Leu Ala
65                  70                  75                  80

Glu Leu Leu Gly Ala Pro Gly Pro Ala Pro Gly Leu Ala Lys Gly Ser
                85                  90                  95

His Pro Val His Cys Val Leu Phe Leu Ala Leu Leu Val Val Thr Asn
            100                 105                 110

Val Arg Ser Leu Gln Val Pro Gln Leu Gln Gln Val Gly Gln Leu Ala
        115                 120                 125

Leu Leu Phe Ser Leu Thr Phe Ala Leu Leu Cys Cys Pro Phe Ala Leu
130                 135                 140

Gly Gly Pro Ala Gly Ala His Ala Gly Ala Ala Val Pro Ala Thr
145                 150                 155                 160

Ala Asp Gln Gly Val Trp Gln Leu Leu Leu Val Thr Phe Val Ser Tyr
                165                 170                 175
```

-continued

```
Ala Leu Leu Pro Val Arg Ser Leu Leu Ala Ile Gly Phe Gly Leu Val
                180                 185                 190
Val Ala Ala Ser His Leu Leu Val Thr Ala Thr Leu Val Pro Ala Lys
        195                 200                 205
Arg Pro Arg Leu Trp Arg Thr Leu Gly Ala Asn Ala Leu Leu Phe Leu
    210                 215                 220
Gly Val Asn Val Tyr Gly Ile Phe Val Arg Ile Leu Ala Glu Arg Ala
225                 230                 235                 240
Gln Arg Lys Ala Phe Leu Gln Ala Arg Asn Cys Ile Glu Asp Arg Leu
                245                 250                 255
Arg Leu Glu Asp Glu Asn Glu Lys Gln Glu Arg Leu Leu Met Ser Leu
            260                 265                 270
Leu Pro Arg Asn Val Ala Met Glu Met Lys Glu Asp Phe Leu Lys Pro
        275                 280                 285
Pro Glu Arg Ile Phe His Lys Ile Tyr Ile Gln Arg His Asp Asn Val
    290                 295                 300
Ser Ile Leu Phe Ala Asp Ile Val Gly Phe Thr Gly Leu Ala Ser Gln
305                 310                 315                 320
Cys Thr Ala Gln Glu Leu Val Lys Leu Leu Asn Glu Leu Phe Gly Lys
                325                 330                 335
Phe Asp Glu Leu Ala Thr Glu Asn His Cys Arg Arg Ile Lys Ile Leu
            340                 345                 350
Gly Asp Cys Tyr Tyr Cys Val Ser Gly Leu Thr Gln Pro Lys Thr Asp
        355                 360                 365
His Ala His Cys Cys Val Glu Met Gly Leu Asp Met Ile Asp Thr Ile
    370                 375                 380
Thr Ser Val Ala Glu Ala Thr Glu Val Asp Leu Asn Met Arg Val Gly
385                 390                 395                 400
Leu His Thr Gly Arg Val Leu Cys Gly Val Leu Gly Leu Arg Lys Trp
                405                 410                 415
Gln Tyr Asp Val Trp Ser Asn Asp Val Thr Leu Ala Asn Val Met Glu
            420                 425                 430
Ala Ala Gly Leu Pro Gly Lys Val His Ile Thr Lys Thr Thr Leu Ala
        435                 440                 445
Cys Leu Asn Gly Asp Tyr Glu Val Glu Pro Gly His Gly His Glu Arg
    450                 455                 460
Asn Ser Phe Leu Lys Thr His Asn Ile Glu Thr Phe Phe Ile Val Pro
465                 470                 475                 480
Ser His Arg Arg Lys Ile Phe Pro Gly Leu Ile Leu Ser Asp Ile Lys
                485                 490                 495
Pro Ala Lys Arg Met Lys Phe Lys Thr Val Cys Tyr Leu Leu Val Gln
            500                 505                 510
Leu Met His Cys Arg Lys Met Phe Lys Ala Glu Ile Pro Phe Ser Asn
        515                 520                 525
Val Met Thr Cys Glu Asp Asp Asp Lys Arg Arg Ala Leu Arg Thr Ala
    530                 535                 540
Ser Glu Lys Leu Arg Asn Arg Ser Ser Phe Ser Thr Asn Val Val Gln
545                 550                 555                 560
Thr Thr Pro Gly Thr Arg Val Asn Arg Tyr Ile Gly Arg Leu Leu Glu
                565                 570                 575
Ala Arg Gln Met Glu Leu Glu Met Ala Asp Leu Asn Phe Phe Thr Leu
            580                 585                 590
```

```
Lys Tyr Lys Gln Ala Glu Arg Glu Arg Lys Tyr His Gln Leu Gln Asp
        595                 600                 605

Glu Tyr Phe Thr Ser Ala Val Val Leu Ala Leu Ile Leu Ala Ala Leu
        610                 615                 620

Phe Gly Leu Val Tyr Leu Leu Ile Ile Pro Gln Ser Val Ala Val Leu
625                 630                 635                 640

Leu Leu Leu Val Phe Cys Ile Cys Phe Leu Val Ala Cys Val Leu Tyr
                645                 650                 655

Leu His Ile Thr Arg Val Gln Cys Phe Pro Gly Cys Leu Thr Ile Gln
                660                 665                 670

Ile Arg Thr Val Leu Cys Ile Phe Ile Val Val Leu Ile Tyr Ser Val
                675                 680                 685

Ala Gln Gly Cys Val Val Gly Cys Leu Pro Trp Ser Trp Ser Ser Ser
        690                 695                 700

Pro Asn Gly Ser Leu Val Val Leu Ser Ser Gly Gly Arg Asp Pro Val
705                 710                 715                 720

Leu Pro Val Pro Pro Cys Glu Ser Ala Pro His Ala Leu Leu Cys Gly
                725                 730                 735

Leu Val Gly Thr Leu Pro Leu Ala Ile Phe Leu Arg Val Ser Ser Leu
                740                 745                 750

Pro Lys Met Ile Leu Leu Ala Val Leu Thr Thr Ser Tyr Ile Leu Val
        755                 760                 765

Leu Glu Leu Ser Gly Tyr Thr Lys Ala Met Gly Ala Gly Ala Ile Ser
        770                 775                 780

Gly Arg Ser Phe Glu Pro Ile Met Ala Ile Leu Leu Phe Ser Cys Thr
785                 790                 795                 800

Leu Ala Leu His Ala Arg Gln Val Asp Val Lys Leu Arg Leu Asp Tyr
                805                 810                 815

Leu Trp Ala Ala Gln Ala Glu Glu Arg Asp Asp Met Glu Lys Val
        820                 825                 830

Lys Leu Asp Asn Lys Arg Ile Leu Phe Asn Leu Leu Pro Ala His Val
        835                 840                 845

Ala Gln His Phe Leu Met Ser Asn Pro Arg Asn Met Asp Leu Tyr Tyr
850                 855                 860

Gln Ser Tyr Ser Gln Val Gly Val Met Phe Ala Ser Ile Pro Asn Phe
865                 870                 875                 880

Asn Asp Phe Tyr Ile Glu Leu Asp Gly Asn Asn Met Gly Val Glu Cys
                885                 890                 895

Leu Arg Leu Leu Asn Glu Ile Ile Ala Asp Phe Asp Glu Leu Met Asp
                900                 905                 910

Lys Asp Phe Tyr Lys Asp Leu Glu Lys Ile Lys Thr Ile Gly Ser Thr
                915                 920                 925

Tyr Met Ala Ala Val Gly Leu Ala Pro Thr Ala Gly Thr Lys Ala Lys
        930                 935                 940

Lys Cys Ile Ser Ser His Leu Ser Thr Leu Ala Asp Phe Ala Ile Glu
945                 950                 955                 960

Met Phe Asp Val Leu Asp Glu Ile Asn Tyr Gln Ser Tyr Asn Asp Phe
                965                 970                 975

Val Leu Arg Val Gly Ile Asn Val Gly Pro Val Val Ala Gly Val Ile
                980                 985                 990

Gly Ala Arg Arg Pro Gln Tyr Asp Ile Trp Gly Asn Thr Val Asn Val
        995                 1000                1005

Ala Ser Arg Met Asp Ser Thr Gly Val Gln Gly Arg Ile Gln Val Thr
```

-continued

```
                1010                1015                1020

Glu Glu Val His Arg Leu Leu Arg Arg Gly Ser Tyr Arg Phe Val Cys
1025                1030                1035                1040

Arg Gly Lys Val Ser Val Lys Gly Lys Gly Glu Met Leu Thr Tyr Phe
            1045                1050                1055

Leu Glu Gly Arg Thr Asp Gly Asn Gly Ser Gln Thr Arg Ser Leu Asn
            1060                1065                1070

Ser Glu Arg Lys Met Tyr Pro Phe Gly Arg Ala Gly Leu Gln Thr Arg
        1075                1080                1085

Leu Ala Gly His Pro Pro Val Pro Pro Ala Ala Gly Leu Pro Val
    1090                1095                1100

Gly Ala Gly Pro Gly Ala Leu Gln Gly Ser Gly Leu Ala Pro Gly Pro
1105                1110                1115                1120

Pro Gly Gln His Leu Pro Pro Gly Ala Ser Gly Lys Glu Ala
                1125                1130

<210> SEQ ID NO 3
<211> LENGTH: 1090
<212> TYPE: PRT
<213> ORGANISM: Rattus norvegicus

<400> SEQUENCE: 3

Met Arg Arg Arg Arg Tyr Leu Arg Asp Arg Ala Glu Ala Ala Ala
  1               5                  10                  15

Ala Ala Ala Gly Gly Gly Glu Gly Leu Gln Arg Ser Arg Asp Trp Leu
             20                  25                  30

Tyr Glu Ser Tyr Tyr Cys Met Ser Gln Gln His Pro Leu Ile Val Phe
         35                  40                  45

Leu Leu Leu Ile Val Met Gly Ala Cys Leu Ala Leu Leu Ala Val Phe
     50                  55                  60

Phe Ala Leu Gly Leu Glu Val Glu Asp His Val Ala Phe Leu Ile Thr
 65                  70                  75                  80

Val Pro Thr Ala Leu Ala Ile Phe Phe Ala Ile Phe Ile Leu Val Cys
                 85                  90                  95

Ile Glu Ser Val Phe Lys Lys Leu Leu Arg Val Phe Ser Leu Val Ile
                100                 105                 110

Trp Ile Cys Leu Val Ala Met Gly Tyr Leu Phe Met Cys Phe Gly Gly
            115                 120                 125

Thr Val Ser Ala Trp Asp Gln Val Ser Phe Phe Leu Phe Ile Ile Phe
        130                 135                 140

Val Val Tyr Thr Met Leu Pro Phe Asn Met Arg Asp Ala Ile Ile Ala
145                 150                 155                 160

Ser Ile Leu Thr Ser Ser His Thr Ile Val Leu Ser Val Tyr Leu
                165                 170                 175

Ser Ala Thr Pro Gly Ala Lys Glu His Leu Phe Trp Gln Ile Leu Ala
            180                 185                 190

Asn Val Ile Ile Phe Ile Cys Gly Asn Leu Ala Gly Ala Tyr His Lys
        195                 200                 205

His Leu Met Glu Leu Ala Leu Gln Gln Thr Tyr Arg Asp Thr Cys Asn
    210                 215                 220

Cys Ile Lys Ser Arg Ile Lys Leu Glu Phe Glu Lys Arg Gln Gln Glu
225                 230                 235                 240

Arg Leu Leu Leu Ser Leu Leu Pro Ala His Ile Ala Met Glu Met Lys
                245                 250                 255
```

-continued

```
Ala Glu Ile Ile Gln Arg Leu Gln Gly Pro Lys Ala Gly Gln Met Glu
            260                 265                 270

Asn Thr Asn Asn Phe His Asn Leu Tyr Val Lys Arg His Thr Asn Val
        275                 280                 285

Ser Ile Leu Tyr Ala Asp Ile Val Gly Phe Thr Arg Leu Ala Ser Asp
    290                 295                 300

Cys Ser Pro Gly Glu Leu Val His Met Leu Asn Glu Leu Phe Gly Lys
305                 310                 315                 320

Phe Asp Gln Ile Ala Lys Glu Asn Glu Cys Met Arg Ile Lys Ile Leu
                325                 330                 335

Gly Asp Cys Tyr Tyr Cys Val Ser Gly Leu Pro Ile Ser Leu Pro Asn
            340                 345                 350

His Ala Lys Asn Cys Val Lys Met Gly Leu Asp Met Cys Glu Ala Ile
        355                 360                 365

Lys Lys Val Arg Asp Ala Thr Gly Val Asp Ile Asn Met Arg Val Gly
    370                 375                 380

Val His Ser Gly Asn Val Leu Cys Gly Val Ile Gly Leu Gln Lys Trp
385                 390                 395                 400

Gln Tyr Asp Val Trp Ser His Asp Val Thr Leu Ala Asn His Met Glu
                405                 410                 415

Ala Gly Gly Val Pro Gly Arg Val His Ile Ser Ser Val Thr Leu Glu
            420                 425                 430

His Leu Asn Gly Ala Tyr Lys Val Glu Glu Gly Asp Gly Glu Ile Arg
        435                 440                 445

Asp Pro Tyr Leu Lys Gln His Leu Val Lys Thr Tyr Phe Val Ile Asn
    450                 455                 460

Pro Lys Gly Glu Arg Arg Ser Pro Gln His Leu Phe Arg Pro Arg His
465                 470                 475                 480

Thr Leu Asp Gly Ala Lys Met Arg Ala Ser Val Arg Met Thr Arg Tyr
                485                 490                 495

Leu Glu Ser Trp Gly Ala Ala Lys Pro Phe Ala His Leu His His Arg
            500                 505                 510

Asp Ser Met Thr Thr Glu Asn Gly Lys Ile Ser Thr Thr Asp Val Pro
        515                 520                 525

Met Gly Gln His Asn Phe Gln Asn Arg Thr Leu Arg Thr Lys Ser Gln
    530                 535                 540

Lys Lys Arg Phe Glu Glu Glu Leu Asn Glu Arg Met Ile Gln Ala Ile
545                 550                 555                 560

Asp Gly Ile Asn Ala Gln Lys Gln Trp Leu Lys Ser Glu Asp Ile Gln
                565                 570                 575

Arg Ile Ser Leu Leu Phe Tyr Asn Lys Asn Ile Glu Lys Glu Tyr Arg
            580                 585                 590

Ala Thr Ala Leu Pro Ala Phe Lys Tyr Tyr Val Thr Cys Ala Cys Leu
        595                 600                 605

Ile Phe Leu Cys Ile Phe Ile Val Gln Ile Leu Val Leu Pro Lys Thr
    610                 615                 620

Ser Ile Leu Gly Phe Ser Phe Gly Ala Ala Phe Leu Ser Leu Ile Phe
625                 630                 635                 640

Ile Leu Phe Val Cys Phe Ala Gly Gln Leu Leu Gln Cys Ser Lys Lys
                645                 650                 655

Ala Ser Thr Ser Leu Met Trp Leu Leu Lys Ser Ser Gly Ile Ile Ala
            660                 665                 670

Asn Arg Pro Trp Pro Arg Ile Ser Leu Thr Ile Val Thr Thr Ala Ile
```

-continued

```
                675                 680                 685
Ile Leu Thr Met Ala Val Phe Asn Met Phe Phe Leu Ser Asn Ser Glu
690                 695                 700
Glu Thr Thr Leu Pro Thr Ala Asn Thr Ser Asn Ala Asn Val Ser Val
705                 710                 715                 720
Pro Asp Asn Gln Ala Ser Ile Leu His Ala Arg Asn Leu Phe Phe Leu
                725                 730                 735
Pro Tyr Phe Ile Tyr Ser Cys Ile Leu Gly Leu Ile Ser Cys Ser Val
                740                 745                 750
Phe Leu Arg Val Asn Tyr Glu Leu Lys Met Leu Ile Met Met Val Ala
                755                 760                 765
Leu Val Gly Tyr Asn Thr Ile Leu Leu His Thr His Ala His Val Leu
770                 775                 780
Asp Ala Tyr Ser Gln Val Leu Phe Gln Arg Pro Gly Ile Trp Lys Asp
785                 790                 795                 800
Leu Lys Thr Met Gly Ser Val Ser Leu Ser Ile Phe Phe Ile Thr Leu
                805                 810                 815
Leu Val Leu Gly Arg Gln Ser Glu Tyr Tyr Cys Arg Leu Asp Phe Leu
                820                 825                 830
Trp Lys Asn Lys Phe Lys Lys Glu Arg Glu Glu Ile Glu Thr Met Glu
                835                 840                 845
Asn Leu Asn Arg Val Leu Leu Glu Asn Val Leu Pro Ala His Val Ala
850                 855                 860
Glu His Phe Leu Ala Arg Ser Leu Lys Asn Glu Glu Leu Tyr His Gln
865                 870                 875                 880
Ser Tyr Asp Cys Val Cys Val Met Phe Ala Ser Ile Pro Asp Phe Lys
                885                 890                 895
Glu Phe Tyr Thr Glu Ser Asp Val Asn Lys Glu Gly Leu Glu Cys Leu
                900                 905                 910
Arg Leu Leu Asn Glu Ile Ile Ala Asp Phe Asp Asp Leu Leu Ser Lys
                915                 920                 925
Pro Lys Phe Ser Gly Val Glu Lys Ile Lys Thr Ile Gly Ser Thr Tyr
                930                 935                 940
Met Ala Ala Thr Gly Leu Ser Ala Ile Pro Ser Gln Glu His Ala Gln
945                 950                 955                 960
Glu Pro Glu Arg Gln Tyr Met His Ile Gly Thr Met Val Glu Phe Ala
                965                 970                 975
Tyr Ala Leu Val Gly Lys Leu Asp Ala Ile Asn Lys His Ser Phe Asn
                980                 985                 990
Asp Phe Lys Leu Arg Val Gly Ile Asn His Gly Pro Val Ile Ala Gly
                995                 1000                1005
Val Ile Gly Ala Gln Lys Pro Gln Tyr Asp Ile Trp Gly Asn Thr Val
    1010                1015                1020
Asn Val Ala Ser Arg Met Asp Ser Thr Gly Val Leu Asp Lys Ile Gln
1025                1030                1035                1040
Val Thr Glu Glu Thr Ser Leu Ile Leu Gln Thr Leu Gly Tyr Thr Cys
                1045                1050                1055
Thr Cys Arg Gly Ile Ile Asn Val Lys Gly Lys Gly Asp Leu Lys Thr
                1060                1065                1070
Tyr Phe Val Asn Thr Glu Met Ser Arg Ser Leu Ser Gln Ser Asn Leu
                1075                1080                1085
Ala Ser
    1090
```

```
<210> SEQ ID NO 4
<211> LENGTH: 1181
<212> TYPE: PRT
<213> ORGANISM: Homo sapiens

<400> SEQUENCE: 4

Met Ser Leu Leu Asn Pro Val Leu Pro Pro Lys Val Lys Ala Tyr
 1               5                  10                  15

Leu Ser Gln Gly Glu Arg Phe Ile Lys Trp Asp Asp Glu Thr Thr Val
             20                  25                  30

Ala Ser Pro Val Ile Leu Arg Val Asp Pro Lys Gly Tyr Tyr Leu Tyr
             35                  40                  45

Trp Thr Tyr Gln Ser Lys Glu Met Glu Phe Leu Asp Ile Thr Ser Ile
     50                  55                  60

Arg Asp Thr Arg Phe Gly Lys Phe Ala Lys Met Pro Lys Ser Gln Lys
 65                  70                  75                  80

Leu Arg Asp Val Phe Asn Met Asp Phe Pro Asp Asn Ser Phe Leu Leu
                 85                  90                  95

Lys Thr Leu Thr Val Val Ser Gly Pro Asp Met Val Asp Leu Thr Phe
            100                 105                 110

His Asn Phe Val Ser Tyr Lys Glu Asn Val Gly Lys Ala Trp Ala Glu
            115                 120                 125

Asp Val Leu Ala Leu Val Lys His Pro Leu Thr Ala Asn Ala Ser Arg
    130                 135                 140

Ser Thr Phe Leu Asp Lys Ile Leu Val Lys Leu Lys Met Gln Leu Asn
145                 150                 155                 160

Ser Glu Gly Lys Ile Pro Val Lys Asn Phe Gln Met Phe Pro Ala
                165                 170                 175

Asp Arg Lys Arg Val Glu Ala Ala Leu Ser Ala Cys His Leu Pro Lys
                180                 185                 190

Gly Lys Asn Asp Ala Ile Asn Pro Glu Asp Phe Pro Glu Pro Val Tyr
                195                 200                 205

Lys Ser Phe Leu Met Ser Leu Cys Pro Arg Pro Glu Ile Asp Glu Ile
    210                 215                 220

Phe Thr Ser Tyr His Ala Lys Ala Lys Pro Tyr Met Thr Lys Glu His
225                 230                 235                 240

Leu Thr Lys Phe Ile Asn Gln Lys Gln Arg Asp Ser Arg Leu Asn Ser
                245                 250                 255

Leu Leu Phe Pro Pro Ala Arg Pro Asp Gln Val Gln Gly Leu Ile Asp
                260                 265                 270

Lys Tyr Glu Pro Ser Gly Ile Asn Ala Gln Arg Gly Gln Leu Ser Pro
    275                 280                 285

Glu Gly Met Val Trp Phe Leu Cys Gly Pro Glu Asn Ser Val Leu Ala
    290                 295                 300

Gln Asp Lys Leu Leu Leu His His Asp Met Thr Gln Pro Leu Asn His
305                 310                 315                 320

Tyr Phe Ile Asn Ser Ser His Asn Thr Tyr Leu Thr Ala Gly Gln Phe
                325                 330                 335

Ser Gly Leu Ser Ser Ala Glu Met Tyr Arg Gln Val Leu Leu Ser Gly
            340                 345                 350

Cys Arg Cys Val Glu Leu Asp Cys Trp Lys Gly Lys Pro Pro Asp Glu
        355                 360                 365

Glu Pro Ile Ile Thr His Gly Phe Thr Met Thr Thr Asp Ile Phe Phe
```

```
                    370                 375                 380
Lys Glu Ala Ile Glu Ala Ile Ala Glu Ser Ala Phe Lys Thr Ser Pro
385                 390                 395                 400

Tyr Pro Ile Ile Leu Ser Phe Glu Asn His Val Asp Ser Pro Arg Gln
                405                 410                 415

Gln Ala Lys Met Ala Glu Tyr Cys Arg Thr Ile Phe Gly Asp Met Leu
            420                 425                 430

Leu Thr Glu Pro Leu Glu Lys Phe Pro Leu Lys Pro Gly Val Pro Leu
        435                 440                 445

Pro Ser Pro Glu Asp Leu Arg Gly Lys Ile Leu Ile Lys Asn Lys Lys
    450                 455                 460

Asn Gln Phe Ser Gly Pro Thr Ser Ser Lys Asp Thr Gly Gly Glu
465                 470                 475                 480

Ala Glu Gly Ser Ser Pro Pro Ser Ala Pro Ala Val Trp Ala Gly Glu
                485                 490                 495

Glu Gly Thr Glu Leu Glu Glu Glu Val Glu Glu Glu Glu Glu
            500                 505                 510

Glu Ser Gly Asn Leu Asp Glu Glu Glu Ile Lys Lys Met Gln Ser Asp
        515                 520                 525

Glu Gly Thr Ala Gly Leu Glu Val Thr Ala Tyr Glu Glu Met Ser Ser
    530                 535                 540

Leu Val Asn Tyr Ile Gln Pro Thr Lys Phe Val Ser Phe Glu Phe Ser
545                 550                 555                 560

Ala Gln Lys Asn Arg Ser Tyr Val Ile Ser Ser Phe Thr Glu Leu Lys
                565                 570                 575

Ala Tyr Asp Leu Leu Ser Lys Ala Ser Val Gln Phe Val Asp Tyr Asn
            580                 585                 590

Lys Arg Gln Met Ser Arg Ile Tyr Pro Lys Gly Thr Arg Met Asp Ser
        595                 600                 605

Ser Asn Tyr Met Pro Gln Met Phe Trp Asn Ala Gly Cys Gln Met Val
    610                 615                 620

Ala Leu Asn Phe Gln Thr Met Asp Leu Pro Met Gln Gln Asn Met Ala
625                 630                 635                 640

Val Phe Glu Phe Asn Gly Gln Ser Gly Tyr Leu Leu Lys His Glu Phe
                645                 650                 655

Met Arg Arg Pro Asp Lys Gln Phe Asn Pro Phe Ser Val Asp Arg Ile
            660                 665                 670

Asp Val Val Val Ala Thr Thr Leu Ser Ile Thr Val Ile Ser Gly Gln
        675                 680                 685

Phe Leu Ser Glu Arg Ser Val Arg Thr Tyr Val Glu Val Glu Leu Phe
    690                 695                 700

Gly Leu Pro Gly Asp Pro Lys Arg Arg Tyr Arg Thr Lys Leu Ser Pro
705                 710                 715                 720

Ser Thr Asn Ser Ile Asn Pro Val Trp Lys Glu Pro Phe Val Phe
                725                 730                 735

Glu Lys Ile Leu Met Pro Glu Leu Ala Ser Leu Arg Val Ala Val Met
            740                 745                 750

Glu Glu Gly Asn Lys Phe Leu Gly His Arg Ile Ile Pro Ile Asn Ala
        755                 760                 765

Leu Asn Ser Gly Tyr His His Leu Cys Leu His Ser Glu Ser Asn Met
    770                 775                 780

Pro Leu Thr Met Pro Ala Leu Phe Ile Phe Leu Glu Met Lys Asp Tyr
785                 790                 795                 800
```

-continued

```
Ile Pro Gly Ala Trp Ala Asp Leu Thr Val Ala Leu Ala Asn Pro Ile
            805                 810                 815
Lys Phe Phe Ser Ala His Asp Thr Lys Ser Val Lys Leu Lys Glu Ala
            820                 825                 830
Met Gly Gly Leu Pro Glu Lys Pro Phe Pro Leu Ala Ser Pro Val Ala
            835                 840                 845
Ser Gln Val Asn Gly Ala Leu Ala Pro Thr Ser Asn Gly Ser Pro Ala
        850                 855                 860
Ala Arg Ala Gly Ala Arg Glu Glu Ala Met Lys Glu Ala Ala Glu Pro
865                 870                 875                 880
Arg Thr Ala Ser Leu Glu Glu Leu Arg Glu Leu Lys Gly Val Val Lys
                885                 890                 895
Leu Gln Arg Arg His Glu Lys Glu Leu Arg Glu Leu Glu Arg Arg Gly
                900                 905                 910
Ala Arg Arg Trp Glu Glu Leu Leu Gln Arg Gly Ala Ala Gln Leu Ala
            915                 920                 925
Glu Leu Gly Pro Pro Gly Val Gly Gly Val Gly Ala Cys Lys Leu Gly
        930                 935                 940
Pro Gly Lys Gly Ser Arg Lys Lys Arg Ser Leu Pro Arg Glu Glu Ser
945                 950                 955                 960
Ala Gly Ala Ala Pro Gly Glu Gly Pro Glu Gly Val Asp Gly Arg Val
                965                 970                 975
Arg Glu Leu Lys Asp Arg Leu Glu Leu Glu Leu Leu Arg Gln Gly Glu
            980                 985                 990
Glu Gln Tyr Glu Cys Val Leu Lys Arg Lys Glu Gln His Val Ala Glu
        995                 1000                1005
Gln Ile Ser Lys Met Met Glu Leu Ala Arg Glu Lys Gln Ala Ala Glu
    1010                1015                1020
Leu Lys Ala Leu Lys Glu Thr Ser Glu Asn Asp Thr Lys Glu Met Lys
1025                1030                1035                1040
Lys Lys Leu Glu Thr Lys Arg Leu Glu Arg Ile Gln Gly Met Thr Lys
                1045                1050                1055
Val Thr Thr Asp Lys Met Ala Gln Glu Arg Leu Lys Arg Glu Ile Asn
                1060                1065                1070
Asn Ser His Ile Gln Glu Val Val Gln Val Ile Lys Gln Met Thr Glu
            1075                1080                1085
Asn Leu Glu Arg His Gln Glu Lys Leu Glu Glu Lys Gln Ala Ala Cys
        1090                1095                1100
Leu Glu Gln Ile Arg Glu Met Glu Lys Gln Phe Gln Lys Glu Ala Leu
1105                1110                1115                1120
Ala Glu Tyr Glu Ala Arg Met Lys Gly Leu Glu Ala Glu Val Lys Glu
                1125                1130                1135
Ser Val Arg Ala Cys Leu Arg Thr Cys Phe Pro Ser Glu Ala Lys Asp
                1140                1145                1150
Lys Pro Glu Arg Ala Cys Glu Cys Pro Pro Gly Leu Cys Glu Gln Asp
            1155                1160                1165
Pro Leu Ile Ala Lys Ala Asp Ala Gln Glu Ser Arg Leu
    1170                1175                1180
```

<210> SEQ ID NO 5
<211> LENGTH: 20
<212> TYPE: PRT
<213> ORGANISM: Homo sapiens

-continued

```
<400> SEQUENCE: 5

Thr Thr Asn Lys Val His Ala Ile Pro Leu Arg Ser Ser Trp Val Met
 1               5                  10                  15

Thr Cys Ala Tyr
            20

<210> SEQ ID NO 6
<211> LENGTH: 21
<212> TYPE: PRT
<213> ORGANISM: Homo sapiens

<400> SEQUENCE: 6

Gly Gly Leu Asp Asn Ile Cys Ser Ile Tyr Asn Leu Lys Thr Arg Glu
 1               5                  10                  15

Gly Asn Val Arg Val
            20

<210> SEQ ID NO 7
<211> LENGTH: 13
<212> TYPE: PRT
<213> ORGANISM: Homo sapiens

<400> SEQUENCE: 7

Lys Val His Ala Ile Pro Leu Arg Ser Ser Trp Val Met
 1               5                  10

<210> SEQ ID NO 8
<211> LENGTH: 6
<212> TYPE: PRT
<213> ORGANISM: Homo sapiens

<400> SEQUENCE: 8

Arg Ser Ser Trp Val Met
 1               5

<210> SEQ ID NO 9
<211> LENGTH: 6
<212> TYPE: PRT
<213> ORGANISM: Homo sapiens

<400> SEQUENCE: 9

Arg Arg Arg Trp Val Met
 1               5

<210> SEQ ID NO 10
<211> LENGTH: 6
<212> TYPE: PRT
<213> ORGANISM: Homo sapiens

<400> SEQUENCE: 10

Arg Arg Ser Trp Val Met
 1               5
```

PEPTIDES AND OTHER SMALL MOLECULES DERIVED FROM REGIONS OF INTERACTING PROTEINS AND USES THEREOF

This application claims priority of U.S. Provisional Patent Application No. 60/073,765, filed Feb. 5, 1998, which is incorporated by reference herein in its entirety.

This invention was made with United States government support under grant numbers DK-38761, DK-07645 and DA-00060, all from the National Institutes of Health. Accordingly, the United States has certain rights in the invention.

1. FIELD OF THE INVENTION

The present invention relates generally to the field of peptides and other small molecules (i.e. peptide mimetics) as pharmaceutical and/or therapeutic agents, and to methods for identification and design of peptides and peptide mimetics having desired functional activities. Specifically, peptides and other small molecules derived from regions of interacting intracellular signaling proteins are provided. More specifically, peptides and other small molecules derived from regions of the Gβ subunit of heterotrimeric GTP binding proteins are provided. Such molecules include specific agonists and antagonists of Gβ downstream effectors, including adenylyl cyclase and phospholipase C. Such molecules are targeted to predicted regions of interaction between intracellular signaling proteins and tested for activity in functional assays using methods of the invention. One major advantage of the invention is the incorporation of three-dimensional structural information in models used for predicting interaction surfaces between intracellular proteins. Another major advantage is the ability to distinguish, within a predicted interaction surface, a signal transfer region from a general binding domain. Resolution of such signal transfer regions from general binding domains is useful for prediction and validation of pharmacologic and therapeutic agonists and antagonists.

2. BACKGROUND OF THE INVENTION

The ability to target a desired drug intervention to a specific site in a biological system underlies the rational design of safe and effective drugs. Past drug design efforts have often focused on development of molecules believed to interact with cell surface receptors. For example, high-throughput assays have been used to screen synthetic organic compounds to identify molecules interacting with an extracellular domain of a cell surface receptor (Tian et al., 1998, A small, nonpeptidyl mimic of granulocyte-colony-stimulating factor, Science 281, 257–259). Further, methods have been developed for determining whether a candidate compound is an agonist of a peptide hormone receptor (see Kopin et al., U.S. Pat. No. 5,750,353, issued May 12, 1998, Assay for non-peptide agonists to peptide hormone receptors). Peptides and mimetics have also been developed based on the transmembrane domains of G-protein-coupled receptors (Bouvier et al., Jan. 8, 1998, Peptides and peptidomimetic compounds affecting the activity of G-protein-coupled receptors by altering receptor oligomerization, International Publication No. WO 98/00538). Examples of other extracellular ligands for which peptide mimetics have been developed include erythropoietin and TNFα (Wrighton et al., 1997, Increased potency of an erythropoietin peptide mimetic through covalent dimerization, Nature Biotechnology 15, 1261–1265; Takasaki et al., 1997, Structure-based design and characterization of exocyclic peptidomimetics that inhibit TNFα binding to its receptor, Nature Biotechnology 15, 1266–1270). Finally, distinct regions of peptide hormones have even been considered for design of receptor antagonists (Portoghese et al., 1990, Design of peptidomimetic δ opioid receptor antagonists using the message-address concept, J. Med. Chem. 33, 1714–1720).

Heterotrimeric GTP-binding proteins (G proteins) consisting of Gαβγ subunits are ubiquitous signal transduction proteins that play essential roles in intracellular communication (see e.g. DeVivo and Iyengar, 1994, G protein pathways: signal processing by effectors, Molec. Cell. Endocrinol. 100, 65–70). For example, the enzymatic production of cyclic AMP (cAMP) via adenylyl cyclases is regulated by G proteins (Smit and Iyengar, 1998, Mammalian adenylyl cyclases, Adv. Sec. Mess. Phosphoprot. Res. 32, 1–21; Iyengar, 1993, Multiple families of Gs-regulated adenylyl cyclases, Adv. Sec. Mess. Phosphoprot. Res. 28, 27–36; Pieroni et al., 1993, Signal recognition and integration by Gs-stimulated adenylyl cyclases, Curr. Opin. Neurobiol. 3, 345–351; Weng et al., 1996, G beta subunit interacts with a peptide encoding region 956–982 of adenylyl cyclase 2, cross-linking of the peptide to free G beta gamma but not the heterotrimer, J. Biol. Chem. 271, 26445–264488; Harry et al., 1997, Differential regulation of adenylyl cyclases by G alphas, J. Biol. Chem. 272, 19017–19021). G proteins provide a versatile system for investigation of intracellular protein-protein interactions by virtue of their interactions with multiple downstream effectors. For example, G protein βγ subunits regulate the activity of not on adenylyl cyclase but also phospholipase C-β2, calcium channels, potassium channels, and β-adrenergic receptor kinase (see e.g. Ford et al., 1998, Molecular basis for interactions of G protein βγ subunits with effectors, Science 280, 1271–1274).

Drug intervention beyond the cell surface, i.e. at intracellular protein-protein interaction sites, would broaden the array of potential targets for achieving a desired therapeutic effect. Intracellular targets may also provide intervention points having enhanced specificity compared to drugs targeted strictly at cell surface receptors. The ability to use intracellular interacting proteins as therapeutic targets for drug design has been less clearly established, however. One reason may be that an intracellular protein-protein interaction, unlike a typical cell surface hormone-receptor interaction, will often involve a multiplicity of proteins. Thus, resolution of specific interactions among three or more proteins will often be necessary to carry out design of safe and effective drugs. Accordingly, a need exists for a generally-applicable approach for identification of peptides and mimetics thereof having selective activity at a chosen intracellular site of action.

3. SUMMARY OF THE INVENTION

This invention provides peptides and other small molecules derived from regions of intracellular interacting proteins and methods for identification of such molecules. More specifically, the present invention provides peptides and other small molecules derived from regions of Gβ proteins which function as agonists or antagonists of adenylyl cyclase or phospholipase C-β2. The invention is based, at least in part, on the discovery of the inventors that it is possible to resolve, within a given intracellular signal transduction protein, a signal transfer region from a general binding domain. Such resolution provides a rational basis for design of agonists and antagonists of virtually any desired intracellular protein-protein interaction. The drug design methods of the invention utilize three-dimensional structural information for prediction of protein-protein interactions followed by evaluation of predictions in functional assays.

The present invention relates generally to the field of peptides and peptide mimetics as pharmaceutical and/or therapeutic agents. More particularly, the present invention relates to peptides and other small molecules (e.g. peptide mimetics) derived from regions of Gβ proteins and their use as pharmaceutical and/or therapeutic agents. For example, peptides and derivatives thereof for modulating adenylyl cyclase and phospholipase C-β2 activities are provided. Still further, methods for identification of peptides and derivatives thereof useful for modulating a chosen effector-of-interest among various effectors are provided. One advantage of the methods of the invention is the use of structural modeling information to predict and validate pharmacologic and therapeutic agents.

Predictions about effector interactions of Gβ proteins have been made using a combination of molecular modeling and experimental validation in which the predictions of the model are tested. Through an iterative process involving cycles of structural modeling followed by experimental testing, precise definition of individual effector domains within a Gβ signaling protein has been achieved. This validated procedure has general applicability for drug design targeted at other intracellular protein-protein interactions in virtually any intracellular signal transduction pathway.

This invention provides an isolated Gβ peptide or derivative thereof. This invention provides a peptide having an amino acid sequence selected from the group consisting of SEQ ID NO:5, SEQ ID NO:6, SEQ ID NO:7, SEQ ID NO:8, SEQ ID NO:9 and SEQ ID NO:10. In one embodiment, a derivative of a peptide is capable of immunospecific binding to an antipeptide antibody. In a preferred embodiment, a peptide or a derivative thereof displays only one functional activity of an intracellular signaling protein from which it is derived. This invention provides a purified fragment of a peptide, which fragment displays one or more functional activities of an intracellular signaling protein. This invention provides a purified fragment of a peptide comprising a region of the peptide selected from the group consisting of an adenylyl cyclase interaction region and a phospholipase C interaction region. This invention provides a purified molecule comprising the fragment. This invention provides a chimeric peptide comprising the fragment, which fragment consists of at least 6 amino acids fused by a covalent bond to an amino acid sequence of a second peptide.

This invention provides a purified antibody or an antigen-binding derivative thereof capable of immunospecific binding to a peptide selected from the group consisting of SEQ ID NO:5, SEQ ID NO:6, SEQ ID NO:7, SEQ ID NO:8, SEQ ID NO:9 and SEQ ID NO:10 and not to a protein from which the peptide was derived. In one embodiment, the antibody is polyclonal. In another embodiment, the antibody is monoclonal.

This invention provides a method of making a recombinant protein comprising: (a) growing a recombinant cell containing a nucleic acid comprising a nucleotide sequence encoding an amino acid sequence selected from the group consisting of SEQ ID NO:5, SEQ ID NO:6, SEQ ID NO:7, SEQ ID NO:8, SEQ ID NO:9 and SEQ ID NO:10 such that the recombinant protein is expressed by the cell; and (b) recovering the expressed recombinant protein. Further, this invention provides a purified recombinant protein produced by said method. Any method known in the art may be used for growing the recombinant cell (see e.g. Freshney, 1994, Culture of animal cells, A manual of basic technique, 3d ed., Wiley-Liss, Inc., New York). Any method known in the art may be used for recovering the recombinant protein, such as routine size exclusion chromatography, molecular tagging with histidine and purification on a nickel column, etc.

This invention provides a pharmaceutical composition comprising: (a) a peptide or derivative thereof selected from the group consisting of SEQ ID NO:5, SEQ ID NO:6, SEQ ID NO:7, SEQ ID NO:8, SEQ ID NO:9 and SEQ ID NO:10; and (b) a pharmaceutically acceptable carrier. The pharmaceutically acceptable carrier can be any carrier known to one skilled in the art.

This invention provides a method of identifying a peptide or derivative thereof having a biological activity of interest comprising: (a) providing a molecular model of an intracellular protein-protein interaction, which model predicts one or more interaction surfaces among a plurality of interacting proteins from three-dimensional structure information; and (b) testing a candidate interaction surface predicted by the molecular model by determining whether a peptide encoding at least a portion of the surface has a functional activity in a functional assay. In one embodiment, the functional activity is an agonist activity. In another embodiment, the functional activity is an antagonist activity.

This invention provides a method of identifying a functional activity of a Gβ peptide comprising: (a) expressing a protein comprising a peptide selected from the group consisting of SEQ ID NO:9 and SEQ ID NO:10 in a biological system; and (b) measuring an effect of expression in a biological assay. In one embodiment, the biological system is selected from the group consisting of an animal cell culture and an experimental animal. In another embodiment, the experimental animal is selected from the group consisting of a fly (e.g. *D. melanogaster*), a worm (e.g. *C. elegans*), a fish (e.g. zebrafish), a rat, a mouse and a guinea pig. In yet another embodiment, the biological assay is selected from the group consisting of an adenylyl cyclase assay, a phospholipase C assay, a potassium channel assay, a calcium channel assay and a β-adrenergic receptor kinase assay.

This invention provides a method of detecting an effect of expression of a recombinant protein comprising a peptide selected from the group consisting of SEQ ID NO:9 and SEQ ID NO:10 on a signal transduction pathway, the method comprising: (a) expressing the recombinant protein in a cell culture or experimental animal already having a mutation in the signal transduction pathway; and (b) detecting the effect of expression in a biological assay. In one embodiment, the biological assay is selected from the group consisting of an adenylyl cyclase assay, a phospholipase Cβ assay, a potassium channel assay and a calcium channel assay. In another embodiment, the mutation in the signal transduction pathway is in a gene selected from the group consisting of an adenylyl cyclase gene, a phospholipase C gene, a potassium channel gene and a calcium channel gene.

This invention provides a method of identifying a molecule that specifically binds to a peptide or derivative thereof selected from the group consisting of SEQ ID NO:5, SEQ ID NO:6, SEQ ID NO:7, SEQ ID NO:8, SEQ ID NO:9 and SEQ ID NO:10, the method comprising: (a) contacting the peptide or derivative thereof with a plurality of molecules under conditions conducive to binding; and (b) identifying a molecule from the plurality of molecules that specifically binds to the peptide or derivative thereof.

4. BRIEF DESCRIPTION OF THE DRAWINGS

The file of this patent contains at least one drawing executed in color. Copies of this patent with color drawings will be provided by the Patent and Trademark Office upon request and payment of the necessary fee.

Figure 1B:
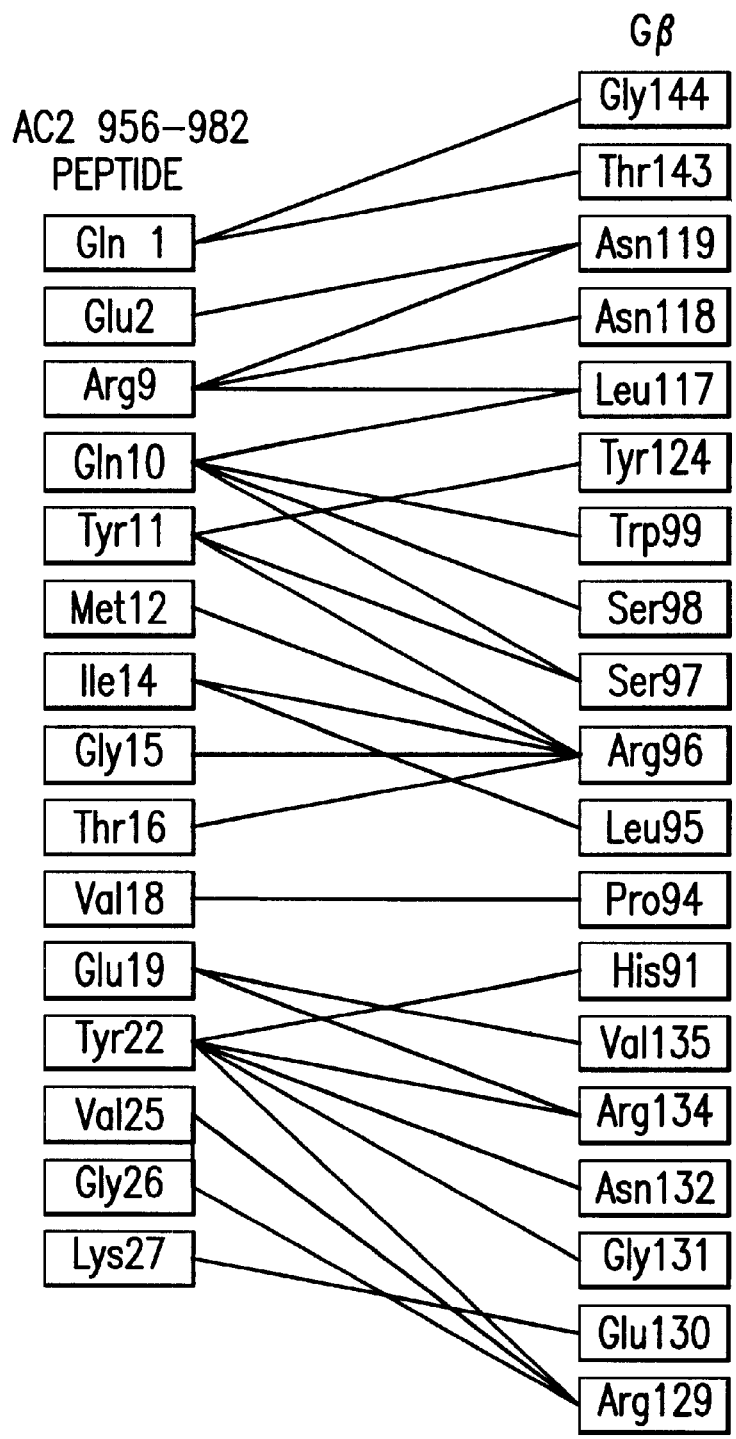

FIGS. 1A and 1B. Regions of Gβ involved in contacts with the AC2 956–982 peptide. (FIG. 1A) Ribbon diagram of the Gβ backbone from the crystal structure of Gβγ (Sondek et al., 1996, Nature 379, 369–374; Lambright et al., 1996, Nature 379, 311–319); the residues in contact with the AC2 peptide are shown in pink (Weng et al., 1996, J. Biol. Chem. 271, 26445–26448). (FIG. 1B) Predicted core contacts between the AC2 956–982 peptide and Gβ. The AC2 peptide residues are in the blue boxes. The AC2 peptide residues are numbered 1–27 from the N terminus. Gβ1 residues are in green boxes. The Gβ1 residues are shown in the spatial sequence in which they are predicted to interact with the AC2 peptide.

FIGS. 2A–2E. Effects of the Gβ86–105 peptides on AC2 and AC1 activities. (FIG. 2A) Ribbon diagram of the Gβ backbone with residues 86–105 in yellow. Other residues in contact with the AC2 peptide are shown in pink. (FIG. 2B) Effect of the Gβ86–105 peptide (TTN) and the M101N Gβ86–105 mutant peptide (m-TTN) on basal, $\alpha_s^*$ (2 nM), and various concentrations of TTN peptide on Gβγ-stimulated AC2 activity in the presence of $\alpha_s^*$ (2 nM) plus Gβγ (50 nM) stimulated AC2 activities. (FIG. 2C) Effect of various concentrations of TTN peptide on Gβγ-stimulated AC2 activity in the presence of $\alpha_s^*$ (2 nM). (FIG. 2D) Effect of TTN and m-TTN peptides on basal and CaM (100 nM) plus Gβγ (30 nM) regulated AC1 activities. (FIG. 2E) Effect of TTN and m-TTN peptides on basal and CaM (100 nM) stimulated AC1 activities.

Figure 3A:
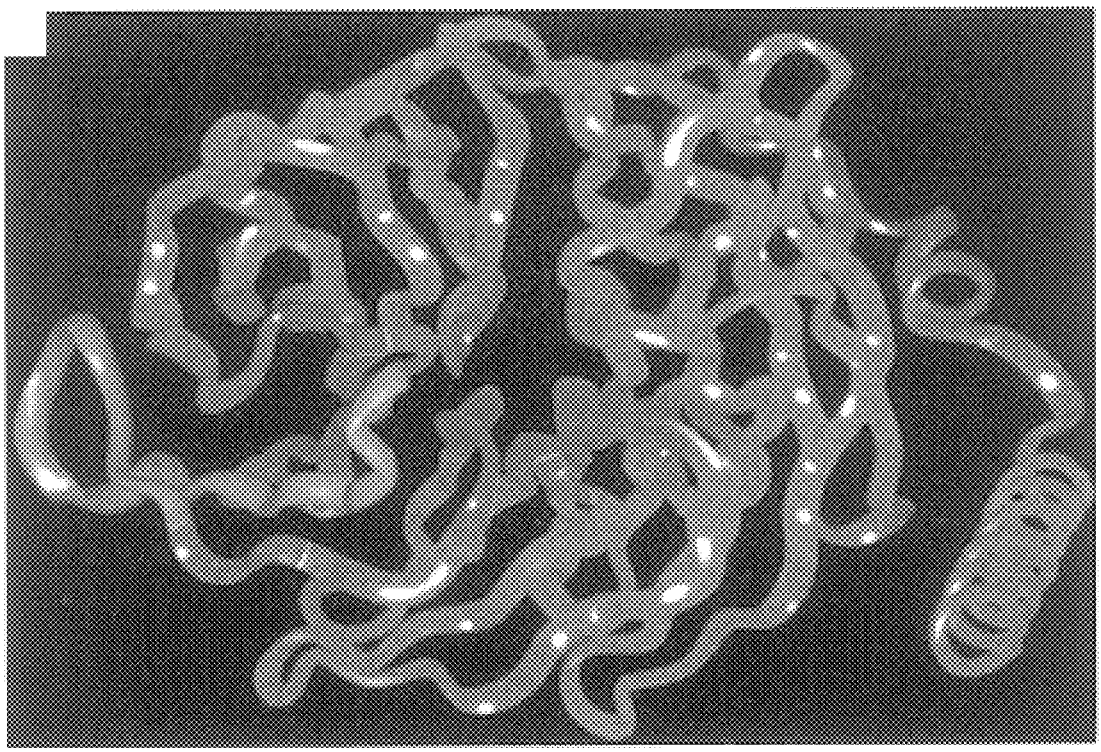
Figure 3B:
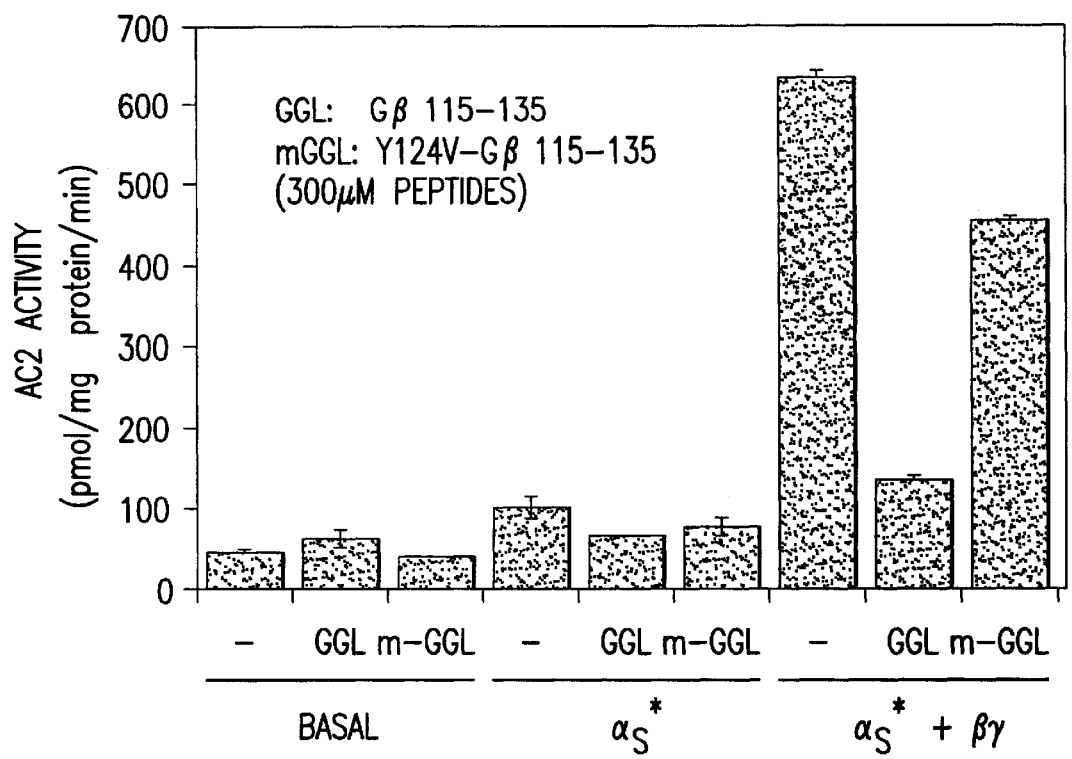
Figure 3C:
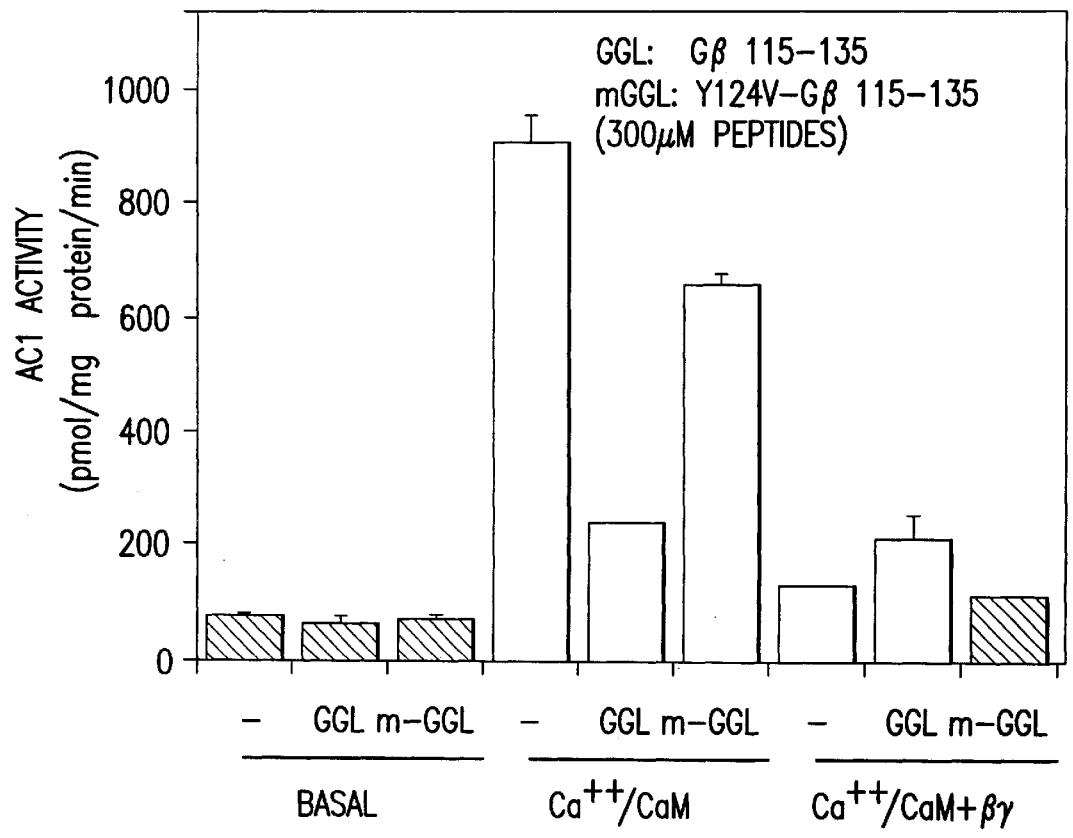

FIGS. 3A–3C. Effects of the Gβ115–135 peptide on AC2 and AC1 activities. (FIG. 3A) Ribbon diagram of the Gβ1 backbone with residues 115–135 in yellow. Other residues in contact with the AC2 peptide are shown in pink. (FIG. 3B) Effect of the Gβ115–135 peptide (GGL) and the Y124V Gβ115–135 mutant peptide (m-GGL) on basal, $\alpha_s^*$ (2 nM), and $\alpha_s^*$ (2 NM) plus Gβγ (50 nM) stimulated AC2 activities. (FIG. 3C) Effect of GGL and m-GGL peptides on basal, CaM (100 nM), or CaM (100 nM) plus Gβγ (30 nM) regulated AC1 activities.

Figure 4:
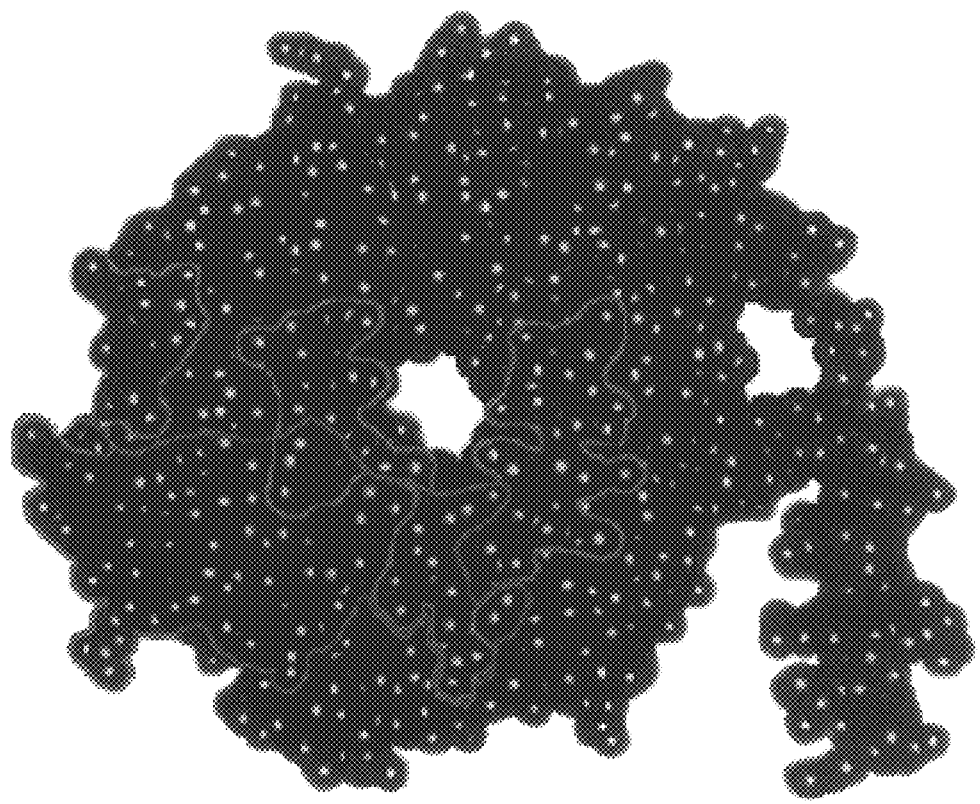

FIG. 4. Schematic representation of the regions of Gβ involved in interactions with Gα (outlined in green) and some regions that may interact with adenylyl cyclases 1 and 2 (outlined in red). The space-filling model of Gβ was obtained from the crystallographic coordinates; Gα contact regions are those identified by Sigler and coworkers (Sondek et al., 1996, Nature 379, 369–374; Lambright et al., 1996, Nature 379, 311–319) from the crystal structure of the heterotrimer. The AC2 peptide interaction region was deduced from molecular modeling studies (Weng et al., 1996, J. Biol. Chem. 271, 26445–26448) and the functional data in FIG. 2 and FIG. 3 indicate that these regions may be involved in interactions with AC1 and AC2.

Figure 5A:
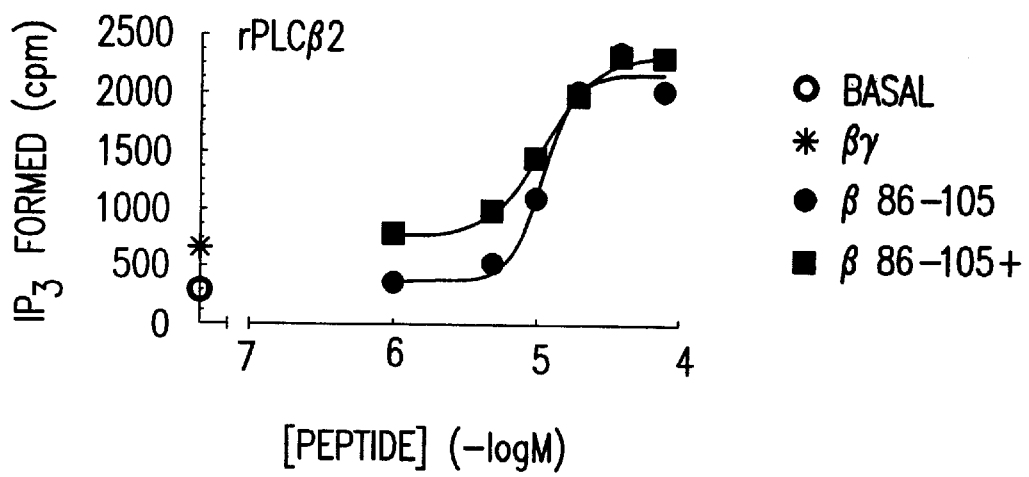
Figure 5B:
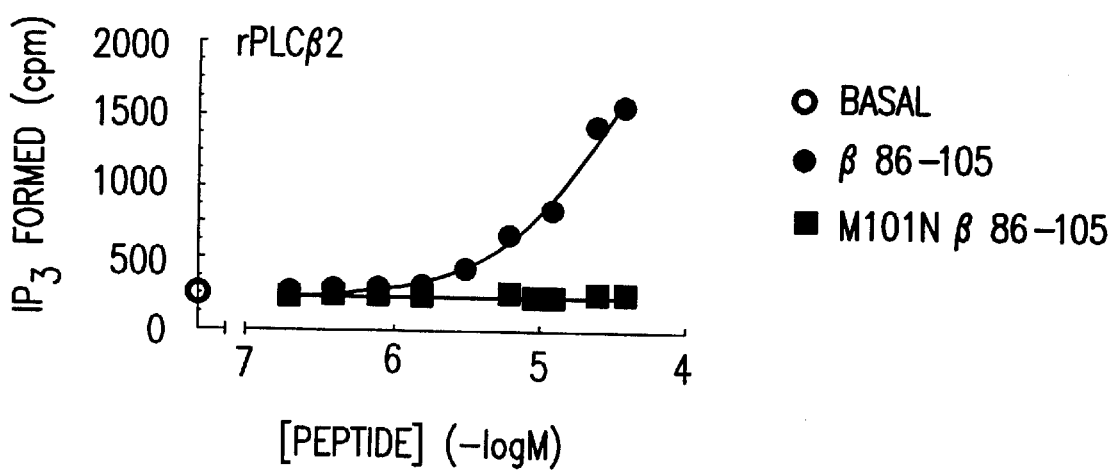
Figure 5C:
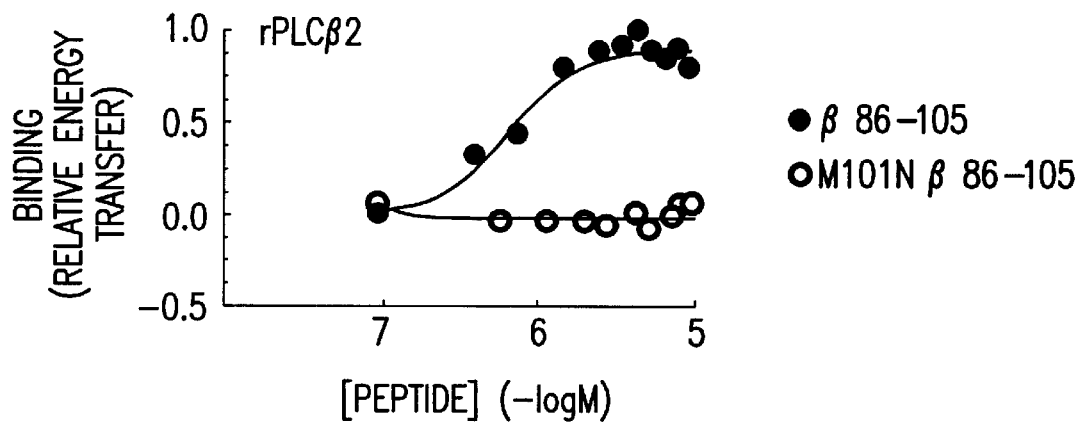

FIGS. 5A–C. Effects of varying concentrations of Gβ86–105 peptide on PLC-β2 activity. FIG. 5A: Effects of Gβ86–105 peptide on basal and Gβγ (100 nM) stimulated PLC-β2 activity. FIGS. 5B–C: Effects of Gβ86–105 peptide and M101N Gβ86–105 peptide on PLC-β2 activity.

FIGS. 6A–G. Effects of varying concentrations of Gβ86–105 peptide and (FIGS. 6A–C) K89A, H91A, and R96A substituted peptides on PLC-β2 activity (FIGS. 6D–E) K89A, H91A, and R96A triple substituted peptide on basal (FIG. 6D) and Gβγ (100 nM) (FIG. 6E) stimulated PLC-β2 activity. (FIG. 6F) Effects of varying concentrations of Gβ86–105 peptide and FLLT peptide on PLC-β2 activity. (FIG. 6G) Effects of 100 nM Gβγ and varying concentrations of Gβ86–105 peptide on PLC-β2 and PLCXβ activity.

Figure 7A:
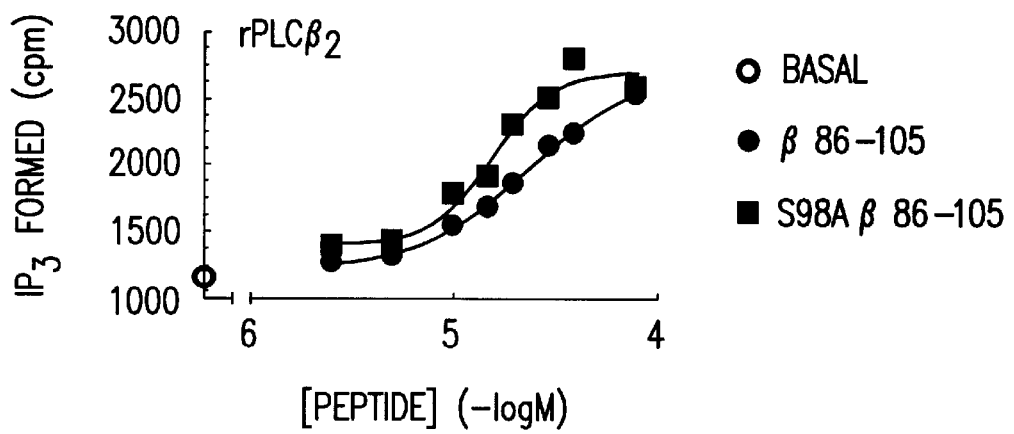
Figure 7B:
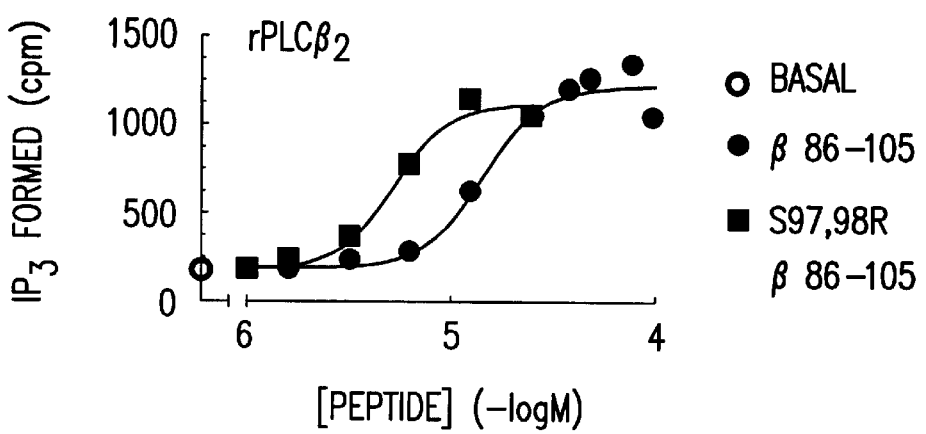
Figure 7C:
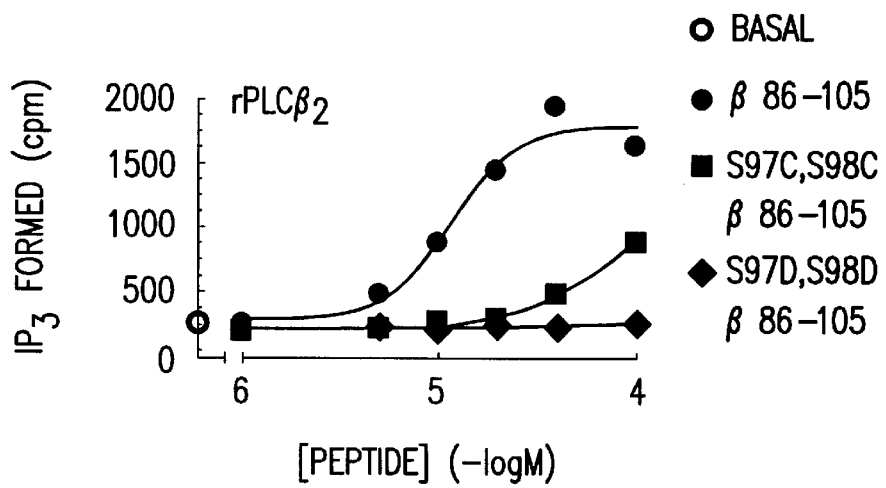

FIGS. 7A–C. Effects of varying concentrations of Gβ86–105 peptide and (FIG. 7A) S98A Gβ86–105 peptide, (FIG. 7B) S97,98R Gβ86–105 peptide, and (FIG. 7C) S97, 98D and S97, 98C peptides on PLC-β2 activity.

FIGS. 8A–8E. Effects of shorter peptides from Gβ86–105 region on PLC-β2 activity. (FIG. 8A) Effects of 100 μM Gβ96–98, Gβ96–101, and Gβ89–101 peptides on PLC-β2 activity. (FIGS. 8B–C) Effects of varying concentrations of Gβ96–101 peptide and S97, 98R (FIG. 8B) and S97, 98D (FIG. 8C) Gβ96–101 peptides on PLC-β2 basal activity. Values for (FIG. 8A) are given as mean±SEM of three experiments.

Figure 9A:
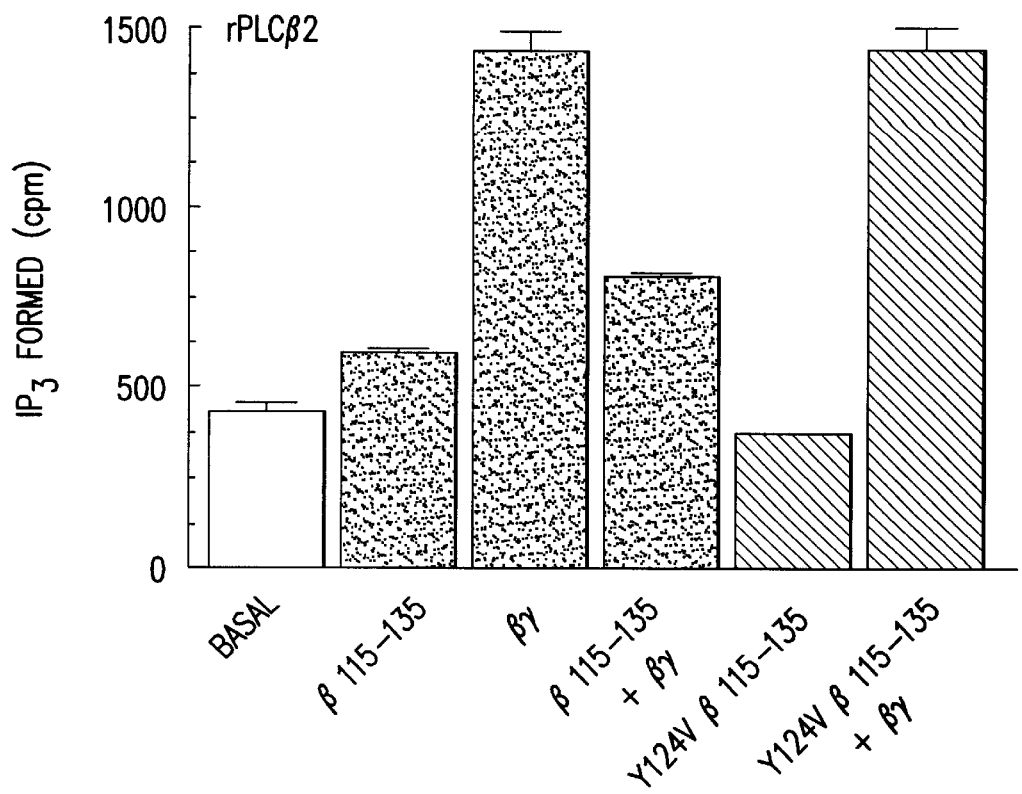
Figure 9B:
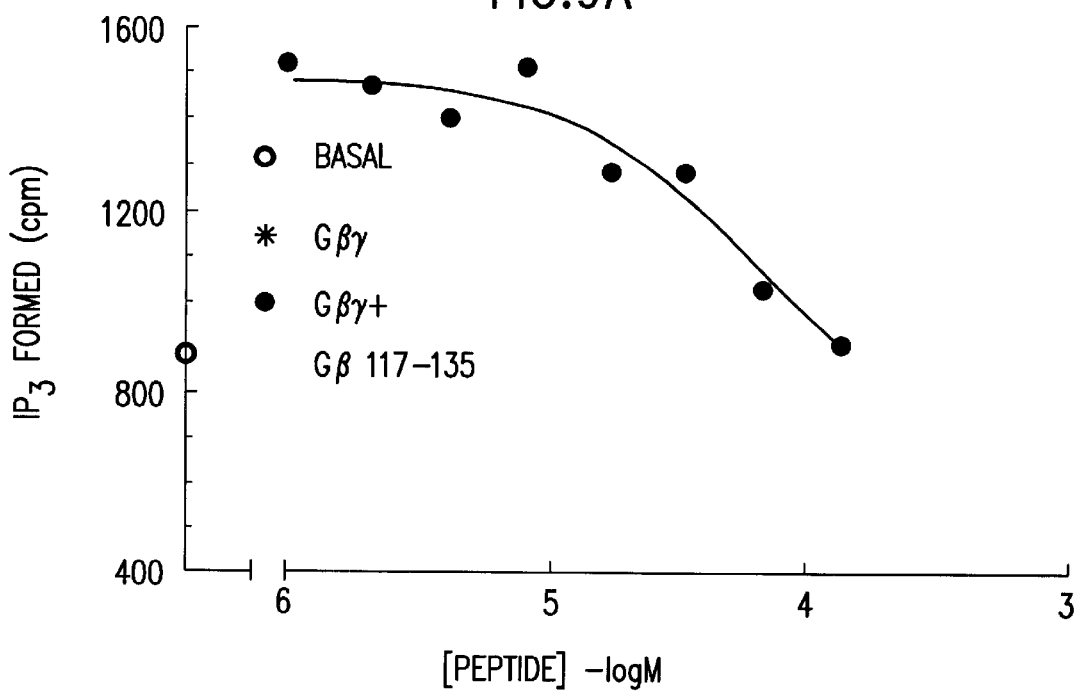

FIGS. 9A–B. Effects of Gβ115–135 peptide on PLC-β2 activity. (FIG. 9A) Effects of 30 nM Gβ115–135 peptide and Y124V Gβ115–135 peptide on basal and Gβγ (100 nM) stimulated PLC-β2 activity. (FIG. 9B) Effect of varying concentrations of Gβ115–135 peptide on Gβγ (100 nM) stimulated PLC-β2 activity. Values for (FIG. 9A) are given as mean±SEM of three experiments.

Figure 10:
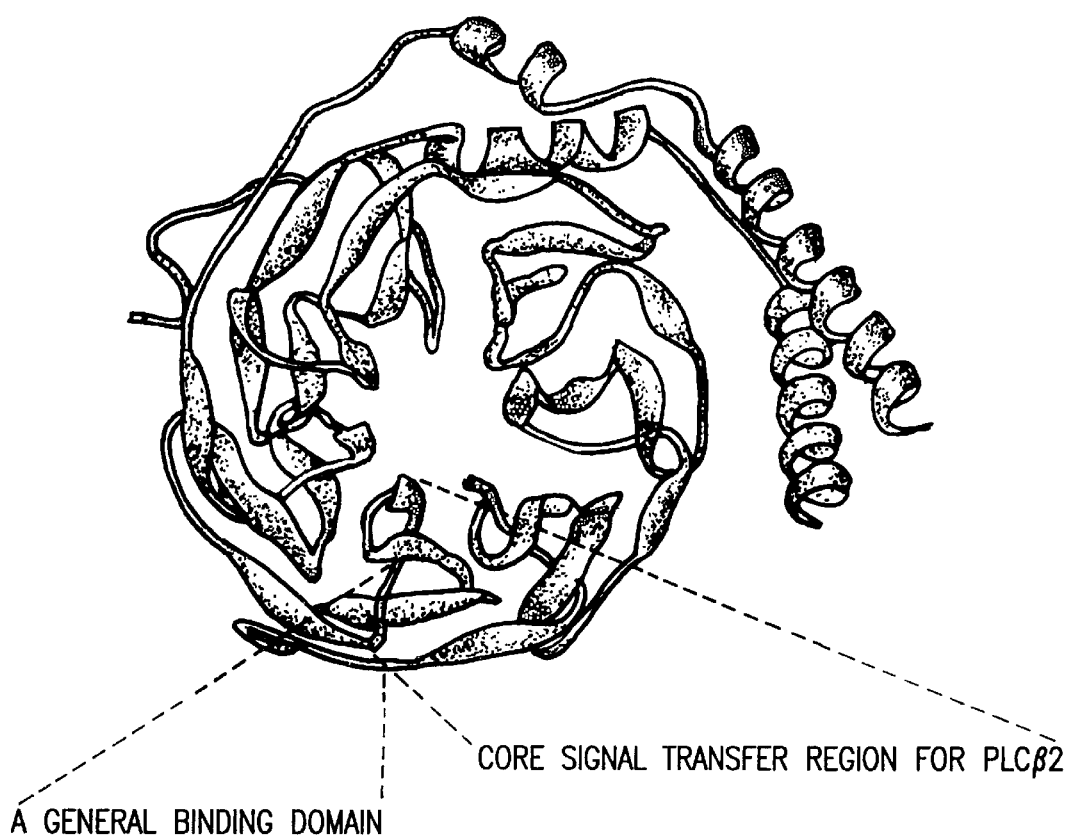

FIG. 10. Ribbon diagram of Gβγ.

5. DETAILED DESCRIPTION OF THE INVENTION

The present invention relates to peptides and other small molecules (e.g. peptide mimetics) derived from regions of intracellular interacting proteins (e.g. signal transduction proteins) and to their use as pharmaceutics. The present invention also relates to methods for identifying peptides and derivatives thereof as candidate pharmaceutics. Such methods combine molecular modeling of surface interactions between two or more intracellular proteins with experimental validation of model predictions. More specifically, modeling of surface interactions is based on three-dimensional structure information and validation of model predictions is based on measuring activities of peptides or derivatives thereof encoding at least a portion of a predicted interaction surface in a functional assay. The invention further relates to fragments and analogs of identified peptides. Nucleic acids encoding such peptides are also within the scope of the invention. Production of peptides and derivatives thereof, e.g., by recombinant or chemical synthetic methods, is provided. Antibodies specifically immunoreactive with identified peptides and derivatives are additionally provided.

The invention is illustrated by way of Examples set forth in Section 6 below which disclose, inter alia, the identification and characterization of peptides derived from a Gβ protein, human Gβ1, which have specific interactions with adenylyl cyclase and phospholipase C-β2. The complete Gβ1 protein amino acid sequence, which is identical in humans, dogs, cows and mice, is set forth in SEQ ID NO:1 (Codina et al., 1986, Beta-subunits of the human liver Gs/Gi signal-transducing proteins and those of bovine retinal rod cell transducing are identical, FEBS Lett. 207, 187–192).

Any functional assay known to one skilled in the art may be used to measure a functional activity of a peptide of the invention. For example, an adenylyl cyclase activity or a phospholipase C-β2 activity may be measured. Such enzyme activities may be measured in in vivo or in vitro experimental systems. Functional assays used to determine an activity of a peptide may employ any cloned, recombinant enzyme available. Many such enzymes are known in the art. Examples include but are not limited to: the bovine adenylyl cyclase 1 (AC1) amino acid sequence set forth in SEQ ID NO:2 (Krupinski et al., 1989, Science 244, 1558–1564; the rat adenylyl cyclase 2 (AC2) amino acid sequence is set forth in SEQ ID NO:3 (Feinstein et al., 1991, Proc. Natl. Acad. Sci. U.S.A. 88, 10173–10177); and the human phospholipase C-β2 (PLC-β2) amino acid sequence is set forth in SEQ ID NO:4 (Park et al., 1992, J. Biol. Chem. 267, 16048–16055).

In particular aspects, the invention provides amino acid sequences of peptides, fragments and derivatives thereof, and other small molecules, and fragments and derivatives thereof, which comprise an antigenic determinant (i.e., can be recognized by an antibody) or which are otherwise functionally active. In the case of peptides, nucleic acid sequences encoding them are also provided. "Functionally active" material as used herein refers to material displaying one or more functional activities associated with an identified peptide or other small molecule of the invention, e.g., activation or inhibition of a downstream effector (e.g., adenylyl cyclase 1 or 2, phospholipase C-β2, etc.) or binding to another protein binding partner, antigenicity (binding to an antibody of the invention), immunogenicity, etc.

In specific embodiments, the invention provides fragments of a peptide or derivative thereof consisting of at least 3 amino acids, 6 amino acids, 10 amino acids, 15 amino acids, 20 amino acids, 30 amino acids, or 50 amino acids. Nucleic acids encoding the foregoing are also provided.

Once a peptide of the invention is identified, it may be isolated and purified by any number of standard methods including but not limited to chromatography (e.g., ion exchange, affinity, and sizing column chromatography), centrifugation, differential solubility, etc. The functional properties of an identified peptide of interest may be evaluated using any functional assay known in the art. In preferred embodiments, assays for evaluating downstream effector functions in intracellular signal transduction pathways are used (see Examples in Section 6).

In other specific embodiments, a peptide, fragment, analog, or derivative may be expressed as a fusion, or chimeric protein product (comprising the peptide, fragment, analog, or derivative joined via a peptide bond to a heterologous protein sequence of a different protein). Such a chimeric product can be made by ligating the appropriate nucleic acid sequences encoding the desired amino acid sequences to each other by methods known in the art, in the proper reading frame, and expressing the chimeric product by methods known in the art. Such exemplary but not limiting methods are described below. Alternatively, a chimeric product may be made by protein synthetic techniques, e.g., by use of a peptide synthesizer. Standard chemical methods for peptide synthesis are also well known in the art (see e.g. Hunkapiller et al., 1984, Nature 310, 105–111). The terms "peptide", "polypeptide" and "protein" are used synonymously herein.

This invention provides methods for identification of peptides and peptide mimetics. In a preferred embodiment, the methods of the invention provide for identification of peptides (and/or fragments, analogs, derivatives, and mimetics thereof, i.e. other small molecules) by first modeling an interaction surface from three-dimensional structural information of one or more interacting proteins. In a preferred embodiment, interactions of a heterotrimeric G protein β subunit with one or more downstream effectors is modeled to predict one or more interaction regions. Predicted interaction regions are next evaluated using synthetic or recombinant peptides (or other small molecules) in functional assays. Through an iterative process which may involve, for example, changing one or more residues of a given peptide, the method can be used to identify peptides having very specific functional effects. For example, peptide agonists or antagonists of a specific pathway are identified by activation or inhibition, respectively, of the functional pathway with a given peptide or derivative thereof. For an intracellular protein having more than one interaction partner, interaction regions specific for each interaction partner may be identified. In a preferred embodiment, the methods of the invention are used to resolve a specific signal transfer region from a general binding domain within an intracellular signaling protein. Such resolution permits design of selective agonists and antagonists of the identified interactions.

5.1. Peptides Derived from Regions of Gβ Proteins

The peptides of the invention described herein which have been derived from regions of Gβ proteins include but are not limited to peptides having amino acid sequences as set forth in SEQ ID NO:5, SEQ ID NO:6, SEQ ID NO:7, SEQ ID NO:8, SEQ ID NO:9 and SEQ ID NO:10.

5.1.1. Adenylyl Cyclase Effector Pathway

Peptides which modulate the adenylyl cyclase effector pathway include but are not limited to peptides having amino acid sequences as set forth in SEQ ID NO:5 and SEQ ID NO:6.

5.1.2. Phospholipase C Effector Pathway

Peptides which modulate the phospholipase C effector pathway include but are not limited to peptides having amino acid sequences as set forth in SEQ ID NO:9 and SEQ ID NO:10.

5.1.3. Other Effector Pathways

The methods of the invention may be applied to virtually any intracellular signal transduction pathway. For example, many cancers have been linked to perturbations in regulation of the cell cycle. Cell cycle gene products are amenable to the methods of the invention for identification of peptides and other small molecules which may act as agonists or antagonists. Such molecules are of potentially great benefit for cancer treatment.

Briefly, the cell cycle consists of four stages: G1 (for Gap1) phase, the resting stage prior to DNA synthesis; S (for synthesis) phase, in which DNA synthesis occurs; G2 (for Gap2) phase, the resting stage after DNA synthesis and prior to mitosis; and M phase, mitosis, in which cell division occurs. For a review of the cell cycle, including a list of genes encoding intracellular interacting proteins of the cell cycle, see Murray and Hunt ("The Cell Cycle, An Introduction", 1993, Oxford University Press, New York, pp. 1–251, incorporated by reference herein in its entirety).

Progression of a cell through the cell cycle is driven by a group of cyclin-dependent kinases (CDKs) (see e.g. Elledge, 1996, Science 274, 1664–1672; Nasmyth, 1996, Science 274, 1643–1645). The kinase activities of CDKs require their positive subunits, the cyclins. Further, the activities of specific CDK/cyclin complexes are in turn positively and negatively regulated by phosphorylation events and CDK inhibitors (CKIs) (see Hunter and Pines, 1995, Cell 80, 225–236; Morgan, 1995, Nature 374, 131–134). While specific CDKs (CDK2, CDK4 and CDK6) and cyclins D and E regulate the progression from G1 into S phase, cdc2 and cyclins A and B regulate the cell cycle progression from G1 into mitosis (see Hunter and Pines, 1995, Cell 80, 225–236).

Human tumor suppressor genes often act as negative regulators of the cell cycle, and several tumor suppressors are known to influence activities of CDK/cyclin complexes. For example, p53 activates transcription of the p21 CDK inhibitor (p21$^{WAF1/CIP1}$) in response to DNA damage signals, and p21 in turn binds and inactivates the CDK4 and CDK6 cyclin D complexes (Gartel et al., 1996, Proc. Soc. Exp. Biol. Med. 213, 138–149). Another CDK inhibitor, p16, is itself a potent tumor suppressor (Biggs and Kraft, 1995, J. Mol. Med. 73, 509–514).

By systematically applying the methods of the invention to intracellular protein-protein interactors such as the cyclins and CDKs, it is possible to identify peptides and derivatives thereof having functional activity in disease states such as cancer. In this way, application of the methods of the invention may identify important pharmacologic and therapeutic cancer drugs.

5.2. Troubleshooting

If any given signal transduction protein or pathway is initially resistant to the above-described approaches for identifying peptides and other small molecules therefrom for use as pharmaceutics, the following troubleshooting discussion may be helpful. A resistant intracellular signal transduction protein may be indicated by the identification of no peptide or other small molecule capable of modulating a downstream effector in a specific fashion. Consider a case where an initial molecular model of a given effector interaction does not identify a peptide or other small molecule when tested experimentally using functional assays for cyclins, CDKs, or such as those described in the Examples set forth in Section 6. In this instance, careful attention should be paid to refining the molecular model.

For example, a synergistic effect between two or more domains of a given signal transduction protein, or two or more domains of more than one signal transduction protein, may be required to elicit an experimental manifestation of an effector interaction using a peptide or derivative thereof of the invention. In this instance, it is desirable to identify and enumerate in a systematic fashion any and all protein-protein interaction domains which may have an influence in the downstream effector pathway. In this way, an accounting is made for the possibility of multiple molecular determinants in any given effector pathway.

In this regard, a current review of the literature is often warranted in an effort to determine whether all possible signal transduction proteins (and other biologic signaling agents) have been considered in the design of prospective peptides and peptide mimetics to be experimentally evaluated. This is particularly so in the present post-genomic era where vast catalogs of genes encoding predicted proteins having known or predicted functions are publicly available in computer databases.

An effective literature review generally involves reviewing the relevant chemical, biological, and medical literature (including clinical data) in connection with a signal transduction pathway or other biological event of interest. In this regard, reference to a variety of frequently-updated computer databases is often the best course to follow (e.g. Medline®, GenBank®, etc.).

5.3. Methods of Use with the Invention

Any method known to one of ordinary skill in the art may be used together with the peptides, derivatives, and methods of the invention. Set forth below are well known methods for nucleic acid cloning, hybridization, and amplification which are of general use together with the invention. These methods enable the production of, e.g., synthetic and recombinant peptides and derivatives thereof, including fusion proteins.

5.3.1. Nucleic Acid Cloning Methods

Methods for cloning nucleic acids are very well known in the art. Several examples of use with the invention are set forth below. These methods shall not be construed to limit the invention in any way. The following description sets forth methods by which clones of any desired nucleic acid may be obtained.

Any prokaryotic or eukaryotic cell may serve as the nucleic acid source for molecular cloning. For example, the nucleic acid sequences encoding proteins and fragments thereof may be isolated from vertebrate, mammalian, human, porcine, bovine, feline, avian, equine, canine, as well as additional primate sources, insects (e.g., Drosophila), invertebrates (e.g., C. elegans), plants, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell (see e.g., Sambrook et al., 1989, Molecular Cloning, A Laboratory Manual, 2d Ed., Cold Spring Harbor Laboratory Press, Cold Spring Harbor, N.Y.; see also Glover, ed., 1985, DNA Cloning: A Practical Approach, MRL Press, Ltd., Oxford, U.K. Vol. I, II.). Clones derived from genomic DNA may contain regulatory and intron DNA regions in addition to coding regions; clones derived from cDNA will contain only exon sequences.

Once nucleic acid fragments are generated, identification of the specific nucleic acid fragment of interest may be accomplished in a number of ways. For example, if a portion of a nucleic acid is available and can be purified and labeled, the generated nucleic acid fragments may be screened by hybridization to the labeled probe (Benton and Davis, 1977, Science 196, 180; Grunstein and Hogness, 1975, Proc. Natl. Acad. Sci. U.S.A. 72, 3961). Those fragments with substantial homology to the probe will hybridize. It is also possible to identify the appropriate fragment by restriction enzyme digestion(s) and comparison of fragment sizes with those expected according to a known restriction map if such is available.

Alternatively, the presence of the desired nucleic acid may be detected by assays based on the physical, chemical, or immunological properties of any expressed product. For example, cDNA clones, or DNA clones which hybrid-select the cognate mRNAs, can be selected and expressed to produce a protein that has, e.g., similar or identical electrophoretic migration, isoelectric focusing behavior, proteolytic digestion maps, hormonal activity, binding activity, or antigenic properties as known for a protein of interest. Using an antibody to a known protein, other proteins may be identified by binding of the labeled antibody to expressed putative proteins, e.g., in an ELISA (enzyme-linked immunosorbent assay)-type procedure. Further, using a binding protein specific to a known protein, other proteins may be identified by binding to such a protein (see e.g., Clemmons, 1993, "IGF binding proteins and their functions," Mol. Reprod. Dev. 35, 368–374; Loddick et al., 1998, "Displacement of growth factors from their binding proteins as a potential treatment for stroke," Proc. Natl. Acad. Sci. U.S.A. 95, 1894–1898).

An identified and isolated nucleic acid may be inserted into an appropriate cloning vector. Any of a large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives or the Bluescript vector (Stratagene). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and an gene may be modified by homopolymeric tailing. Recombinant molecules can be introduced into host cells via transformation, transfection, infection, electroporation, etc., so that many copies of the desired sequence are generated.

In specific embodiments, transformation of host cells with recombinant DNA molecules that incorporate an isolated nucleic acid sequence enables generation of multiple copies of the nucleic acid. Thus, the nucleic acid may be obtained in large quantities by growing transformants, isolating the recombinant DNA molecules from the transformants and, when necessary, retrieving the inserted nucleic acid from the isolated recombinant DNA (e.g. by restriction digestion or PCR).

5.3.2. Nucleic Acid Hybridization

Nucleic acid hybridization under various stringency conditions (e.g. low, moderate, or high stringency conditions) is quite well known to one skilled in the art. Guidelines for nucleic acid hybridization are widely available, including detailed protocols for determination and use of an appropriate stringency (see e.g., Sambrook et al., 1989, Molecular Cloning, A Laboratory Manual, 2d ed., Cold Spring Harbor Laboratory Press, Cold Spring Harbor, N.Y.; see also, Ausubel et al., eds., in the Current Protocols in Molecular Biology series of laboratory technique manuals, © 1987–1994 Current Protocols, © 1994–1997 John Wiley and Sons, Inc.; see especially, Dyson, 1991, Immobilization of nucleic acids and hybridization analysis, In: Essential Molecular Biology: A Practical Approach, Vol. 2, Brown, ed., pp. 111–156, IRL Press at Oxford University Press, Oxford, U.K.).

In one embodiment, a nucleic acid which is hybridizable to another nucleic acid under conditions of high stringency is provided. In another embodiment, a nucleic acid which is hybridizable to another nucleic acid under conditions of medium stringency is provided. By way of example and not limitation, hybridization procedures using conditions of high stringency may be as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography.

In yet another embodiment, a nucleic acid which is hybridizable to another nucleic acid under conditions of low stringency is provided. Again by way of example and not limitation, procedures using conditions of low stringency may be as follows (see also Shilo and Weinberg, 1981, Proc. Natl. Acad. Sci. U.S.A. 78, 6789–6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and re-exposed to film.

5.3.3. Nucleic Acid Amplification

The polymerase chain reaction (PCR) may be used in connection with the invention to amplify any desired sequence from any given source (e.g., a cultured cell, a tissue sample, a genomic library, a cDNA library, a purified plasmid, a purified phagemid, etc.). Oligonucleotide primers representing known sequences are used as primers in PCR. PCR may be carried out using a thermal cycler (e.g., from Perkin-Elmer Cetus) and a thermostable polymerase (e.g., Gene Amp™ brand of Taq polymerase). The nucleic acid being amplified may include but is not limited to mRNA, cDNA or genomic DNA from any species. The PCR amplification method is quite well known in the art (see e.g., U.S. Pat. Nos. 4,683,202, 4,683,195 and 4,889,818; Gyllenstein et al., 1988, Proc. Natl. Acad. Sci. U.S.A. 85, 7652–7656; Ochman et al., 1988, Genetics 120, 621–623; Loh et al., 1989, Science 243, 217–220).

The rolling circle amplification (RCA) method may also be used for nucleic acid amplification. One such method utilizing rolling circle replication by DNA polymerase under isothermal conditions has recently been described by Lizardi et al. (1998, Nature Genetics 19, 225–232; see also references therein).

Any prokaryotic cell, eukaryotic cell, or virus, can serve as the nucleic acid source. For example, nucleic acid sequences may be obtained from the following sources: human, porcine, bovine, feline, avian, equine, canine, insect (e.g., *D. melanogaster*), invertebrate (e.g., *C. elegans*), plant, etc. The DNA may be obtained by standard procedures known in the art (see e.g., Sambrook et al., 1989, Molecular Cloning, A Laboratory Manual, 2d Ed., Cold Spring Harbor Laboratory Press, Cold Spring Harbor, N.Y.; Glover (ed.), 1985, DNA Cloning: A Practical Approach, MRL Press, Ltd., Oxford, U.K. Vol. I, II).

5.4. Diseases, Disorders and Conditions

Various diseases, disorders and conditions to which peptides, peptide derivatives, other small molecules, and methods of the invention may be applied include but are not limited to the following examples. Disease states include acquired immunodeficiency syndrome (AIDS), angina, arteriosclerosis, arthritis, asthma, blood pressure dysregulation, bronchitis, cancer (all forms), cholesterol imbalance, cerebral circulatory, cirrhosis, clotting disorder, depression, dermatologic disease, diabetes, diarrhea, dysmenorrhea, dyspepsia, emphysema, gastrointestinal distress, hemorrhoids, hepatitis, hypertension, hyperprolactinemia, immunomodulation, resistance to bacterial infection, resistance to viral infection, inflammation, insomnia, lactation disorders, lipidemia, migraine, pain prevention or management, peripheral vascular disease, platelet aggregation, premenstrual syndrome, prostatic disorders, elevated triglycerides, respiratory tract infection, retinopathy, sinusitis, rheumatic disease, impaired wound healing, tinnitus, urinary tract infection and venous insufficiency.

Other indications include cardiovascular disorders, nervous system disorders, hypercholesterolemia, inflammation, antipyretic, analgesic, slowing the aging process, accelerated convalescence, anemia, indigestion, impotence and menstrual disorders.

5.5. Pharmaceutical Compositions

The methods of the present invention comprise administering to a subject in need thereof an effective amount of a peptide or derivative thereof (e.g. a small molecule mimetic), or a composition comprising a peptide or peptide derivative, to the subject to modulate (i.e. stimulate or inhibit) an intracellular protein-protein interaction, such as a signal transduction event. In one embodiment, an effective amount of a therapeutic composition comprising a peptide or derivative thereof and a pharmaceutical carrier is administered systemically to a subject to modulate a signal transduction event or to treat a disease, disorder or condition. In another embodiment, an effective amount of a therapeutic composition comprising a peptide or derivative thereof and a pharmaceutical carrier is applied locally to a site to modulate signal transduction or to treat a disease, disorder or condition at the site.

The peptides and derivatives thereof and pharmaceutical compositions of the present invention are used in the treatment of or amelioration of symptoms in any disease, condition or disorder where modulation of a signal transduction event would be beneficial. Non-limiting examples of diseases, disorders or conditions in which the peptides, peptide derivatives and pharmaceutical compositions of the present invention can be used for treatment are set forth in Section 5.4 herein.

The methods of the present invention also provide for the treatment of a subject by administration of a therapeutic composition comprising a peptide or derivative thereof and a pharmaceutically acceptable carrier. The subject is preferably an animal, including but not limited to animals such as dogs, cats, cows, sheep, pigs, chickens, etc., is preferably a mammal, and most preferably a human.

Various delivery systems are known and can be used to administer a peptide or derivative thereof or a pharmaceutical composition of the invention. For example, a pharmaceutical composition of the invention can be administered systemically by, e.g., intravenous or intramuscular injection. In another example, a pharmaceutical composition of the invention can be introduced to a site by any suitable route including sub-cutaneously, orally, topically, subconjunctivally, etc. In yet another example, a pharmaceutical composition of the invention can be introduced into the central nervous system by any suitable route, including intraventricular or intrathecal injection, etc. Intraventricular injection may be facilitated by an intraventricular catheter, for example, attached to a reservoir, such as an Ommaya reservoir. For veterinary or other purposes the composition may be administered intraperitoneally.

Further, delivery systems are well known and can be used to administer a pharmaceutical composition of the invention, e.g., via aqueous solution, encapsulation in liposomes, microparticles, microcapsules, and by way of receptor-mediated endocytosis (see e.g., Wu and Wu, 1987, J. Biol. Chem. 262, 4429–4432). Other methods of administration include but are not limited to direct application to the skin, intradermal, intranasal and epidural routes. A pharmaceutical composition of the invention may be administered by any convenient route, for example, by infusion or bolus injection, by absorption through epithelial or mucocutaneous linings (e.g., oral mucosa, rectal and intestinal mucosa). In a preferred embodiment, intravenous administration is used.

In a specific embodiment, a therapeutic or pharmaceutical composition of the invention is administered locally to the area in need of treatment. This may be achieved by, for example and not by way of limitation, local infusion during surgery, topical application (e.g. cream or ointment), in conjunction with a wound dressing after surgery, or directly onto the eye, by injection, by means of a catheter, or by means of an implant, said implant being of a porous or gelatinous material, including membranes, such as silastic membranes, or fibers. In one embodiment, administration can be by direct injection at the site of treatment. In another embodiment, a therapeutic or pharmaceutical composition can be administered to the eye by eye drops.

In yet another embodiment, a therapeutic or pharmaceutical composition can be delivered in a vesicle, in particular, a liposome (see Langer, 1990, Science 249, 1527–1533; Treat et al., 1989, in Liposomes In The Therapy Of Infectious Disease And Cancer, Lopez-Berestein and Fidler, eds., Liss, New York, pp. 353–365; Lopez-Berestein, ibid., pp. 317–327). A vesicle or liposome delivery system is particularly preferred for delivery of a peptide or other small molecule which does not easily cross cell membranes to reach an intracellular site of action.

In yet another embodiment, a therapeutic or pharmaceutical composition can be delivered in a controlled release system. In one embodiment, a pump may be used (see Langer, supra; Sefton, 1987, CRC Crit. Rev. Biomed. Eng. 14, 201; Buchwald et al., 1980, Surgery 88, 507; Saudek et al., 1989, N. Engl. J. Med. 321, 574). In another embodiment, polymeric materials can be used (see Medical Applications of Controlled Release, 1974, Langer and Wise, eds., CRC Press, Boca Raton, Fla.; Controlled Drug Bioavailability, Drug Product Design and Performance, 1984, Smolen and Ball, eds., Wiley, New York; Ranger and Peppas, 1983, J. Macromol. Sci. Rev. Macromol. Chem. 23, 61; see also Levy et al., 1985, Science 228, 190; During et al., 1989, Ann. Neurol. 25, 351; Howard et al., 1989, J. Neurosurg. 71, 105). In yet another embodiment, a controlled release system can be placed in proximity of the therapeutic target, i.e., the brain (see, e.g., Goodson, 1984, in Medical Applications of Controlled Release, supra, vol. 2, pp. 115–138).

The present invention also provides for therapeutic or pharmaceutical compositions comprising a peptide or a peptide derivative of the invention in combination with a pharmaceutically acceptable carrier, which compositions can be administered as described above. The term "carrier" refers to a diluent, adjuvant, excipient, or vehicle with which the peptide is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers, particularly for injectable solutions. Particularly preferred pharmaceutical carriers for treatment of or amelioration of inflammation in the central nervous system are carriers that can penetrate the blood/brain barrier.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The therapeutic composition, if desired, can also contain minor amounts of wetting or emulsifying agents, or pH buffering agents. These compositions can take the form of solutions, suspensions, emulsion, tablets, capsules, powders, sustained-release formulations, and the like. The composition can be formulated with traditional binders and carriers such as triglycerides. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the subject. The formulation should suit the mode of administration.

In a preferred embodiment, the composition is formulated in accordance with routine procedures as a pharmaceutical composition adapted for local injection administration to human beings. Typically, compositions for local injection administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the composition is administered by injection, an ampoule of sterile water for injection or saline can be provided so that the ingredients may be mixed prior to administration.

The therapeutic or pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The composition, if desired, can also contain minor amounts of wetting or emulsifying agents, or pH buffering agents. The composition can be a liquid solution, suspension, emulsion, tablet, pill, capsule, sustained release formulation, cream, gel or powder. The composition can be formulated as a suppository, with traditional binders and carriers such as triglycerides.

The present invention also provides for the modification of the peptide or peptide derivative such that it is more stable once administered to a subject (i.e., once administered, it has a longer period of effectiveness as compared to the unmodified form). Such modifications are well know to those of skill in the art (e.g., polyethylene glycol derivatization a.k.a. PEGylation, microencapsulation, etc.).

The amount of the therapeutic or pharmaceutical composition of the invention which is effective in the treatment of a particular disease, condition or disorder will depend on the nature of the disease, condition or disorder and can be determined by standard clinical techniques. In general, the dosage ranges from about 0.001 mg/kg to about 2 mg/kg. In addition, in vitro assays such as those set forth in the Examples of Section 6 herein may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems. For example, in order to obtain an effective mg/kg dose for humans based on data generated from rat studies, the effective mg/kg dosage in rats is divided by six.

The invention also provides a pharmaceutical pack or kit comprising one or more containers filled with one or more of the ingredients (e.g., peptide or small molecule derivative thereof plus carrier) of the pharmaceutical compositions of the invention. In another embodiment, the invention comprises kits containing an effective amount of a pharmaceutical composition of the invention. Thus, the kit is contemplated to comprise one or more containers containing at least one pharmaceutical composition of the invention. Simply by way of example, the kit will contain such a composition formulated for application to the skin, or for administration by intradermal, intramuscular, intravenous, intranasal, epidural and oral routes of administration. The kits may contain a liquid solution, suspension, emulsion, tablet, pill, capsule, sustained release formulation, cream, gel or powder.

5.6. Peptide Derivatives

Peptide derivatives (e.g. small molecule mimetics) may include cyclic peptides, peptides obtained by substitution of a natural amino acid residue by the corresponding D-stereoisomer or by a non-natural amino acid residue, chemical derivatives of the peptides, dual peptides, multimers of the peptides, and peptides fused to other proteins or carriers (e.g. cell permeable carriers).

The term "cyclic peptide" as used herein refers to a cyclic derivative of a peptide of the invention to which, e.g., two or more additional amino acid residues suitable for cyclization have been added, often at the carboxyl terminus and at the amino terminus. A cyclic peptide may contain either an intramolecular disulfide bond, i.e., —S—S—, an intramolecular amide bond between the two added residues, i.e., —CONH— or —NHCO— or intramolecular S-alkyl bonds, i.e., —S—(CH$_2$) —CONH— or —NH—CO(CH$_2$)$_n$—S—, wherein n is 1, 2, or more.

A cyclic derivative containing an intramolecular disulfide bond may be prepared by conventional solid phase synthesis (Merrifield et al., 1982) while incorporating suitable S-protected cysteine or homocysteine residues at the positions selected for cyclization such as the amino and carboxyl termini (Sahm et al., 1996, J. Pharm. Pharmacol. 48, 197). Following completion of the chain assembly, cyclization can be performed either by selective removal of the S-protecting groups with a consequent on-support oxidation of free corresponding two SH-functions, to form S—S bonds, followed by conventional removal of the product from the support and appropriate purification procedure, or by removal of the peptide from the support along with complete side-chain deprotection, followed by oxidation of the free SH-functions in highly dilute aqueous solution.

The cyclic derivatives containing an intramolecular amide bond may be prepared by conventional solid phase synthesis while incorporating suitable amino and carboxyl side-chain protected amino acid derivatives at the positions selected for cyclization. The cyclic derivatives containing intramolecular —S-alkyl bonds can be prepared by conventional solid phase synthesis while incorporating an amino acid residue with a suitable amino-protected side chain, and a suitable S-protected cysteine or homocysteine residue at the positions selected for cyclization.

According to another embodiment, a peptide derivative of the invention may have one or more amino acid residues replaced by the corresponding D-amino acid residue. Thus, a peptide or peptide derivative of the invention may be all-L, all-D, or a mixed D,L-peptide. In another embodiment, an amino acid residue may be replaced by a non-natural amino acid residue. Examples of non-naturally occurring or derivatized non-naturally occurring amino acids include Nα-methyl amino acids, Cα-methyl amino acids, and β-methyl amino acids. Amino acid analogs in general may include but are not limited to β-alanine (β-Ala), norvaline (Nva), norleucine (Nle), 4-aminobutyric acid (γ-Abu), 2-aminoisobutyric acid (Aib), 6-aminohexanoic acid (ε-Ahx), ornithine (orn), hydroxyproline (Hyp), sarcosine, citrulline, cysteic acid, and cyclohexylalanine. Further, such amino acids may include but are not limited to, α-amino isobutyric acid, t-butylglycine, t-butylalanine and phenylglycine.

A chemical derivative of a peptide of the invention includes, but is not limited to, a derivative containing additional chemical moieties not normally a part of the peptide, provided that the derivative retains the desired functional activity of the peptide. Examples of such derivatives include: (a) N-acyl derivatives of the amino terminal or of another free amino group, wherein the acyl group may be either an alkanoyl group, e.g., acetyl, hexanoyl, octanoyl, an aroyl group, e.g., benzoyl, or a blocking group such as Fmoc (fluorenylmethyl-O—CO—), carbobenzoxy (benzyl-O—CO—), monomethoxysuccinyl, naphthyl-NH—CO—, acetylamino-caproyl, adamantyl-NH—CO—; (b) esters of the carboxyl terminal or of another free carboxyl or hydroxy groups; (c) amides of the carboxyl terminal or of another free carboxyl groups produced by reaction with ammonia or with a suitable amine; (d) glycosylated derivatives; (e) phosphorylated derivatives; (f) derivatives conjugated to lipophilic moieties, e.g., caproyl, lauryl, stearoyl; and (g) derivatives conjugated to an antibody or other biological ligand.

Also included among the chemical derivatives are those derivatives obtained by modification of the peptide bond —CO—NH—, for example, by: (a) reduction to —CH$_2$—NH—; (b) alkylation to —CO—N(alkyl)—; and (c) inversion to —NH—CO—.

A dual peptide according to the invention consists of two of the same, or two different, peptides of the invention covalently linked to one another, either directly or through a spacer, such as by a short stretch of alanine residues, or by a putative site for proteolysis (e.g. by cathepsin, see U.S. Pat. No. 5,126,249 and European Patent No. 495,049 with respect to such sites).

Multimers according to the invention consist of polymer molecules formed from a number of the same or different peptides or derivatives thereof. The polymerization is carried out with a suitable polymerization agent, such as 0.1% glutaraldehyde (Audibert et al., 1981, Nature 289, 593).

In one aspect of the invention, the peptide derivative is more resistant to proteolytic degradation than the corresponding non-derivatized peptide. For example, a peptide derivative having D-amino acid substitution(s) in place of one or more L-amino acid residue(s) resists proteolytic cleavage when administered to a mammal. In a preferred aspect of the invention, the peptide derivative has increased permeability across a cell membrane as compared to the corresponding non-derivatized peptide. For example, a peptide derivative may have a lipophilic moiety coupled at the amino terminus and/or carboxyl terminus and/or an internal site. Such derivatives are highly preferred when targeting intracellular protein-protein interactions, provided they retain the desired functional activity. In yet another aspect, a dualized or multimerized peptide or peptide derivative has enhanced functional activity.

The peptides or peptide derivatives of the invention are obtained by any method of peptide synthesis known to those skilled in the art, including synthetic and recombinant techniques. For example, the peptides or peptide derivatives can be obtained by solid phase peptide synthesis which, in brief, consists of coupling the carboxyl group of the C-terminal amino acid to a resin and successively adding N-alpha protected amino acids. The protecting groups may be any such groups known in the art. Before each new amino acid is added to the growing chain, the protecting group of the previous amino acid added to the chain is removed. The coupling of amino acids to appropriate resins has been described by Rivier et al. (U.S. Pat. No. 4,244,946). Such solid phase syntheses have been described, for example, by Merrifield, 1964, J. Am. Chem. Soc. 85, 2149; Vale et al. 1981, Science 213, 1394–1397; Marki et al., 1981, J. Am. Chem. Soc. 103, 3178, and in U.S. Pat. Nos. 4,305,872 and 4,316,891. In a preferred aspect, an automated peptide synthesizer is employed.

Purification of the synthesized peptides or peptide derivatives is carried out by standard methods, including chromatography (e.g., ion exchange, affinity, and sizing column chromatography), centrifugation, differential solubility, hydrophobicity, or by any other standard technique for the purification of proteins. In one embodiment, thin layer chromatography is employed. In another embodiment, reverse phase HPLC (high performance liquid chromatography) is employed.

Finally, structure-function relationships determined from the peptides, peptide derivatives, and other small molecules of the invention may also be used to prepare analogous molecular structures having similar properties. Thus, the invention is contemplated to include molecules in addition to those expressly disclosed that share the structure, hydrophobicity, charge characteristics and side chain properties of the specific embodiments exemplified herein.

In a specific embodiment, the peptide or other small molecule, e.g., derivative or analog, is functionally active, i.e., capable of exhibiting one or more of the identified functional activities associated with a peptide of the invention. As one example, such derivatives or analogs which have the desired immunogenicity or antigenicity can be used in immunoassays, for immunization, for activation or inhibition of effector activity, etc. As another example, such derivatives or analogs which have the desired binding activity can be used for binding to a molecule or other target of interest. As yet another example, such derivatives or analogs which have the desired binding activity can be used for binding to a binding partner specific for another known protein (see e.g., Clemmons, 1993, Mol. Reprod. Dev. 35, 368–374; Loddick et al., 1998, Proc. Natl. Acad. Sci. U.S.A. 95, 1894–1898). Derivatives or analogs that retain, or alternatively lack or inhibit, a desired property-of-interest (e.g., binding to a protein binding partner), can be used as activators, or inhibitors, respectively, of such property and its physiological correlates. A specific embodiment relates to a peptide or other small molecule that can be bound by an anti-peptide antibody. Derivatives or analogs of a peptide can be tested for the desired activity by any functional assay known in the art, including but not limited to the assays described in Section 6 below.

In particular, peptide derivatives can be made by altering amino acid sequences by substitutions, additions or deletions that provide for functionally equivalent molecules, or for functionally enhanced or diminished molecules, as desired. Due to the degeneracy of the genetic code, other nucleic acid sequences which encode substantially the same amino acid sequence may be used for the production of recombinant peptides. These include but are not limited to nucleotide sequences comprising all or portions of a peptide of the invention which is altered by the substitution of different codons that encode a functionally equivalent amino acid residue within the sequence, thus producing a silent change. Likewise, the derivatives of the invention include, but are not limited to, those containing, as a primary amino acid sequence, all or part of the amino acid sequence of a protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are generally understood to be conservative substitutions.

In a specific embodiment of the invention, proteins comprising a part (i.e. fragment) of a peptide of the invention having at least 3, at least 6, or at least 9 (continuous) amino acids of the peptide of the invention is provided. In other embodiments, the fragment consists of at least 10 or at least 20 or at least 50 amino acids of the peptide. In specific embodiments, such fragments are not larger than 35, 100 or 200 amino acids. Derivatives or analogs of peptides include but are not limited to those molecules comprising regions that are substantially homologous to a peptide or fragment thereof (e.g., in various embodiments, at least 60% or 70% or 80% or 90% or 95% or 98% or 99% identity over an amino acid sequence of identical size or when compared to an aligned sequence in which the alignment is done by a computer homology program known in the art) or whose encoding nucleic acid is capable of hybridizing to a coding gene sequence, under high stringency, moderate stringency, or low stringency conditions.

The derivatives and analogs of the invention can be produced by various methods known in the art. The manipulations which result in their production can occur at the gene or protein level. For example, a cloned nucleic acid sequence can be modified by any of numerous strategies known in the art (Sambrook et al., 1989, Molecular Cloning, A Laboratory Manual, 2d ed., Cold Spring Harbor Laboratory Press, Cold Spring Harbor, N.Y.). The sequence can be cleaved at appropriate sites with restriction endonuclease(s), followed by further enzymatic modification if desired, isolated, and ligated in vitro.

Additionally, a nucleic acid sequence can be mutated in vitro or in vivo, to create and/or destroy translation, initiation, and/or termination sequences, or to create variations in coding regions and/or to form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson et al., 1978, J. Biol. Chem. 253:6551), use of TAB® linkers (Pharmacia), etc. See also Section 5. herein which sets forth general cloning techniques.

Manipulations of a protein sequence may also be made at the protein level. Included within the scope of the invention are peptide fragments. or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$, acetylation, formulation, oxidation, reduction, metabolic synthesis in the presence of tunicamycin, etc.

In a preferred embodiment, a peptide derivative is a chimeric or fusion protein comprising a peptide of the invention or fragment thereof joined at its amino- or carboxy-terminus, or both, via a peptide bond to an amino acid sequence of a different protein. Such a chimeric or fusion protein may be produced by recombinant expression of a nucleic acid encoding the protein. In another preferred embodiment, such a chimeric or fusion protein comprises a fragment of at least six (6) amino acids of a peptide of the invention. In a most preferred embodiment, such a chimeric or fusion protein not only comprises a fragment of at least six (6) amino acids of a peptide of the invention but also has a functional activity equivalent to or greater than the peptide of the invention.

5.7. Antibodies

According to the invention, a peptide, peptide fragment, peptide derivative, peptide analog, or a small molecule derivative thereof (e.g., a peptide mimetic), may be used as an immunogen to generate antibodies which immunospecifically bind such an immunogen. Such antibodies may in turn be used as diagnostic or therapeutic agents and include but are not limited to polyclonal, monoclonal, humanized or chimeric antibodies, single chain antibodies, Fab fragments and $F(ab')_2$ fragments, fragments produced by a Fab expression library, anti-idiotypic (anti-Id) antibodies, and epitope-binding fragments of any of the above.

Various procedures well known in the art may be used for the production of polyclonal antibodies to a peptide or derivative or analog. In a particular embodiment, rabbit polyclonal antibodies to an epitope of a protein encoded by a peptide of the invention, or a subsequence thereof of at least three amino acids, can be obtained. For the production of antibody, various host animals can be immunized by injection with the native protein, or a synthetic version, or derivative or fragment thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed to a protein sequence or analog thereof, any technique which provides for the production of antibody molecules by continuous cell lines in culture may be used. For example, the hybridoma technique originally developed by Kohler and Milstein (1975, Nature 256, 495–497), as well as the trioma technique, the human B-cell hybridoma technique (Kozbor et al., 1983, Immunology Today 4, 72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (see e.g., PCT/US90/02545). According to the invention, human antibodies may be used and can be obtained by using human hybridomas (Cole et al., 1983, Proc. Natl. Acad. Sci. U.S.A. 80, 2026–2030) or by transforming human B cells with EBV virus in vitro (Cole et al., 1985, in *Monoclonal Antibodies and Cancer Therapy*, Alan R. Liss, pp. 77–96).

The monoclonal antibodies which may be used in the methods of the invention include but are not limited to human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80, 7308–7312; Kozbor et al., 1983, Immunology Today 4, 72–79; Olsson et al., 1982, Meth. Enzymol. 92, 3–16).

A chimeric antibody is a molecule in which different portions are derived from different animal species, such as those having a variable region derived from a murine mAb and a human immunoglobulin constant region. Techniques have been developed for the production of "chimeric antibodies" (Morrison et al., 1984, Proc. Natl. Acad. Sci. U.S.A. 81, 6851–6855; Neuberger et al., 1984, Nature, 312, 604–608; Takeda et al., 1985, Nature, 314, 452–454) by splicing the genes from a mouse antibody molecule of appropriate antigen specificity together with genes from a human antibody molecule of appropriate biological activity.

Briefly, humanized antibodies are antibody molecules from non-human species having one or more complementarity determining regions (CDRs) from the non-human species and a framework region from a human immunoglobulin molecule. Various techniques have been developed for the production of humanized antibodies (see e.g., Queen, U.S. Pat. No. 5,585,089, which is incorporated herein by reference in its entirety). An immunoglobulin light or heavy chain variable region consists of a "framework" region interrupted by three hypervariable regions, referred to as complementarily determining regions (CDRs). The extent of the framework region and CDRs have been precisely defined (see, Kabat et al., 1983) "Sequences of Proteins of Immunological Interest", U.S. Department of Health and Human Services.

According to the invention, techniques described for the production of single chain antibodies (U.S. Pat. No. 4,946, 778) can be adapted to produce peptide-specific single chain antibodies. An additional embodiment of the invention utilizes the techniques described for the construction of Fab expression libraries (Huse et al., 1989, Science 246, 1275–1281) to allow rapid and easy identification of monoclonal Fab fragments with the desired specificity for proteins, derivatives, or analogs of the invention.

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, the Fab fragments which can be generated by treating the antibody molecule with papain and a reducing agent, and Fv fragments.

Antibodies raised against a peptide can, in turn, be utilized to generate anti-idiotype antibodies that "mimic" the peptide, using techniques well known in the art (see, e.g., Greenspan and Bona, 1993, FASEB J. 7, 437–444; and Nissinoff, 1991, J. Immunol. 147, 2429–2438). For example, antibodies which bind to the peptide and competitively inhibit the binding of peptide to its receptor can be used to generate anti-idiotypes that "mimic" the peptide receptor and, therefore, bind the peptide.

In the production of antibodies, screening for the desired antibody can be accomplished by techniques known in the art (e.g., enzyme-linked immunosorbent assay or ELISA). For example, to select antibodies which recognize a specific domain of a protein, one may assay generated hybridomas for a product which binds to a fragment containing such domain. For selection of an antibody that specifically binds a first homolog but which does not specifically bind a different homolog, one can select on the basis of positive binding to the first homolog and a lack of binding to the second homolog.

Antibody molecules may be purified by many well known techniques, e.g., immunoabsorption or immunoaffinity chromatography, chromatographic methods such as HPLC (high performance liquid chromatography), or a combination thereof, etc.

The functional activity of peptides and other small molecules of the invention, and derivatives and analogs thereof, can be assayed by various antibody methods known to one skilled in the art. For example, where one is assaying for the ability to bind to or compete with another molecule for binding to an anti-peptide antibody, assays known in the art which can be used include but are not limited to competitive and non-competitive assays using techniques such as: radioimmunoassays, ELISA (enzyme linked immunosorbent assay), "sandwich" immunoassays, immunoradiometric assays, gel diffusion precipitin reactions, immunodiffusion assays, in situ immunoassays (e.g., using colloidal gold, enzyme or radioisotope labels), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled.

The methods of antibody production and use employed herein can, for example, be such as those described in Harlow and Lane (Harlow and Lane, 1988, "Antibodies: A Laboratory Manual", Cold Spring Harbor Laboratory Press, Cold Spring Harbor, N.Y.), which is incorporated herein by reference in its entirety.

5.8. Structure of Peptides and Nucleic Acids

The structure of peptides and other small molecules of the invention, of fragments, derivatives and analogs thereof, and, where applicable, of the nucleic acids encoding them, can be analyzed by any of various methods well known in the art. Examples of such methods include but are not limited to those described below.

5.8.1. Peptide Structural Analysis

Well known structural analysis methods (e.g., Chou and Fasman, 1974, Biochemistry 13, 222) may be performed to identify candidate regions of a peptide that assume specific secondary structures. Further secondary structure prediction may be accomplished using computer software programs available in the art.

Additional well known methods of structural analysis can also be employed. These include but are not limited to X-ray crystallography (Engstom, 1974, Biochem. Exp. Biol. 11, 7–13), nuclear magnetic resonance spectroscopy (Clore and Gonenborn, 1989, CRC Crit. Rev. Biochem. 24, 479–564) and computer modeling (Fletterick and Zoller, eds., 1986, Computer Graphics and Molecular Modeling, in Current Communications in Molecular Biology, Cold Spring Harbor Laboratory Press, Cold Spring Harbor, N.Y.).

The single-letter amino acid code as used herein corresponds to the three-letter amino acid code of the Sequence Listing herein, as follows: A, Ala, alanine; R, Arg, arginine; N, Asn, asparagine; D, Asp, aspartic acid; B, Asx, asparagine or aspartic acid; C, Cys, cysteine; Q, Gln, glutamine; E, Glu, glutamic acid; Z, Glx, glutamine or glutamic acid; G, Gly, glycine; H, His, histidine; I, Ile, isoleucine; L, Leu, leucine; K, Lys, lysine; M, Met, methionine; F, Phe, phenylalanine; P, Pro, proline; S, Ser, serine; T, Thr, threonine; W, Trp, tryptophan; Y, Tyr, tyrosine; V, Val, valine; and X, Xaa, unknown or other or any amino acid.

5.8.2. Nucleic Acid Structural Analysis

A nucleic acid encoding a recombinant peptide of the invention can be analyzed, as needed, by any number of methods well known in the art including but not limited to Southern hybridization (Southern, 1975, J. Mol. Biol. 98, 503–517), Northern hybridization (see e.g., Freeman et al., 1983, Proc. Natl. Acad. Sci. U.S.A. 80, 4094–4098), restriction endonuclease mapping (Maniatis, 1982, Molecular Cloning, A Laboratory Manual, Cold Spring Harbor Laboratory Press, Cold Spring Harbor, N.Y.), and DNA sequence analysis. Accordingly, this invention provides nucleic acid probes recognizing a nucleic acid encoding a peptide of the invention. For example, polymerase chain reaction (PCR; U.S. Pat. Nos. 4,683,202, 4,683,195 and 4,889,818; Gyllenstein et al., 1988, Proc. Natl. Acad. Sci. U.S.A. 85, 7652–7656; Ochman et al., 1988, Genetics 120, 621–623; Loh et al., 1989, Science 243, 217–220) followed by Southern hybridization with an nucleic acid-specific probe can allow the detection of an nucleic acid in DNA from various cell types. Methods of amplification other than PCR are commonly known and can also be employed.

In one embodiment, Southern hybridization can be used to determine the genetic linkage of a given nucleic acid. Northern hybridization analysis can be used to determine the expression of an nucleic acid. Various cell types, at various states of development or activity can be tested for nucleic acid expression. The stringency of the hybridization conditions for both Southern and Northern hybridization can be manipulated to ensure detection of nucleic acids with the desired degree of relatedness to the specific nucleic acid probe used. Modifications of these methods and other methods commonly known in the art can be used.

5.9. Expression of Recombinant Peptides

For expression of recombinant peptides of the invention, any nucleotide sequence encoding such peptides predicted from the genetic code can be inserted into an appropriate expression vector (i.e., a vector which contains the necessary elements for the transcription and translation of the inserted protein-coding sequence). A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In yet another embodiment, a fragment of a protein comprising one or more domains of the protein is expressed.

Any of the methods well known in the art for the insertion of DNA fragments into a vector may be used to construct expression vectors containing a chimeric nucleic acid consisting of appropriate transcriptional/translational control signals and the protein coding sequences. These methods may include in vitro recombinant DNA and synthetic techniques and in vivo recombinants (genetic recombination). Expression of a nucleic acid sequence encoding a peptide of the invention may be regulated by a second nucleic acid sequence so that the peptide is expressed in a host transformed with the recombinant DNA molecule. For example, expression of a peptide may be controlled by any promoter/enhancer element known in the art. Promoters which may be used to control nucleic acid expression include, but are not limited to, the SV40 early promoter region (Benoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein nucleic acid (Brinster et al., 1982, Nature 296:39–42); prokaryotic expression vectors such as the β-lactamase promoter (Villa-Kamaroff et al., 1978, Proc. Natl. Acad. Sci. U.S.A. 75:3727–3731), or the lac promoter (DeBoer et al., 1983, Proc. Natl. Acad. Sci. U.S.A. 80:21–25); see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); a gene control region which is active in pancreatic beta cells (Hanahan, 1985, Nature 315:115–122), an immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

In a specific embodiment, a vector is used that comprises a promoter operably linked to a nucleic acid encoding a peptide of the invention, one or more origins of replication, and, optionally, one or more selectable markers (e.g., an antibiotic resistance gene).

Expression vectors containing nucleic acid inserts can be identified by any of a number of well known methods. Three general approaches are: (a) nucleic acid hybridization; (b) presence or absence of "marker" gene functions; and (c) expression of inserted sequences. In the first approach, the presence of a gene inserted in an expression vector can be detected by nucleic acid hybridization using probes comprising sequences that are homologous to an inserted gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleic acid of interest in the vector. For example, if the nucleic acid is inserted within the marker gene sequence of the vector, recombinants containing the insert can be identified by the absence of the marker gene function. In the third approach, recombinant expression vectors can be identified by assaying the product expressed by the recombinant. Such assays can be based, for example, on the physical or functional properties of an expressed peptide in in vitro assay systems (e.g., binding with an anti-peptide antibody of the invention).

A host cell strain for expressing a nucleic acid encoding a peptide of the invention may be chosen which modulates the expression of the inserted sequences, or modifies and processes the nucleic acid product in the specific fashion desired. Expression from certain promoters can be elevated in the presence of certain inducers; thus, expression of a genetically-engineered peptide of the invention may be controlled. Furthermore, different host cells have characteristic and specific mechanisms for the translational and post-translational processing and modification (e.g., glycosylation, phosphorylation). Appropriate cell lines or host systems can be chosen to ensure the desired modification and processing of the foreign peptide or protein expressed. For example, expression in a bacterial system can be used to produce a non-glycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

5.10. Identification of Molecules Having Binding Capacity

This invention provides screening methods useful in the identification of molecules (e.g. proteins or other compounds) which bind to, or otherwise directly interact with, the identified peptides and other small molecules of the invention. Such screening methods are well known in the art (see e.g., PCT International Publication No. WO 96/34099, published Oct. 31, 1996, which is incorporated by reference herein in its entirety). Such proteins and compounds may include endogenous cellular components which interact with the identified peptides in vivo and which, therefore, may provide new targets for pharmaceutical and therapeutic interventions, as well as recombinant, synthetic, and otherwise exogenous compounds which may have binding capacity and, therefore, may be candidates for pharmaceutical agents. Thus, in one series of embodiments, cell lysates or tissue homogenates may be screened for proteins or other compounds which bind to a peptide of the invention. Alternatively, any of a variety of exogenous compounds, both naturally occurring or synthetic (e.g., libraries of small molecules), may be screened for binding capacity.

As will be apparent to one of ordinary skill in the art, there are numerous other methods of screening individual proteins or other compounds, as well as large libraries of proteins or other compounds (e.g., phage display libraries) to identify molecules which bind to peptides or other small molecules of the invention, or fragments, derivatives or analogs thereof. All of these methods comprise the step of mixing such a molecule with test compounds, allowing time for any binding to occur, and assaying for any bound complexes. All such methods are contemplated by the present disclosure of substantially pure peptides and other small molecules, substantially pure functional domain fragments, fusion proteins, antibodies, and methods of making and using the same.

In a preferred embodiment, a peptide of the invention having a desired functional activity in a functional assay can be evaluated for cross reactivity with other cellular components by using the peptide, or a chimeric or fusion protein thereof, as "bait" in a yeast two-hybrid assay system (Fields and Song, 1989, Nature 340:245–246; U.S. Pat. No. 5,283, 173) or a variation thereof. In this way, other potential interactions or functional effects of a peptide of the invention can be identified prior to pharmaceutical development and clinical use.

The yeast two-hybrid method has been used to analyze IGF-1-receptor interactions (see Zhu and Kahn, 1997, Proc. Natl. Acad. Sci. U.S.A. 94, 13063–13068). Because interactions are screened for in yeast, the protein-protein interactions detected occur under physiological conditions that mimic conditions in eukaryotic cells, including vertebrates or invertebrates (Chien et al., 1991, Proc. Natl. Acad. Sci. U.S.A. 88, 9578–9581). This feature facilitates identification of proteins capable of interaction with peptides, derivatives, or fusion proteins of the invention having a desired functional activity.

Identification of interacting proteins by the improved yeast two-hybrid system is based upon the detection of expression of a reporter gene, the transcription of which is dependent upon the reconstitution of a transcriptional regulator by the interaction of two proteins, each fused to one half of the transcriptional regulator. The "bait" (i.e., peptide or fusion protein or derivative or analog thereof) and "prey" (proteins to be tested for ability to interact with the bait) are expressed as fusion proteins to a DNA binding domain and to a transcriptional regulatory domain, respectively, or vice versa. In various specific embodiments, the prey has a complexity of at least about 50, about 100, about 500, about 1,000, about 5,000, about 10,000, or about 50,000; or has a complexity in the range of about 25 to about 100,000, about 100 to about 50,000, about 50,000 to about 100,000, or about 100,000 to about 500,000. For example, the prey population can be one or more nucleic acids encoding mutants of a protein (e.g., as generated by site-directed mutagenesis or another method of making mutations in a nucleotide sequence). Preferably, the prey populations are proteins encoded by DNA, e.g., cDNA or genomic DNA or synthetically-generated DNA. For example, the populations can be expressed from chimeric genes comprising cDNA sequences from an un-characterized sample of a population of cDNA from mRNA.

One characteristic of the yeast two-hybrid system is that proteins examined in this system are expressed as cytoplasmic proteins, and therefore facilitating identification of interactors with the peptides and derivatives thereof of the invention.

In one embodiment, recombinant biological libraries expressing random peptides can be used as the source of prey nucleic acids.

In another embodiment, the invention provides methods of screening for inhibitors or enhancers of the protein interactants identified herein. Briefly, the protein-protein interaction assay can be carried out as described herein, except that it is done in the presence of one or more candidate molecules. An increase or decrease in reporter gene activity relative to that present when the one or more candidate molecules are absent indicates that the candidate molecule has an effect on the interacting pair. In a preferred method, inhibition of the interaction is selected for (i.e., inhibition of the interaction is necessary for the cells to survive), for example, where the interaction activates the URA3 gene, causing yeast to die in medium containing the chemical 5-fluoroorotic acid (Rothstein, 1983, Meth. Enzymol. 101, 167–180). The identification of inhibitors of such interactions can also be accomplished, for example, but not by way of limitation, using competitive inhibitor assays, as described above.

In general, proteins of the bait and prey populations are provided as fusion (chimeric) proteins (preferably by recombinant expression of a chimeric coding sequence) comprising each protein contiguous to a pre-selected sequence. For one population, the pre-selected sequence is a DNA binding domain. The DNA binding domain can be any DNA binding domain, as long as it specifically recognizes a DNA sequence within a promoter. For example, the DNA binding domain is of a transcriptional activator or inhibitor. For the other population, the pre-selected sequence is an activator or inhibitor domain of a transcriptional activator or inhibitor, respectively. The regulatory domain alone (not as a fusion to a protein sequence) and the DNA-binding domain alone (not as a fusion to a protein sequence) preferably do not detectably interact (so as to avoid false positives in the assay). The assay system further includes a reporter gene operably linked to a promoter that contains a binding site for the DNA binding domain of the transcriptional activator (or inhibitor).

Accordingly, in the present method of the invention, binding of a peptide of the invention to a fusion protein leads to reconstitution of a transcriptional activator (or inhibitor) which activates (or inhibits) expression of the reporter gene. The activation (or inhibition) of transcription of the reporter gene occurs intracellularly, e.g., in prokaryotic or eukaryotic cells, preferably in cell culture.

The promoter that is operably linked to the reporter gene nucleotide sequence can be a native or non-native promoter of the nucleotide sequence, and the DNA binding site(s) that are recognized by the DNA binding domain portion of the fusion protein can be native to the promoter (if the promoter normally contains such binding site(s)) or non-native to the promoter. Thus, for example, one or more tandem copies (e.g., four or five copies) of the appropriate DNA binding site can be introduced upstream of the TATA box in the desired promoter (e.g., in the area of about position −100 to about −400). In a preferred aspect, 4 or 5 tandem copies of the 17 bp UAS (GAL4 DNA binding site) are introduced upstream of the TATA box in the desired promoter, which is upstream of the desired coding sequence for a selectable or detectable marker. In a preferred embodiment, the GAL1-10 promoter is operably fused to the desired nucleotide sequence; the GAL1-10 promoter already contains 4 binding sites for GAL4.

Alternatively, the transcriptional activation binding site of the desired gene(s) can be deleted and replaced with GAL4 binding sites (Bartel et al., 1993, BioTechniques 14, 920–924; Chasman et al., 1989, Mol. Cell. Biol. 9, 4746–4749). The reporter gene preferably contains the sequence encoding a detectable or selectable marker, the expression of which is regulated by the transcriptional activator, such that the marker is either turned on or off in the cell in response to the presence of a specific interaction. Preferably, the assay is carried out in the absence of background levels of the transcriptional activator (e.g., in a cell that is mutant or otherwise lacking in the transcriptional activator).

In one embodiment, more than one reporter gene is used to detect transcriptional activation, e.g., one reporter gene encoding a detectable marker and one or more reporter genes encoding different selectable markers. The detectable marker can be any molecule that can give rise to a detectable signal, e.g., a fluorescent protein or a protein that can be readily visualized or that is recognizable by a specific antibody. The selectable marker can be any protein molecule that confers the ability to grow under conditions that do not support the growth of cells not expressing the selectable marker, e.g., the selectable marker is an enzyme that provides an essential nutrient and the cell in which the interaction assay occurs is deficient in the enzyme and the selection medium lacks such nutrient. The reporter gene can either be under the control of the native promoter that naturally contains a binding site for the DNA binding protein, or under the control of a heterologous or synthetic promoter.

The activation domain and DNA binding domain used in the assay can be from a wide variety of transcriptional activator proteins, as long as these transcriptional activators have separable binding and transcriptional activation domains. For example, the GAL4 protein of S. cerevisiae (Ma et al., 1987, Cell 48, 847–853), the GCN4 protein of S. cerevisiae (Hope and Struhl, 1986, Cell 46, 885–894), the ARD1 protein of S. cerevisiae (Thukral et al., 1989, Mol. Cell. Biol. 9, 2360–2369), and the human estrogen receptor (Kumar et al., 1987, Cell 51, 941–951), have separable DNA binding and activation domains. The DNA binding domain and activation domain that are employed in the fusion proteins need not be from the same transcriptional activator. In a specific embodiment, a GAL4 or LEXA DNA binding domain is employed. In another specific embodiment, a GAL4 or herpes simplex virus VP16 (Triezenberg et al., 1988, Genes Dev. 2, 730–742) activation domain is employed. In a specific embodiment, amino acids 1–147 of GAL4 (Ma et al., 1987, Cell 48, 847–853; Ptashne et al., 1990, Nature 346, 329–331) is the DNA binding domain, and amino acids 411–455 of VP16 (Triezenberg et al., 1988, Genes Dev. 2, 730–742; Cress et al., 1991, Science 251, 87–90) comprise the activation domain.

In a preferred embodiment, the yeast transcription factor GAL4 is reconstituted by protein-protein interaction and the host strain is mutant for GAL4. In another embodiment, the DNA-binding domain is Ace1N and/or the activation domain is Ace1, the DNA binding and activation domains of the Ace1 protein, respectively. Ace1 is a yeast protein that activates transcription from the CUP1 operon in the presence of divalent copper. CUP1 encodes metallothionein, which chelates copper, and the expression of CUP1 protein allows growth in the presence of copper, which is otherwise toxic to the host cells. The reporter gene can also be a CUP1-lacZ fusion that expresses the enzyme beta-galactosidase (detectable by routine chromogenic assay) upon binding of a reconstituted Ace1N transcriptional activator (see Chaudhuri et al., 1995, FEBS Letters 357, 221–226). In another specific embodiment, the DNA binding domain of the human estrogen receptor is used, with a reporter gene driven by one or three estrogen receptor response elements (Le Douarin et al., 1995, Nucl. Acids. Res. 23, 876–878).

The DNA binding domain and the transcriptional activator/inhibitor domain each preferably has a nuclear localization signal (see Ylikomi et al., 1992, EMBO J. 11, 3681–3694; Dingwall and Laskey, 1991, TIBS 16, 479–481) functional in the cell in which the fusion proteins are to be expressed.

To facilitate isolation of the encoded proteins, the fusion constructs can further contain sequences encoding affinity tags such as glutathione-S-transferase or maltose-binding protein or an epitope of an available antibody, for affinity purification (e.g., binding to glutathione, maltose, or a particular antibody specific for the epitope, respectively) (Allen et al., 1995, TIBS 20, 511–516). In another embodiment, the fusion constructs further comprise bacterial promoter sequences for recombinant production of the fusion protein in bacterial cells.

The host cell in which the interaction assay occurs can be any cell, prokaryotic or eukaryotic, in which transcription of the reporter gene can occur and be detected, including, but not limited to, mammalian (e.g., monkey, mouse, rat, human, bovine), chicken, bacterial, or insect cells, and is preferably a yeast cell. Expression constructs encoding and capable of expressing the binding domain fusion proteins, the transcriptional activation domain fusion proteins, and the reporter gene product(s) are provided within the host cell, by mating of cells containing the expression constructs, or by cell fusion, transformation, electroporation, microinjection, etc. In a specific embodiment in which the assay is carried out in mammalian cells (e.g., hamster cells, HeLa cells), the DNA binding domain is the GAL4 DNA binding domain, the activation domain is the herpes simplex virus VP16 transcriptional activation domain, and the reporter gene contains the desired coding sequence operably linked to a minimal promoter element from the adenovirus E1B gene driven by several GAL4 DNA binding sites (see Fearon et al., 1992, Proc. Natl. Acad. Sci. U.S.A. 89, 7958–7962). The host cell used should not express an endogenous transcription factor that binds to the same DNA site as that recognized by the DNA binding domain fusion population. Also, preferably, the host cell is mutant or otherwise lacking in an endogenous, functional form of the reporter gene(s) used in the assay. Various vectors and host strains for expression of the two fusion protein populations in yeast are known and can be used (see e.g., U.S. Pat. No. 5,1468,614; Bartel et al., 1993, "Using the two-hybrid system to detect protein-protein interactions" In *Cellular Interactions in Development*, Hartley, ed., Practical Approach Series xviii, IRL Press at Oxford University Press, New York, N.Y., pp. 153–179; Fields and Sternglanz, 1994, Trends In Genetics 10, 286–292). By way of example but not limitation, yeast strains or derivative strains made therefrom, which can be used are N105, N106, N1051, N1061, and YULH. Other exemplary strains that can be used in the assay of the invention also include, but are not limited to, the following:

Y190: MATa, ura3-52, his3-200, lys2-801, ade2-101, trp1-901, leu2-3,112, gal4α, gal80α, cyh$^r$2, LYS2::GAL1$_{UAS}$-HIS3$_{TATA}$HIS3, URA3::GAL1$_{UAS}$-GAL1$_{TATA}$-lacZ; Harper et al., 1993, Cell 75, 805–816, available from Clontech, Palo Alto, Calif. Y190 contains HIS3 and lacZ reporter genes driven by GAL4 binding sites.

CG-1945: MATa, ura3-52, his3-200, lys2-801, ade2-101, trp1-901, leu2-3,112, gal4-542, gal80-538, cyh$^r$2, LYS2::GAL1$_{UAS}$-HIS3$_{TATA}$HIS3, URA3:: GAL1$_{UAS17mers(x3)}$-CYC1$_{TATA}$-lacZ; available from Clontech, Palo Alto, Calif. CG-1945 contains HIS3 and lacZ reporter genes driven by GAL4 binding sites.

Y187: MAT-α, ura3-52, his3-200, ade2-101, trp1-901, leu2-3,112, gal4α, gal80α, URA3::GAL1$_{UAS}$-GAL1$_{TATA}$-lacZ, available from Clontech, Palo Alto, Calif. Y187 contains a lacZ reporter gene driven by GAL4 binding sites.

SFY526: MATa, ura3-52, his3-200, lys2-801, ade2-101, trp1-901, leu2-3,112, gal4-542, gal80-538, can$^r$, URA3::GAL1-lacZ, available from Clontech, Palo Alto, Calif. SFY526 contains HIS3 and lacZ reporter genes driven by GAL4 binding sites.

HF7c: MATa, ura3-52, his3-200, lys2-801, ade2-101, trp1-901, leu2-3,112, gal4-542, gal80-538, LYS2::GAL1-HIS3, URA3::GAL1$_{UAS17mers(x3)}$-CYC1-lacZ, available from Clontech, Palo Alto, Calif. HF7c contains HIS3 and lacZ reporter genes driven by GAL4 binding sites.

YRG-2: MATa, ura3-52, his3-200, lys2-801, ade2-101, trp1-901, leu2-3,112, gal4-542, gal80-538, LYS2::GAL1$_{UAS}$-GAL1$_{TATA}$-HIS3, URA3:: GAL1$_{UAS17mers(x3)}$-CYC1-lacZ, available from Stratagene, La Jolla, Calif. YRG-2 contains HIS3 and lacZ reporter genes driven by GAL4 binding sites. Many other strains commonly known and available in the art can be used.

If not already lacking in endogenous reporter gene activity, cells mutant in the reporter gene may be selected by known methods, or the cells can be made mutant in the target reporter gene by known gene-disruption methods prior to introducing the reporter gene (Rothstein, 1983, Meth. Enzymol. 101, 202–211).

In a specific embodiment, plasmids encoding the different fusion protein populations can be introduced simultaneously into a single host cell (e.g., a haploid yeast cell) containing one or more reporter genes, by co-transformation, to conduct the assay for protein-protein interactions. Or, preferably, the two fusion protein populations are introduced into a single cell either by mating (e.g., for yeast cells) or cell fusions (e.g., of mammalian cells). In a mating type assay, conjugation of haploid yeast cells of opposite mating type that have been transformed with a binding domain fusion expression construct (preferably a plasmid) and an activation (or inhibitor) domain fusion expression construct (preferably a plasmid), respectively, will deliver both constructs into the same diploid cell. The mating type of a yeast strain may be manipulated by transformation with the HO gene (Herskowitz and Jensen, 1991, Meth. Enzymol. 194, 132–146).

In a preferred embodiment, a yeast interaction mating assay is employed using two different types of host cells, strain-type a and alpha of the yeast *Saccharomyces cerevisiae*. The host cell preferably contains at least two reporter genes, each with one or more binding sites for the DNA-binding domain (e.g., of a transcriptional activator). The activator domain and DNA binding domain are each parts of chimeric proteins formed from the two respective populations of proteins. One strain of host cells, for example the a strain, contains fusions of the library of nucleotide sequences with the DNA-binding domain of a transcriptional activator, such as GAL4. The hybrid proteins expressed in this set of host cells are capable of recognizing the DNA-binding site in the promoter or enhancer region in the reporter gene construct. The second set of yeast host cells, for example, the alpha strain, contains nucleotide sequences encoding fusions of a library of DNA sequences fused to the activation domain of a transcriptional activator.

In a preferred embodiment, the fusion protein constructs are introduced into the host cell as a set of plasmids. These plasmids are preferably capable of autonomous replication in a host yeast cell and preferably can also be propagated in *E. coli*. The plasmid contains a promoter directing the transcription of the DNA binding or activation domain fusion genes, and a transcriptional termination signal. The plasmid also preferably contains a selectable marker gene, permitting selection of cells containing the plasmid. The plasmid can be single-copy or multi-copy. Single-copy yeast plasmids that have the yeast centromere may also be used to express the activation and DNA binding domain fusions (Elledge et al., 1988, Gene 70, 303–312).

In another embodiment, the fusion constructs are introduced directly into the yeast chromosome via homologous recombination. The homologous recombination for these purposes is mediated through yeast sequences that are not essential for vegetative growth of yeast, e.g., the MER2, MERI, ZIPI, REC102, or ME14 gene.

Bacteriophage vectors can also be used to express the DNA binding domain and/or activation domain fusion proteins. Libraries can generally be prepared faster and more easily from bacteriophage vectors than from plasmid vectors.

In a specific embodiment, the present invention provides a method of detecting one or more protein-protein interactions comprising (a) recombinantly expressing a peptide of the invention having a desired functional activity, or a derivative or analog thereof, in a first population of yeast cells being of a first mating type and comprising a first fusion protein containing the peptide amino acid sequence and a DNA binding domain, wherein said first population of yeast cells contains a first nucleotide sequence operably linked to a promoter driven by one or more DNA binding sites recognized by said DNA binding domain such that an interaction of said first fusion protein with a second fusion protein, said second fusion protein comprising a transcriptional activation domain, results in increased transcription of said first nucleotide sequence; (b) recombinantly expressing in a second population of yeast cells of a second mating type different from said first mating type, a plurality of said second fusion proteins, each second fusion protein comprising a sequence of a fragment, derivative or analog of a protein and an activation domain of a transcriptional activator, in which the activation domain is the same in each said second fusion protein; (c) mating said first population of yeast cells with said second population of yeast cells to form a third population of diploid yeast cells, wherein said third population of diploid yeast cells contains a second nucleotide sequence operably linked to a promoter driven by a DNA binding site recognized by said DNA binding domain such that an interaction of a first fusion protein with a second fusion protein results in increased transcription of said second nucleotide sequence, in which the first and second nucleotide sequences can be the same or different; and (d) detecting said increased transcription of said first and/or second nucleotide sequence, thereby detecting an interaction between a first fusion protein and a second fusion protein. In a preferred aspect, between step (a) and (b), a step is carried out of negatively selecting to eliminate those yeast cells in said first population which said increased transcription of said first nucleotide sequence occurs in the absence of said second fusion protein (see e.g. PCT International Publication No. WO 97/47763, published Dec. 18, 1997, which is incorporated by reference herein in its entirety).

In a preferred embodiment, the bait peptide sequence and the prey library of chimeric genes are combined by mating the two yeast strains on solid media, such that the resulting diploids contain both kinds of chimeric genes, i.e., the DNA-binding domain fusion and the activation domain fusion.

Preferred reporter genes include the URA3, HIS3 and/or the lacZ genes (see e.g., Rose and Botstein, 1983, Meth. Enzymol. 101, 167–180) operably linked to GAL4 DNA-binding domain recognition elements. Other reporter genes include but are not limited to, Green Fluorescent Protein (GFP) (Cubitt et al., 1995, Trends Biochem. Sci. 20, 448–455), luciferase, LEU2, LYS2, ADE2, TRP1, CAN1, CYH2, GUS, CUP1 or chloramphenicol acetyl transferase (CAT). Expression of the reporter genes can be detected by techniques known in the art (see e.g. PCT International Publication No. WO 97/47763, published Dec. 18, 1997, which is incorporated by reference herein in its entirety).

In a specific embodiment, transcription of the reporter gene is detected by a linked replication assay. For example, as described by Vasavada et al., 1991, Proc. Natl. Acad. Sci. U.S.A. 88, 10686–10690, expression of SV40 large T antigen is under the control of the E1B promoter responsive to GAL4 binding sites. The replication of a plasmid containing the SV40 origin of replication, indicates a protein-protein interaction. Alternatively, a polyoma virus replicon can be used (Id.).

In another embodiment, the expression of reporter genes that encode proteins can be detected by immunoassay, i.e., by detecting the immunospecific binding of an antibody to such protein, which antibody can be labeled, or incubated with a labeled binding partner to the antibody, to yield a detectable signal. Alam and Cook disclose non-limiting examples of detectable marker genes that can be operably linked to a transcriptional regulatory region responsive to a reconstituted transcriptional activator, and thus used as reporter genes (Alam and Cook, 1990, Anal. Biochem. 188, 245–254).

The activation of reporter genes like URA3 or HIS3 enables the cells to grow in the absence of uracil or histidine, respectively, and hence serves as a selectable marker. Thus, after mating, the cells exhibiting protein-protein interactions are selected by the ability to grow in media lacking a nutritional component, such as uracil or histidine (see Le Douarin et al., 1995, Nucl. Acids Res. 23, 876–878; Durfee et al., 1993, Genes Dev. 7, 555–569; Pierrat et al., 1992, Gene 119, 237–245; Wolcott et al., 1966, Biochem. Biophys. Acta 122, 532–534). In other embodiments of the present invention, the activities of the reporter genes like GFP or lacZ are monitored by measuring a detectable signal (e.g., fluorescent or chromogenic, respectively) that results from the activation of these reporter genes. LacZ transcription, for example, can be monitored by incubation in the presence of a substrate, such as X-gal (5-bromo-4-chloro-3-indolyl-β-D-galactoside), of its encoded enzyme, β-galactosidase.

In a preferred embodiment of the present invention, false positives arising from transcriptional activation by the DNA binding domain fusion proteins in the absence of a transcriptional activator domain fusion protein are prevented or reduced by negative selection prior to exposure to the activation domain fusion population (see e.g. PCT International Publication No. WO 97/47763, published Dec. 18, 1997, which is incorporated by reference herein in its entirety). By way of example, if such cell contains URA3 as a reporter gene, negative selection is carried out by incubating the cell in the presence of 5-fluoroorotic acid (5-FOA, which kills URA+cells (Rothstein, 1983, Meth. Enzymol. 101, 167–180). Hence, the metabolism of 5-FOA will lead to cell death of self-activating DNA-binding domain hybrids.

In a preferred aspect, negative selection involving a selectable marker as a reporter gene can be combined with the use of a toxic or growth inhibitory agent to allow a higher rate of processing than other methods. Negative selection can also be carried out on the activation domain fusion population prior to interaction with the DNA binding domain fusion population, by similar methods, either alone or in addition to negative selection of the DNA binding fusion opulation. Negative selection can be carried out on the recovered protein-protein complex by known methods (see e.g., Bartel et al., 1993, BioTechniques 14, 920–924; PCT International Publication No. WO 97/47763, published Dec. 18, 1997).

In a preferred embodiment of the invention the DNA sequences encoding the pairs of interactive proteins are isolated by a method wherein either the DNA-binding domain hybrids or the activation domain hybrids are amplified, in separate respective reactions. Preferably, the amplification is carried out by polymerase chain reaction (PCR) (see U.S. Pat. Nos. 4,683,202; 4,683,195; and 4,889, 818; Gyllenstein et al., 1988, Proc. Natl. Acad. Sci. U.S.A. 85:7652–7656; Ochman et al., 1988, Genetics 120:621–623; Loh et al., 1989, Science 243:217–220; Innis et al., 1990, *PCR Protocols*, Academic Press, Inc., San Diego, Calif.) using pairs of oligonucleotide primers specific for either the DNA-binding domain hybrids or the activation domain hybrids. Other amplification methods known in the art can be used, including but not limited to ligase chain reaction (see EP 320,308), use of Qβ replicase, or methods listed in Kricka et al., 1995, *Molecular Probing, Blotting, and Sequencing*, Academic Press, New York, Chapter 1 and Table IX.

The plasmids encoding the DNA-binding domain hybrid and the activation domain hybrid proteins can also be isolated and cloned by any of the methods well known in the art. For example, but not by way of limitation, if a shuttle (yeast to *E. coli*) vector is used to express the fusion proteins, the genes can be recovered by transforming the yeast DNA into *E. coli* and recovering the plasmids from *E. coli* (see e.g., Hoffman et al., 1987, Gene 57, 267–272). Alternatively, the yeast vector can be isolated, and the insert encoding the fusion protein subcloned into a bacterial expression vector, for growth of the plasmid in *E. coli*.

6. EXAMPLES

The invention described and claimed herein can be further appreciated by one skilled in the art through reference to the examples which follow. These examples are provided merely to illustrate several aspects of the invention and shall not be construed to limit the invention in any way.

6.1. A Surface on the G Protein β Subunit Involved in Interactions with Adenylyl Cyclases Receptor activation of heterotrimeric G proteins dissociates Gα from the Gβγ complex, allowing both to regulate effectors. Little is known about the effector-interaction regions or domains of Gβγ. We had used molecular modeling to dock a peptide encoding residues 956–982 of adenylyl cyclase (AC) 2 (SEQ ID NO:3) onto Gβ to identify residues of Gβ that may interact with effectors. Based on predictions from the model, we synthesized peptides encoding residues 86–105 (Gβ86–105) (SEQ ID NO:5) and 115–135 (Gβ115–135) (SEQ ID NO:6) of Gβ (SEQ ID NO:1). The Gβ86–105 peptide inhibited Gβγ stimulation of AC2 (SEQ ID NO:3) and blocked Gβγ inhibition of AC1 (SEQ ID NO:2) and by itself inhibited calmodulin-stimulated AC1, thus displaying partial agonist activity. Substitution of Met-101 with Asn in Gβ86–105 resulted in the loss of both the inhibitory and partial agonist activities. Most activities of the Gβ115–135 peptide were similar to those of Gβ86–105, but Gβ115–135 was less effective in blocking Gβγ inhibition of AC1. Substitution of Tyr-124 with Val in the Gβ115–135 peptide diminished all of its activities. These results identify the region encoded by amino acids 84–143 of Gβ (SEQ ID NO:1) as a surface that is involved in transmitting signals to effectors.

6.1.1. Introduction

Heterotrimeric G proteins serve as signal transducers for a wide variety of receptors. Both Gα and Gβγ subunits can communicate receptor signals (Fung et al., 1981, Proc. Natl. Acad. Sci. U.S.A. 78, 152–156; Northup et al., 1983, J. Biol. Chem. 258, 11369–11376; Logothetis et al., 1987, Nature 325, 321–326; Tang and Gilman, 1991, Science 254, 1500–1503; Dietzel and Kurjan, 1987, Cell 50, 1000–1010). Regions of Gβγ complex involved in communicating the signal to effectors have not been well characterized. We had identified the region of residues 956–982 of adenylyl cyclase (AC) 2 (SEQ ID NO:3) as being involved in receiving signals from Gβγ (Chen et al., 1995, Science 268, 1166–1169). By using the yeast two-hybrid system, the AC2 region of residues 956–982 has been subsequently shown to interact with Gβ but not Gγ subunits (Yan and Gautam, 1996, J. Biol. Chem. 271, 17597–17601). In recent studies we found that the peptide encoding residues 956–982 of AC2 (SEQ ID NO:3) can be crosslinked to Gβ when it is part of the free Gβγ complex but not when it is part of the heterotrimer, indicating that the putative binding surface on Gβ for the AC2 peptide is occluded by interactions with Gα. On the basis of constraints deduced from the crosslinking studies and other biophysical criteria, we docked the AC2 of Gβ by using molecular modeling techniques (Weng et al., 1996, J. Biol. Chem. 271, 26445–26448). From this docking model, we have identified the regions of Gβ that are predicted to interact with the AC2 peptide. Herein we have tested whether peptides encoding the effector-interaction surface of Gβ predicted from the modeling (Weng et al., 1996, J. Biol. Chem. 271, 26445–26448) can modulate Gβγ regulation of AC1 and AC2.

6.1.2. Materials and Methods

Materials. Reagents for peptide synthesis were from Bachem. [α-$^{32}$P]ATP was from New England Nuclear. Tissue culture reagents and fetal calf serum was from GIBCO. All other chemicals used were the highest grade available.

Peptide Synthesis. Peptides were synthesized on an Applied Biosystems peptide synthesizer (model 431A) and purified by HPLC on acetonitrile gradients. Purified peptides were lyophilized and stored at −20° C. When required peptides were dissolved in water to final concentration of 1–3 mM. Identity of the peptides was verified by mass spectrometry.

Expression of G-Protein Subunits And Adenylyl Cyclases. Gβγ was purified from bovine brain (Dingus et al., 1994, Meth. Enzymol. 237, 457–471). Q227L-Gα$_s$ was expressed in rabbit reticulocyte lysates. AC2 was expressed in Sf9 cells by infection with recombinant baculovirus (Jacobowitz and Iyengar, 1994, Proc. Natl. Acad. Sci. U.S.A. 91, 10630–10634). AC2 assays have been described (Chen et al., 1995, Science 268, 1166–1169). Bovine AC1 (Jacobowitz et al., 1993, J. Biol. Chem. 268, 3829–3832) was epitope tagged at the N terminus with the FLAG epitope (Jacobowitz and Iyengar, 1994, Proc. Natl. Acad. Sci. U.S.A. 91, 10630–10634) and expressed in Sf9 cells by baculovirus infection.

Adenylyl Cyclase Assays. AC2 assays have been described (Chen et al., 1995, Science 268, 1166–1169). When required the peptides were mixed with adenylyl cyclase containing membranes and held on ice for 10 min prior to assays. Approximately 1–4 μg of AC2 Sf9 cell membranes per assay tube was used. All assays contained a mixture of protease inhibitors. The final concentration of each inhibitor was leupeptin at 3.2 μg/ml, aprotinin at 2 μg/ml, phenanthroline at 1.0 mM, and phenylmethylsulfonyl fluoride at 1.0 mM. To study Gβγ inhibition, AC1-containing Sf9 cell membranes (1–4 μg per assay tube) was used. In these assays, in addition to the other standard reagents, the assay mixture contained either 1 mM EGTA or 50 μM CaCl$_2$ plus 100 nM calmodulin (CaM). All experiments were repeated two or more times with qualitatively similar results. Typical experiments are shown. Values are mean±SD of triplicate determinations.

Molecular Modeling. Procedures for molecular modeling have been described (Weng et al., 1996, J. Biol. Chem. 271, 26445–26448). Briefly, a secondary structure prediction of the AC2 peptide containing residues 956–982 (AC2 956–982) was obtained and used to construct an energy minimized three-dimensional model of the peptide. To identify likely interaction surfaces, the electrostatic potentials of the AC2 956–982 peptide and the Gβ protein (Sondek et al., 1996, Nature 379, 369–374) were visualized with the GRASP program. Long-range electrostatic interactions were then used as guides in the initial docking of the peptide to Gβ. The structure of the AC2 956–982 peptide docked to Gβ was subjected to energy minimization followed by conformational explorations with a novel Monte Carlo-based method (Guarnieri and Weinstein, 1996, J. Am. Chem. Soc. 118, 5580–5589). The most favorable structure of the docked AC2 peptide interacting with Gβ was thus obtained within the Imposed constraints. Contact residues on Gβ were identified with the LOOK software (MAG, Palo Alto, Calif.) as residues within 4 Å of the AC2 peptide.

6.1.3. Results

Figure 2A:
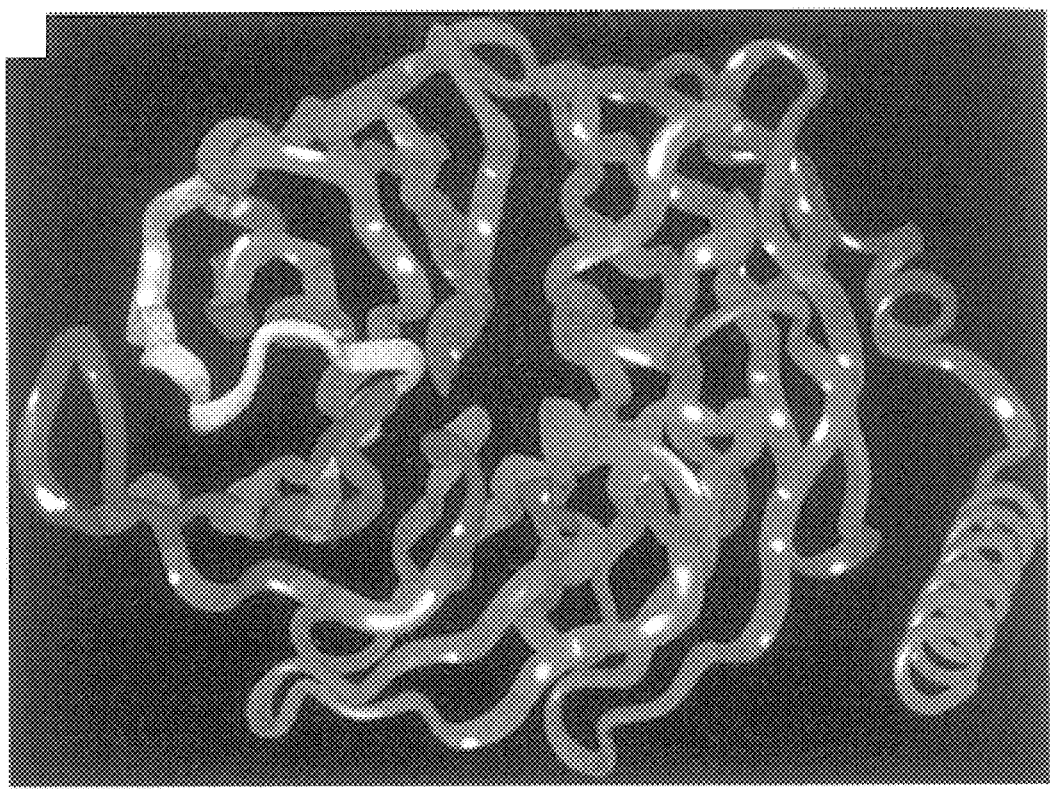
Figure 2B:
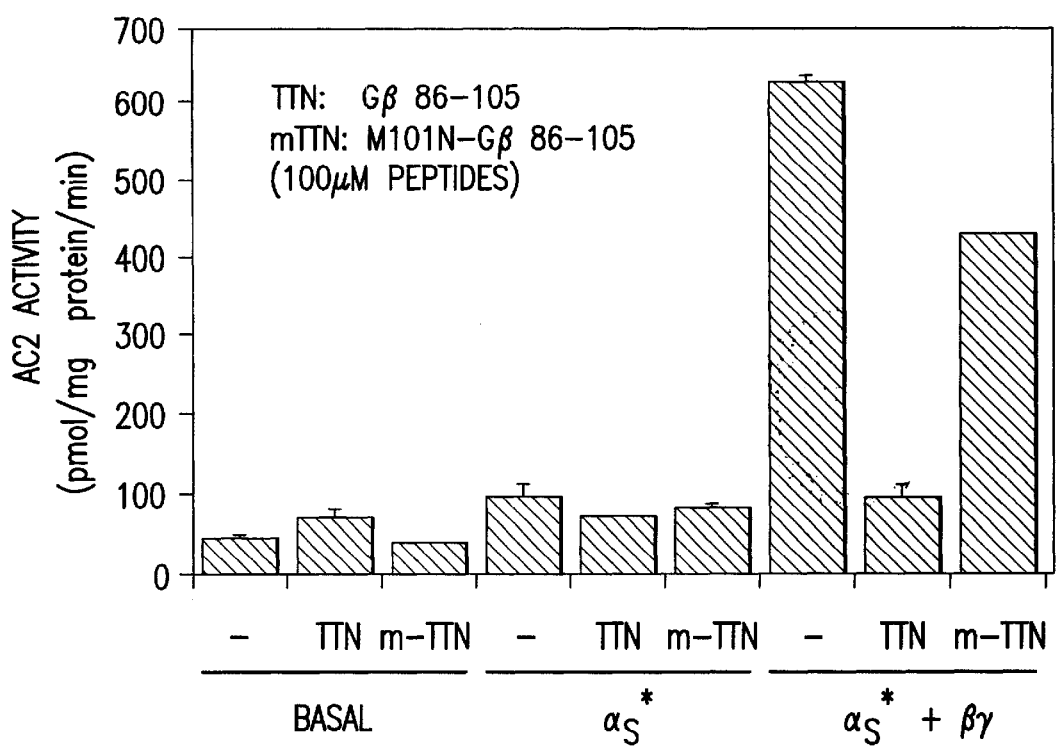
Figure 2C:
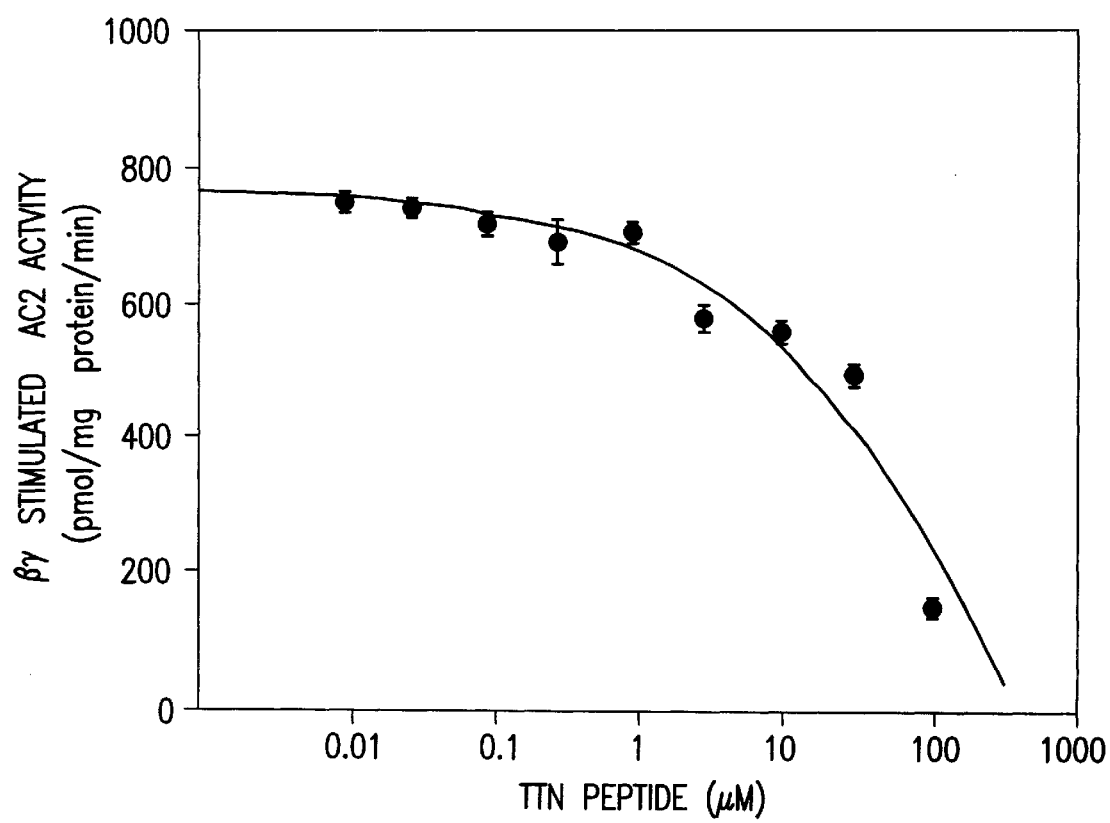
Figure 2D:
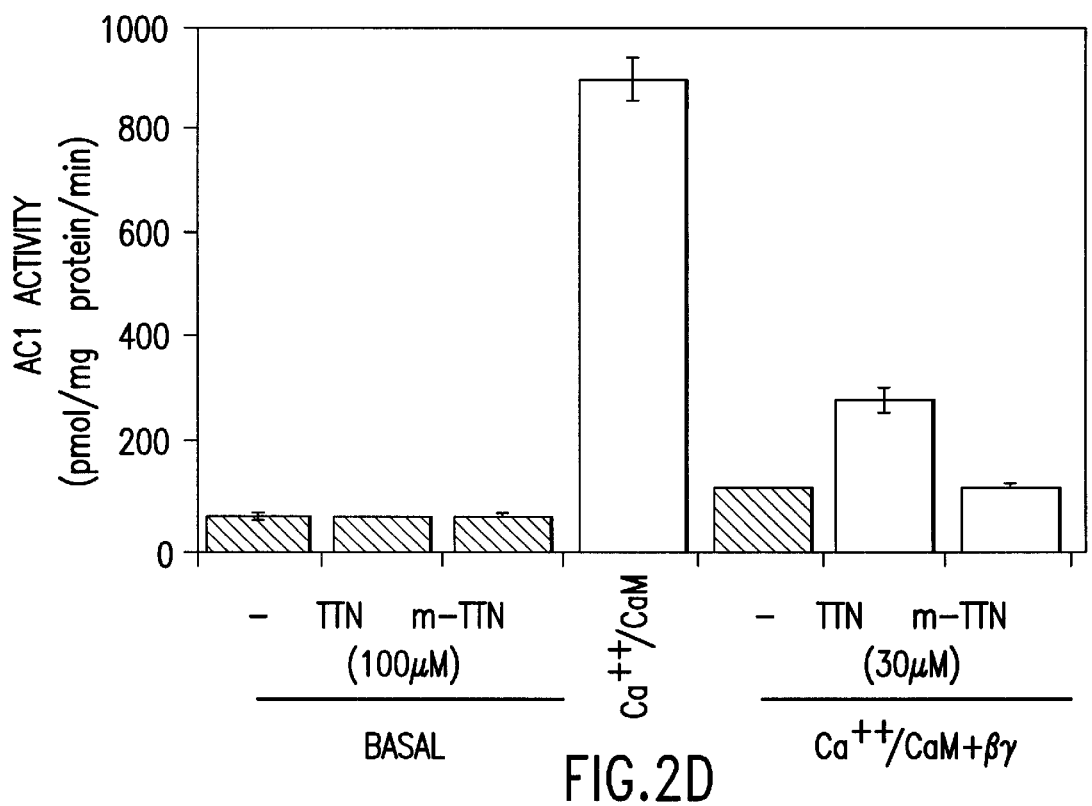
Figure 2E:
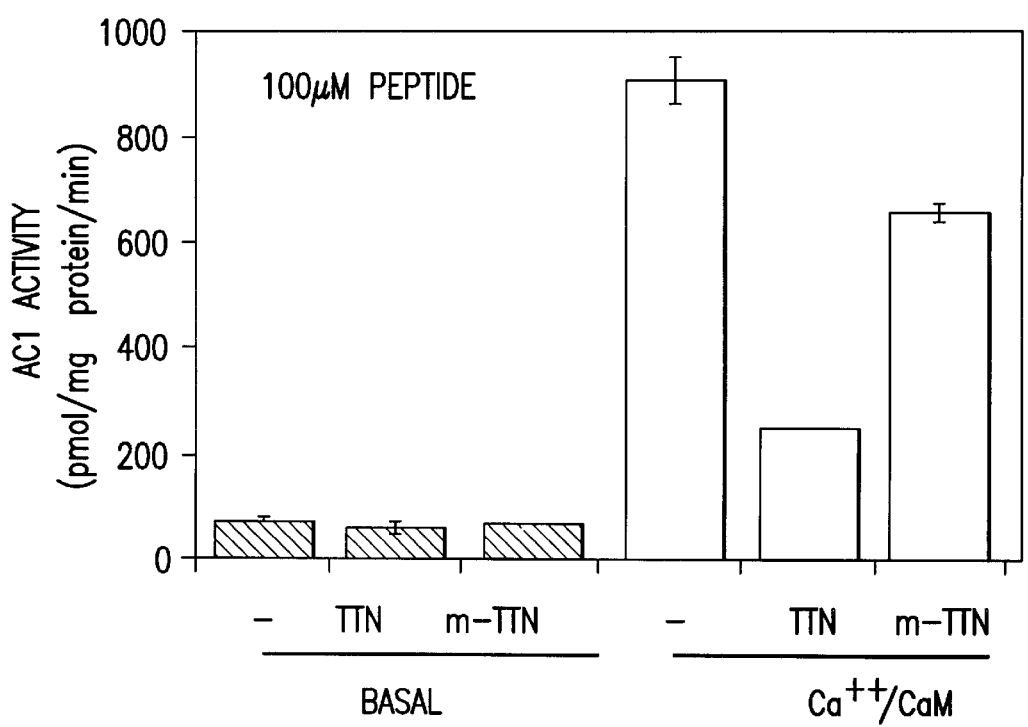

We used the docking model (Weng et al., 1996, J. Biol. Chem. 271, 26445–26448) to obtain predicted contact points between the Gβ and the AC2 956–982 peptide. FIG. 1A shows the backbone of Gβ. The regions of Gβ predicted to interact with the AC2 peptide are shown in pink. Predicted contacts between residues of the AC2 peptide and Gβ (see Molecular Modeling in Section 6.1.2) are shown in FIG. 1B. Since the peptide encodes a region of AC2, we reasoned that the predicted contact residues on Gβ could be involved in communicating signals to effectors. To test this idea, we synthesized peptides encoding sequences from Gβ and determined whether these peptides modulated Gβγ regulation of AC2 and AC1. Two peptides were designed based on the predicted contact interactions between Gβ and AC2 peptide. The first peptide (TTN) encodes the region of residues 86–105 of Gβ, which includes the stretch of residues 91–99 predicted by the model to be important for effector interactions (FIG. 2A). The effects of TTN peptide on the activity of recombinant AC2 expressed in Sf9 cells are shown in FIG. 2 at 100 μM, the peptide did not inhibit basal or activated $\alpha_s$ ($a_s^*$) stimulated activities; however, it significantly inhibited Gβγ-stimulated activity, which is seen only in the presence of $a_s^*$ (Fung et al., 1981, Proc. Natl. Acad. Sci. U.S.A. 78, 152–156). To ascertain the specificity of the peptide effect, we substituted the residue corresponding to Met-101 in Gβ with Asn. This Met is conserved in most Gβ proteins from different species (Sondek et al., 1996, Nature 379, 369–374) and mutation of the residue at this position in yeast abolishes Gα interactions (Whiteway et al., 1994, Mol. Cell. Biol. 14, 3223–3229). The "mutated" peptide (m-TTN) containing Asn at the position corresponding to Gβ-101 was much less efficacious than the TTN peptide in inhibiting Gβγ stimulation (FIG. 2B). The half-maximal concentration at which the TTN peptide inhibited Gβγ stimulation of AC2 was in the range of 30–60 μM (FIG. 2C). Since Gβγ also inhibits AC1, we tested whether the TTN peptide's ability to block Gβγ interactions with effectors could be extended to modulation of Gβγ inhibition of AC1. The recombinant AC1 expressed in Sf9 cells was used in the assays. The TTN peptide did not affect basal activity of AC1. Gβγ inhibited the $Ca^{2+}$/CaM-stimulated AC1 activity whereas m-TTN did not affect Gβγ inhibition (FIG. 2D). Increasing concentrations of TTN peptide further did not result in greater blockade of Gβγ inhibition. The reason for this became apparent when the effect of TTN peptide by itself was evaluated on the $Ca^{2+}$/CaM-stimulated activation of AC1 (FIG. 2E). At 100 μM, TTN peptide inhibited AC1 activity by 50–70%. The M101N "mutant" peptide had greatly reduced capacity to inhibit AC1 (FIG. 2E).

Two other regions of Gβ predicted by the model to be in contact with the crosslinked AC2 peptide are between residues 117–119 and 129–135 (FIG. 1B). Hence, we designed a second peptide (GGL) encoding the region of residues 115–135 of Gβ (SEQ ID NO:6) (FIG. 3A). The GGL peptide did not affect basal AC2 activity and did not significantly inhibit $\alpha_s^*$-stimulated activity, but it did inhibit Gβγ stimulated activity (FIG. 3B). To assess the specificity of this peptide, we converted the residue corresponding to Tyr-124 in Gβ to a Val. This Tyr is conserved in all currently known Gβ from different species (Sondek et al., 1996, Nature 379, 369–374). This "mutated" peptide (m-GGL) was less effective in inhibiting Gβγ stimulation of AC2 (FIG. 3B). In contrast to its effect on AC2, the GGL peptide was not efficacious in blocking Gβγ-induced inhibition of AC1 (FIG. 3C). The m-GGL peptide also showed no effect on Gβγ inhibition of AC2 (FIG. 3C). Like the TTN peptide, the GGL peptide alone was also capable of inhibiting $Ca^{2+}$/CaM-stimulated AC1 activity, but the m-GGL peptide did not inhibit the AC1 activity as extensively as the GGL peptide (FIG. 3C).

6.1.4. Discussion

The results indicate that we have identified a surface on Gβ that is involved in effector interactions. The location of this region at the interface of Gα and Gβγ (Weng et al., 1996, J. Biol. Chem. 271, 26445–26448; Sondek et al., 1996, Nature 379, 369–374) is consistent with the ability of Gα to block effector regulation by Gβγ, as many residues of Gβ that are involved in interactions with Gα, such as Trp-99, Met-101, Leu-117, and Asn-119 (Sondek et al., 1996, Nature 379, 369–374; Lambright et al., 1996, Nature 379, 311–319), are also predicted by our model to interact with effectors. We have explicitly tested the importance of Met-101 that, as shown by the experiments in FIG. 2, is critical for regulation of effector function. We have also shown that the conserved Tyr-124 of Gβ1 is important for effector regulation. FIG. 4 shows how the Gα binding region on Gβ identified from the crystal structure overlaps with an adenylyl cyclase (effector) interaction domain we have identified by molecular modeling.

One issue that arises from these studies is whether the surface on Gβ where the AC2 peptide docks is sufficient for full effector contact. Our experiments indicate that the affinity provided by the interaction of the peptide from this surface is not sufficient to achieve full blockade of Gβγ stimulation of AC2 or to elicit full agonist activity of the Gβ peptides in regulating AC1. Interactions with additional regions of Gβ might be necessary. Alternatively, the remainder of the interactions required to achieve full contact with effectors could involve Gγ. Mutational analyses in yeast have identified three amino acid residues in the N-terminal part of Gγ that are required for effector function (Grishin et al., 1994, Mol. Cell. Biol. 14, 4571–4578). The importance of the protein portion of Gγ in effector regulation remains to be investigated in biochemical experiments. It has also been shown that the posttranslational modification of Gγ that results in farnesylation (γ1 and possibly γ11) or geranylgeranylation (other γs) is required for effector interactions as assessed by biochemical assays with resolved components (Iniguez-Lluhi et al., 1992, J. Biol. Chem. 267, 23409–23417). These results suggest that the specific hydrophobic properties of the acyl group may be required for complete Gβγ action on effectors. Thus, a more complete model for the mode of interaction of Gβγ with effectors may involve both the select protein regions in Gβ and the lipid moiety in Gγ.

6.2. Resolution of a Signal Transfer Region from a General Binding Domain in Gβ for Stimulation of Phospholipase C-β2

Transmembrane signal transfer in heterotrimeric G protein coupled pathways involves sequential protein-protein interactions. We have studied interactions between Gβγ subunits and one of their effectors, phospholipase C-β2 (PLC-β2)(SEQ ID NO:4), to determine if all of the contact points on Gβ (SEQ ID NO:1) are required for signal transfer. A peptide encoding residues 86–105 of Gβ (SEQ ID NO:5) was able to specifically stimulate phospholipase C-β2, and a six amino acid stretch within this sequence (Gβ residues 96–101) (SEQ ID NO:8) was sufficient for signal transfer and thus could be considered as a core signal transfer region. Another peptide encoding Gβ115–135 (SEQ ID NO:6) did not substantially stimulate PLC-β2 by itself but inhibited Gβγ stimulation of PLC-β2, indicating that the 115–135 amino acid stretch of Gβ may be part of a general binding domain. This resolution of signal transfer regions from general binding domains indicates that not all of the interactions in protein-protein contact may be required for signal transfer, and it may be feasible to synthesize agonists and antagonists that regulate signal flow at intracellular sites.

6.2.1. Introduction

Transmembrane signaling in heterotrimeric G protein coupled systems occurs through protein-protein interactions. Agonist occupied receptors interact with G proteins to promote nucleotide exchange and subunit dissociation. The Gα subunits as well as the Gβγ complex interact with and regulate effectors (Gilman, 1987, Ann. Rev. Biochem. 57, 615; Hamm, J. Biol. Chem. 273, 669). The Gβγ complex regulates numerous effectors including K+ channels, adenylyl cyclase 2 (AC2), phospholipase C-β2 and $Ca^{2+}$ channels. A general issue that arises in this mode of signal transduction involving protein-protein interactions is whether all of the contacts between the protein partners are required information flow. In this study, we have addressed this issue in Gβγ regulation of phospholipase C-β2.

We had identified a region within AC2 that was involved in receiving signals from Gβ (Chen et al., 1995, Science 268, 1166). With a peptide encoding this region we had used crosslinking studies and molecular modeling to identify the region 85–145 of Gβ as being involved in effector interactions (Weng et al., 1996, J. Biol. Chem. 271, 26445; and Example 6.1 herein). Independent studies by Yan and Gautam had also identified the first one hundred amino acids of Gβ as being involved in effector action (Yan and Gautam, 1996, J. Biol. Chem. 271, 17597; Yan and Gautam, 1997, J. Biol. Chem. 272, 2056). A detailed site-directed mutagenesis study of Gβ has also confirmed that the region 60–150 is involved in interactions with multiple effectors (Ford et al., 1998, Science 280, 1271). Since a relatively large area of Gβ is involved in effector interactions, we chose one effector, phospholipase C-β2 (PLC-β2), and determined a minimal region of Gβ required for stimulation. We also determined if there were regions of Gβ that are involved in effector interactions but are not required for signal transfer.

6.2.2. Methods

Peptides were synthesized on an Applied Biosystems peptide synthesizer (model 431A) and purified by HPLC on acetonitrile gradients. Purified peptides were lyophilized and stored at −20 degrees C. When needed, peptides were dissolved in HED buffer (10 mM Hepes pH 7.0, 1 mM EDTA pH 8.0, 1 mM DTT). Identity of peptides was verified by mass spectrometry.

Recombinant PLC-β2 was expressed in High 5 cells by infection with recombinant baculovirus. Three to four days after infection, the cells were lysed by par bombing to 600 psi. The lysate was then centrifuged, and the cytosolic fraction was collected. Approximately 10–15 μg of cytosolic fraction was used per 100 μl reaction volume. Phospholipid substrate is a mixture of [3H]PIP2 and unlabeled phospholipids. Unlabeled phospholipids, from Sigma (P-6023), are crude phospholipids from bovine brain. The total diphosphoinositide and triphosphoinositide content is 20–40%. The remainder is a mixture of phosphotidylinositol and phosphotidylserine. Phospholipids are sonicated in 10 mM Hepes pH 7.0 to form micelles. A total of 0.01 μCi of [3H]PIP2, corresponding to approximately 7000 cpm, and 5 μg of unlabeled mixed phospholipids are used per reaction.

The PLC assay was performed as previously described (De Vivo, 1994, Meth. Enzymol. 238, 131). Briefly, substrate, PLC-β2, peptide, and Gβγ subunits are mixed on ice in a 100 μl volume buffer containing 10 mM Hepes pH 7.0, 1 mM DTT, 100 mM KCl, 10 mM NaCl, 2 mM EGTA, 1 mM EDTA, and 1 mM $MgCl_2$. Reactions are started by the addition of 25 μl 5 mM $CaCl_2$ and incubated at 32 degrees C. for 15 minutes. Reactions are stopped by the addition of 1 ml CMH (chloroform:methanol:$H_2O$=100:100:1 by volume) and 250 μl 10 mM EDTA. After extraction, 400 μl aqueous phase is counted using a Beckman scintillation counter. All experiments were repeated at least thrice with very similar results. For concentration-effect curves, typical experiments are shown.

For fluorescent resonance energy transfer experiments, recombinant PLC-β2 was expressed in Sf9 cells and purified as described (Runnel et al., 1996, Biochem. 35, 16824) and labeled with the amine-reactive probe, Cascade Blue acetyl azide (Molecular Probes, Eugene Oreg.) by raising the pH to 8.0 and adding a 4-fold excess of probe from a freshly prepared concentrated DMF solution. The reaction was kept on ice for 30 minutes before extensive dialysis in a solution comprising 20 mM Hepes, 0.16 M NaCl, 1 mM DTT, pH 7.2 to remove excess probe. Peptides were labeled with DABMI (4-dimethyl-5aminophenylazophenyl-4'-maleimeide) using an equimolar amount of dye in the absence of reducing agents. The reaction was allowed to proceed for 30 minutes at room temperature before quenching with 5 mM DTT. The final labeling ratios, as determined by absorption, were 1:1 for CB-PLC-β2 and 0.8 for the two DABMI-peptides. Fluorescence spectra were taken on an ISS-PCL (ISS Champaign, Ill.) photon counting spectrofluorometer using a 3×3 mm cuvette and exciting at 380 nm and scanning from 400–560 nm.

6.2.3. Results and Discussion

We had previously synthesized two peptides encoding regions 86–105 and 115–135 of Gβ that were capable of modulating Gβγ stimulation of AC1 and AC2 (Weng et al., 1997, J. Biol. Chem. 271, 26445; and Example 6.1). We tested the Gβ86–105 peptide (SEQ ID NO:5) on Gβγ stimulation of PLC-β2 (SEQ ID NO:4). In initial experiments we used a sub-saturating concentration of Gβ and looked for inhibition of Gβ stimulation by the Gβ86–105 peptide. Much to our surprise we found that the peptide robustly stimulated PLC-β2 both in the absence and presence of sub-saturating concentrations of Gβγ. The stimulation by maximal concentration of peptide was non-additive with Gβγ stimulation (FIG. 5A). Substitution of Methionine at position 101 renders this peptide inactive for interactions with AC2 and AC1 (Weng et al., 1997, J. Biol. Chem. 271, 26445; and Example 6.1). The Gβ86–105 M101N substituted peptide was not capable of activating PLC-β2 (FIGS. 5B–C), indicating that the 101 position could be important for interactions with PLC-β2. To determine if the stimulation resulted from direct interactions between the peptide and PLC-β2 we tested the binding of the Gβ86–105 peptide to PLC-β2 and compared it to the binding of the Gβ86–105 M101N substituted peptide by fluorescent resonance energy transfer (see Methods in Section 6.2.2). The Gβ86–105 peptide binds to PLC-β2 with a $K_d$ of approximately 1 μM (FIG. 5B), while the Gβ86–105 M101N substituted peptide did not display measurable binding. This binding experiment was conducted both in the presence and absence of phospholipids with identical results, indicating that the binding of the peptide to PLC-β2 is independent of substrate. This is consistent with the ability of the Gβ86–105 peptide to stimulate PLC-β2, while the Gβ86–105 M101N substituted peptide does not stimulate on its own, nor does it inhibit Gβγ stimulation.

Figure 6A:
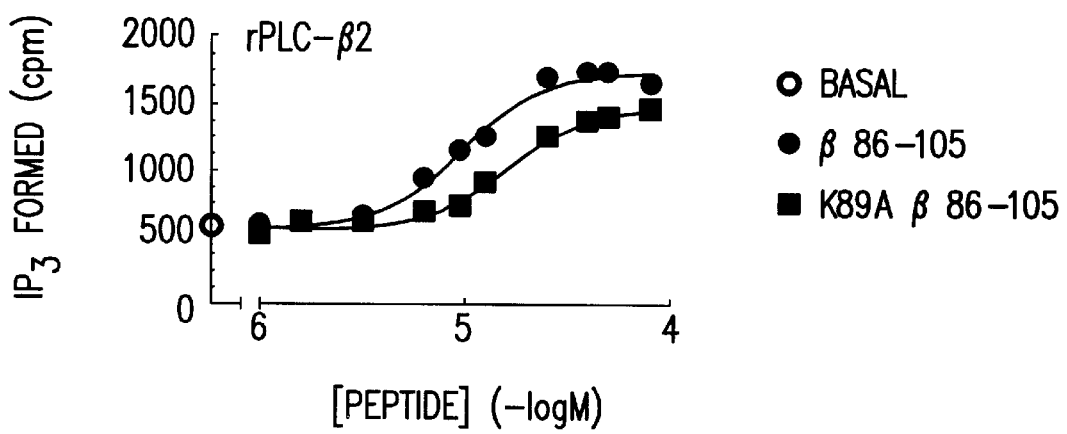
Figure 6B:
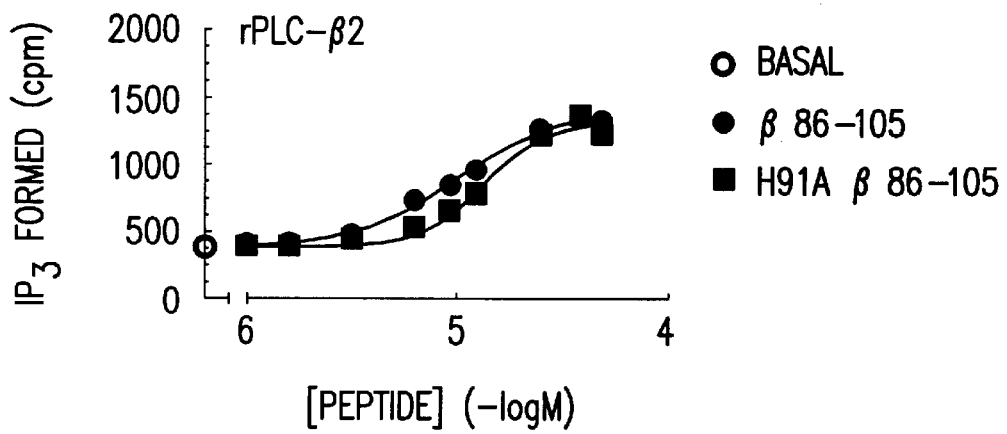
Figure 6C:
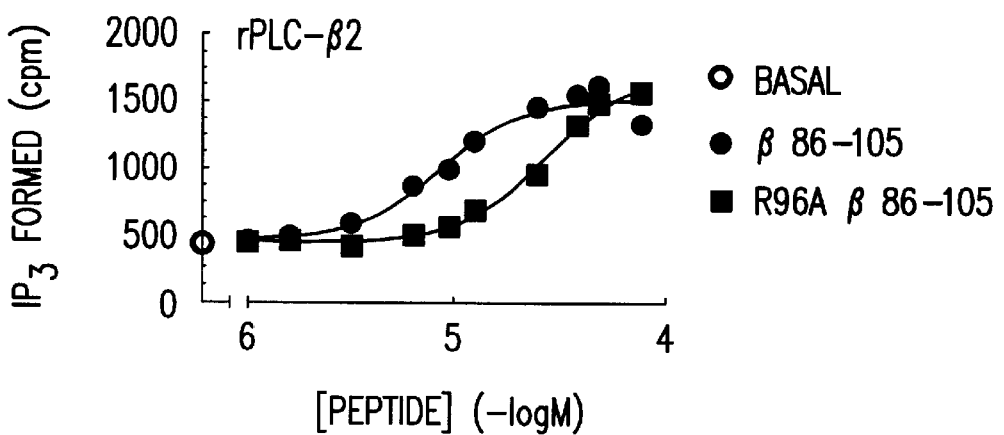

Complementary charge interactions are often key determinants for protein-protein interactions. The Gβ86–105 peptide contains two charged residues K89 and R96, and one histidine, H91. We evaluated the importance of each of these residues for the Gβ86–105 peptide stimulation of PLC-β2. Substitution of each of these residues individually decreased the affinity of the peptide but did not affect maximal stimulation (FIGS. 6A–C). Particularly noteworthy was the large shift in affinity when R96 was substituted (FIG. 6E). Also noteworthy is the agreement in effect when the K89A substitution is made in the peptide or the Gβ subunit through site-directed mutagenesis (Li et al., 1998, J. Biol. Chem. 273, 16265; Panchenko et al., 1998, J. Biol. Chem. 273, 28298). When all three residues were substituted simultaneously, the peptide did not stimulate PLC-β2 (FIG. 6D) and did not affect Gβγ stimulation of PLC-β2 (FIG. 6E). These results indicate that charge interactions may be crucial for both interactions and signal transfer from Gβγ to PLC-β2.

Figure 6D:
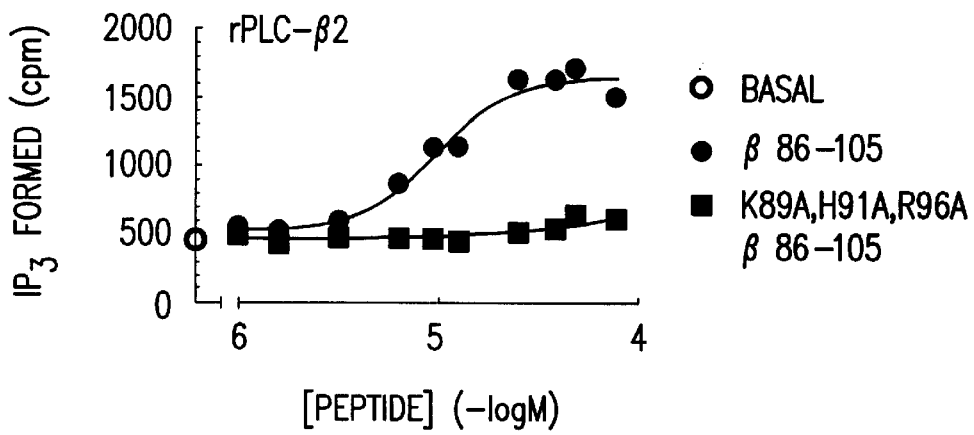
Figure 6E:
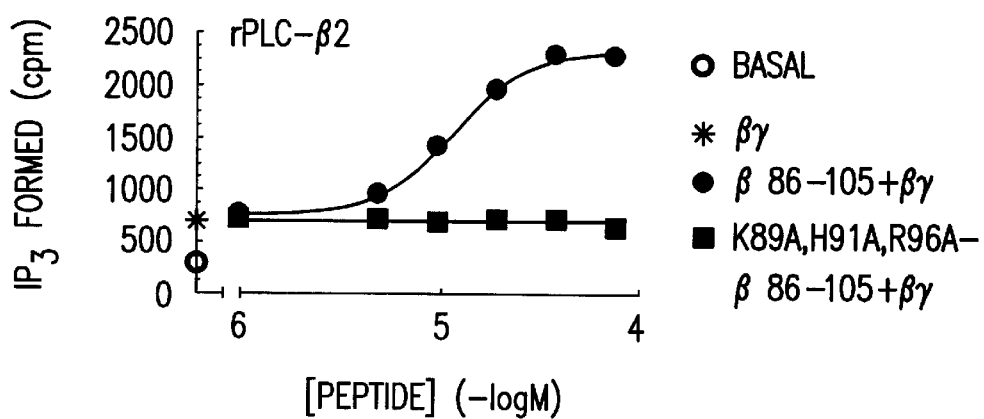
Figure 6F:
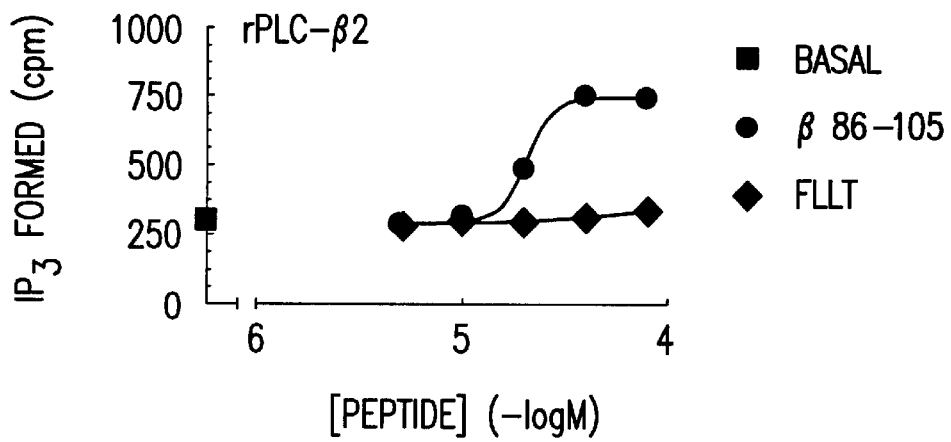
Figure 6G:
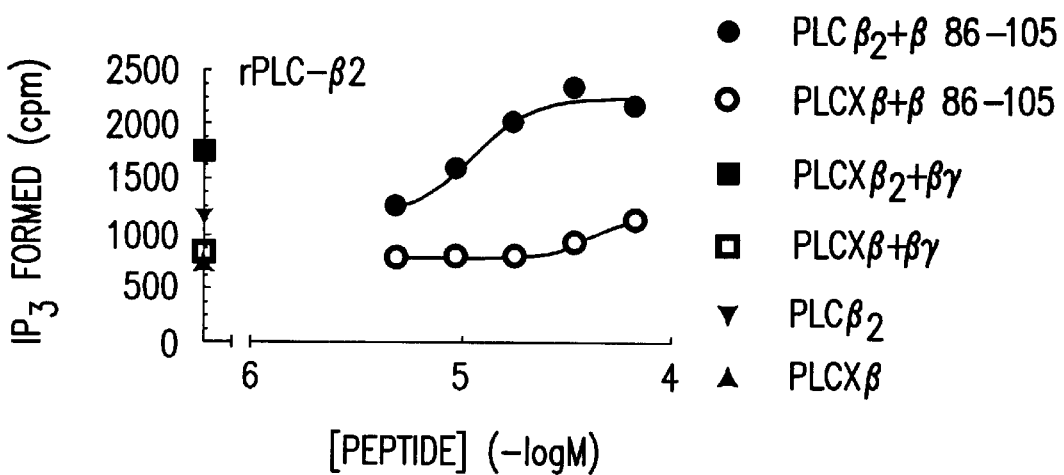

The experiments in FIGS. 6D–E also raise the possibility that charged peptides non-specifically activate PLC-β2. Hence we tested the effects of an unrelated peptide, FLLT, on PLC-β2 activity. FLLT encodes region 660–688 of adenylyl cyclase 6 and has the same overall change (+2 at pH 6.8–6.9) as the Gβ86–105 peptide. While the Gβ86–105 peptide stimulates, the FLLT peptide has no measurable effects (FIG. 6F). These results demonstrate that the stimulatory effects of the Gβ86–105 peptide on PLC-β2 are not solely due to the charge of the peptide. To ascertain whether the Gβ86–105 peptide stimulation of PLC-β2 was selective, we tested the ability of this peptide to stimulate PLC-Xβ, an isoform of PLCβ from Xenopus that is stimulated poorly by Gβγ subunits under our assay conditions. While the Gβ86–105 peptide stimulates PLC-β2 robustly, it has relatively little ability to stimulate PLC-Xβ (FIG. 6G). This experiment shows that the Gβ86–105 peptide selectively stimulates an isoform of PLCβ that is regulated by Gβγ subunits.

We next analyzed the importance of the serines at positions 97 and 98 in signal transfer. Site directed mutagenesis studies have shown that S98A mutants of Gβ stimulate PLC-β2 more extensively (Ford et al., 1998, Science 280, 1271). We studied the effects of four types of substitutions at this position. When S98 was substituted with alanine (FIG. 7A) there is approximately a 2-fold increase in the affinity with which the peptide stimulates. This is consistent with the site-directed mutagenesis experiment (Ford et al., 1998, Science 280, 1271). When both serines were substituted with arginine there was a five-fold increase in affinity of the peptide (FIG. 7B). In contrast, substitution with asparagine resulted in an inactive peptide while substitution with cysteine resulted in greatly reduced affinity (FIG. 7C).

Figure 8A:
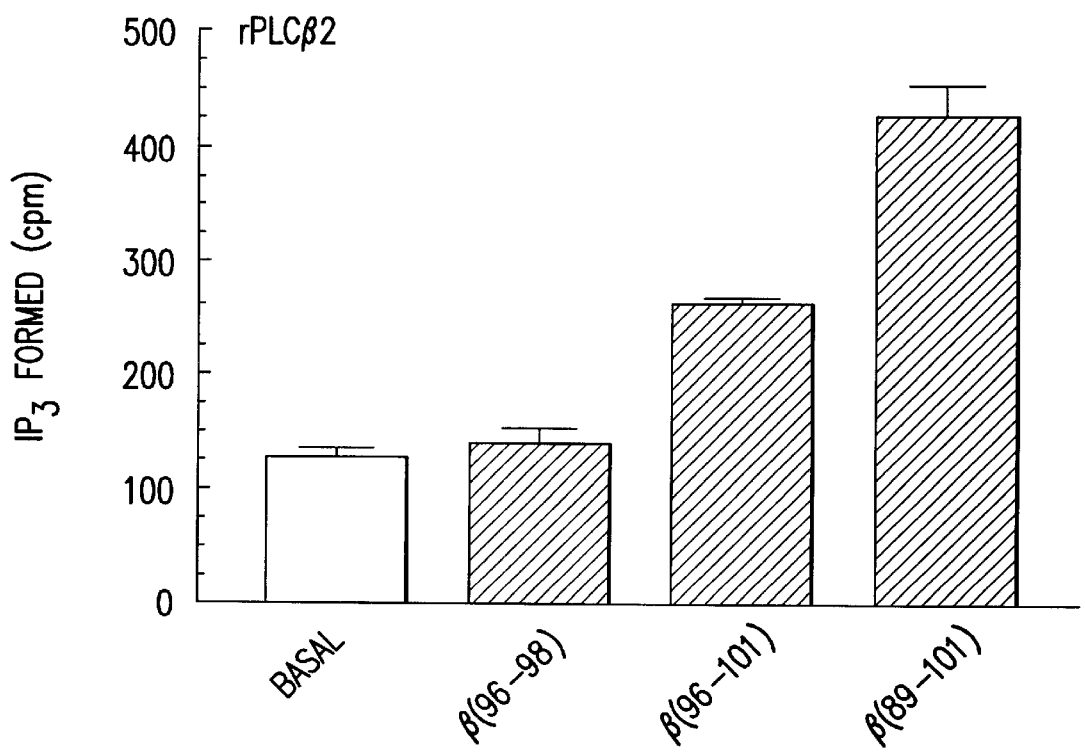
Figure 8B:
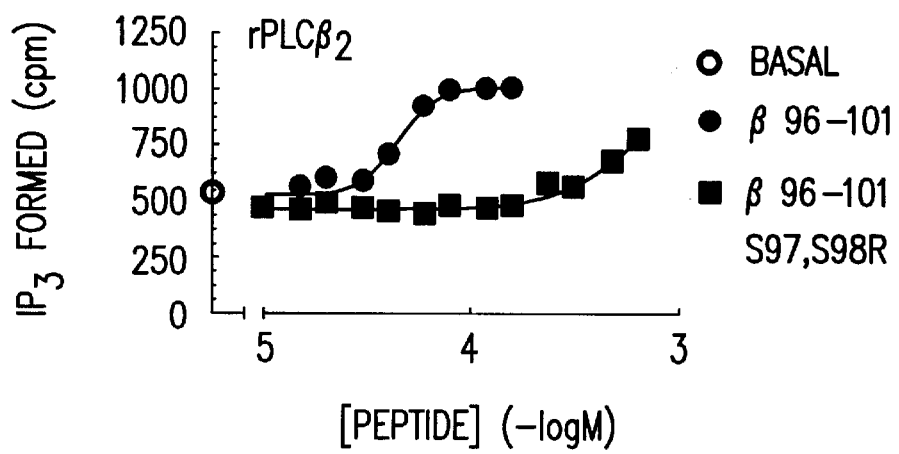
Figure 8C:
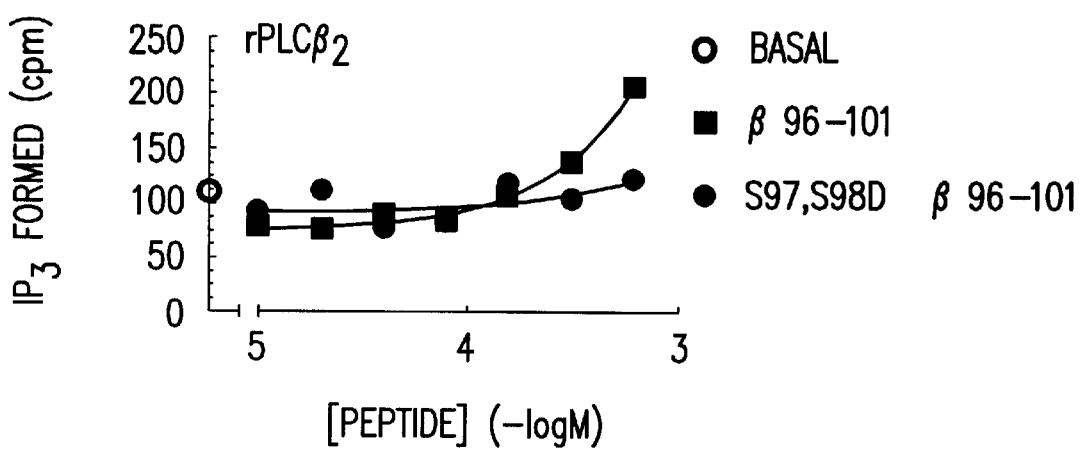
Figure 8D:
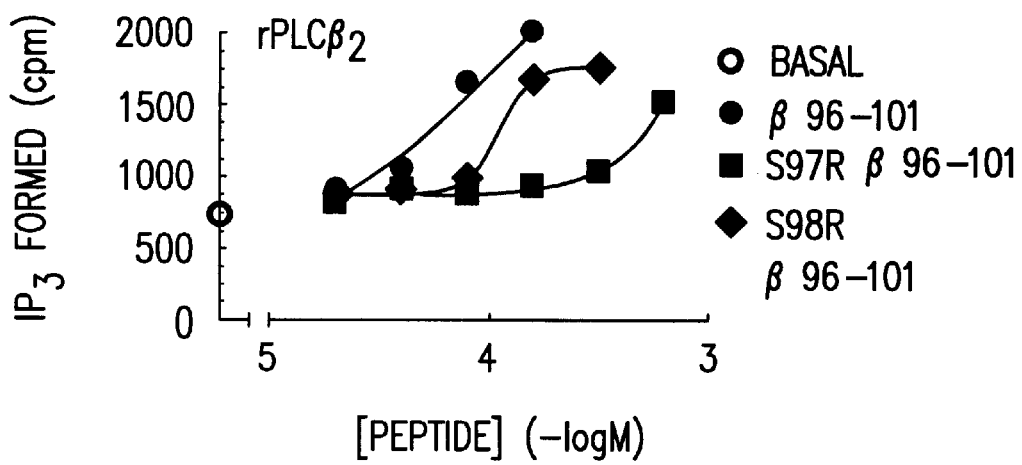
Figure 8E:
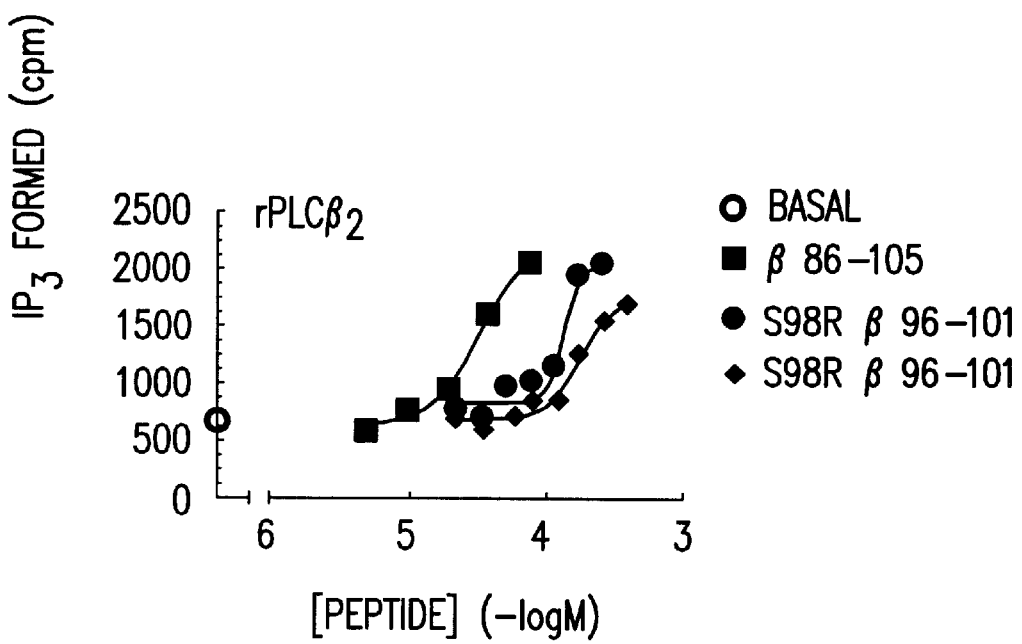

These experiments suggested that the region around 96–101 was crucial for signal transfer, and peptides encoding shorter regions of Gβ might be capable of stimulating PLC-β2. Hence, we tested several short peptides including a three amino acid peptide encoding residues 96–98, a six amino acid peptide encoding residues 96–101 (SEQ ID NO:8) and a thirteen amino acid peptide encoding residues 89–101 (SEQ ID NO:7). The three amino acid peptide did not stimulate PLC-β2, but the six amino acid peptide as well as the thirteen amino acid peptide did stimulate (FIG. 8A). Since the Gβ96–101 six amino acid peptide was the smallest peptide we had found that stimulated PLC-β2, we analyzed it further. Concentration-effect curves showed that it had considerably lower affinity than the Gβ86–105 peptide (FIG. 8B). However, when the serines corresponding to position 97 and 98 were substituted by arginines (SEQ ID NO:9), the six amino acid peptide stimulated with an apparent $K_{act}$ of 30 μM (FIG. 8B) as compared to 5–10 μM $K_{act}$ for the Gβ86–105 peptide (FIG. 5 through FIG. 7). In contrast, when the serines were substituted with Asp the six amino acid peptide did not stimulate PLC-β2 (FIG. 8C). The relative role of the two serines was further investigated by individually substituting them with arginine. While both substitutions increase affinity of stimulation, substitution at position 97 (SEQ ID NO:10) results in stimulation of PLC-β2 with both a higher affinity and a higher efficacy than the substitution at position 98 (FIG. 8D). In fact, the efficacy of the S97R substituted peptide (SEQ ID NO:10) is the same as that for the full length Gβ86–105 peptide (SEQ ID NO:5) (FIG. 8E), indicating that this stretch of six amino acids retains the full capacity to transmit signals, albeit with lower affinity. These results also indicate that it is the relative positions of the amino acids which contributes to their effect, not simply the amino acid composition. The data in FIGS. 8A–E show that amino acids 96 to 101 of Gβ constitute a core signal transfer region for activation of PLC-β2. If this region is sufficient for signal transfer then what is the role of the other regions of Gβ that interact with PLC-β2? One role may be to contribute to the overall affinity of the interactions but not be involved in signal transfer. If this were the case then a peptide encoding such a region should inhibit Gβγ stimulation of PLC-β2, but by itself would not stimulate PLC-β2. We tested a peptide encoding residues 115–135 of Gβ for such effects. We had previously shown that the Gβ115–135 peptide modulated Gβγ stimulation of both AC2 and AC1 (Weng et al., 1996, J. Biol. Chem. 271, 26445; and Example 6.1). The Gβ115–135 peptide marginally (~20%) stimulated PLC-β2 by itself, but when added with Gβγ, substantially inhibited Gβγ stimulation of PLC-β2. When the conserved tyrosine at position 124 was substituted, the peptide was inactive (FIG. 9A). The Gβ115–135 peptide inhibits with an apparent $K_{act}$ of 5 μM (FIG. 9B). Thus we conclude that the 115–135 region of Gβ constitutes a general binding domain involved in Gβγ interactions with PLC-β2, but not required for signal transfer.

The position of the residues identified in these studies relative to the remainder of the protein is summarized in a ribbon diagram of Gβγ (FIG. 10). In FIG. 10, Gβ is shown in khaki, Gγ is shown in grey, residues 96–101 of Gβ are shown in pink, and residues 115–135 of Gβ are shown in aqua.

These studies demonstrate that all of the contacts between two proteins are not required for signal transfer. In the case of Gβγ and PLC-β2, our data show that a relatively short stretch of six amino acids (i.e. residues 96–101 of Gβ) (SEQ ID NO:8) is sufficient to transfer the signal (in this case, enzyme activation). Substitution of residues within the six amino acid peptide produces a more potent peptide than the naturally occurring sequence. Thus the naturally occurring residues in signal transfer regions may not be optimized for this particular set of interactions. Such sub-optimal interactions may be one mechanism to achieve regulated reversibility. It should also be noted that the Gβ 586–105 peptide does not stimulate AC2 in the presence of Gαs (Weng et al., 1996, J. Biol. Chem. 271, 26445; and Example 6.1), suggesting that there may be different signal transfer regions on Gβ for different effectors. The Gβ115–135 peptide minimally stimulates PLC-β2, but is very (~80%) effective in inhibiting Gβγ stimulation of PLC-β2 presumably by interacting with PLC-β2. This indicates that 115–135 region of Gβ is not crucial for signal transfer but is part of a general binding domain that participates in interactions with PLC-β2. The core signal transfer region and general binding domain we have identified is shown with a ribbon diagram of Gβγ derived from the crystal structure (Sondek et al., 1996, Nature 279, 369).

What is the relevance of such a functional resolution between signal transfer regions and general binding domains within the overall interaction area? From the perspective of protein engineering, it offers a built-in capability to regulate the affinity of interaction between the protein partners and thus make reversibility feasible. Peptide hormones have long been recognized to have distinct address and message regions (Schwyzer, 1980, Proc. R. Soc. Lond. 210, 5; Portoghese, 1989, TIPS, 10, 230) that are involved in binding interactions with receptors and activation of intracellular signaling pathways, respectively. This functional resolution of peptide hormones has been used for the design of peptidomimetic antagonists (Portoghese et al., 1990, J. Med. Chem. 33, 1714). Similarly, our resolution of a signal transfer region from general binding domain for interactions between intracellular proteins provides an approach to identifying molecular interactions relevant for development of agonists and antagonists at intracellular protein interaction sites. The interactions between the signal transfer region peptide and PLC-β2 could form the basis for synthesis of agonists that mimic receptor-dependent activation of PLC-β2. In contrast, the interactions between the Gβ115–135 peptide and PLC-β2 would form the basis for synthesis of antagonists that block receptor-dependent activation of PLC-β2. Signaling pathways are major targets for therapeutic agents. Until now, agonists and antagonists have largely focused on extracellular receptor sites. These studies, for the first time, indicate that it may be feasible to design agonists and antagonists directed at the interface between signaling components inside the cell.

The invention described and claimed herein is not to be limited in scope by the specific embodiments herein disclosed since these embodiments are intended as illustrations of the several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. Throughout this application various references are cited, the contents of each of which is hereby incorporated by reference into the present application in its entirety.

We claim:

1. An isolated peptide or derivative thereof selected from the group consisting of SEQ ID NO: 5, SEQ ID NO: 6, SEQ ID NO: 7, SEQ ID NO: 8, SEQ ID NO:9, and SEQ ID NO:10, wherein said peptide or derivative thereof is capable of immunospecific binding to anti-peptide antibody.

2. The peptide of claim 1, wherein the peptide or derivative thereof is or is derived from SEQ ID NO: 5.

3. The peptide of claim 1, wherein the peptide or derivative thereof is or is derived from SEQ ID NO: 6.

4. The peptide of claim 1, wherein the peptide or derivative thereof is or is derived from SEQ ID NO: 7.

5. The peptide of claim 1, wherein the peptide or derivative thereof is or is derived from SEQ ID NO: 8.

6. The peptide of claim 1, wherein the peptide or derivative thereof is or is derived from SEQ ID NO: 9.

7. The peptide of claim 1, wherein the peptide or derivative thereof is or is derived from SEQ ID NO: 10.

8. A chimeric peptide comprising the peptide or derivative of claim 1 fused by a covalent bond to a second peptide.

9. A chimeric peptide comprising the peptide or derivative of claim 1 fused by a covalent bond to a cell permeable carrier.

10. A purified recombinant peptide produced by a method comprising:
   (a) growing a recombinant cell containing a nucleic acid comprising a nucleotide sequence encoding an amino acid sequence selected from the group consisting of SEQ ID NO:5, SEQ ID NO:6, SEQ ID NO:7, SEQ ID NO:8, SEQ ID NO:9 and SEQ ID NO:10 such that the encoded peptide is expressed by the cell; and
   (b) recovering the expressed recombinant peptide.

11. The peptide of claim 10, wherein the peptide or derivative thereof is or is derived from SEQ ID NO: 5.

12. The peptide of claim 10, wherein the peptide or derivative thereof is or is derived from SEQ ID NO: 6.

13. The peptide of claim 10, wherein the peptide or derivative thereof is or is derived from SEQ ID NO: 7.

14. The peptide of claim 10, wherein the peptide or derivative thereof is or is derived from SEQ ID NO: 8.

15. The peptide of claim 10, wherein the peptide or derivative thereof is or is derived from SEQ ID NO: 9.

16. The peptide of claim 10, wherein the peptide or derivative thereof is or is derived from SEQ ID NO: 10.

17. A pharmaceutical composition comprising:
   a) a peptide or derivative thereof selected from the group consisting of SEQ ID NO: 5, SEQ ID NO: 6, SEQ ID NO: 7, SEQ ID NO: 8, SEQ ID NO:9, and SEQ ID NO:10, wherein said peptide or derivative thereof is capable of immunospecific binding to anti-peptide antibody, and
   b) a pharmaceutically acceptable carrier.

18. The composition of claim 17 wherein the peptide or derivative thereof is or is derived from SEQ ID NO: 5.

19. The composition of claim 17 wherein the peptide or derivative thereof is or is derived from SEQ ID NO: 6.

20. The composition of claim 17 wherein the peptide or derivative thereof is or is derived from SEQ ID NO: 7.

21. The composition of claim 17 wherein the peptide or derivative thereof is or is derived from SEQ ID NO: 8.

22. The composition of claim 17 wherein the peptide or derivative thereof is or is derived from SEQ ID NO: 9.

23. The composition of claim 17 wherein the peptide or derivative thereof is or is derived from SEQ ID NO: 10.

* * * * *